US006693087B1

(12) United States Patent
Murdin et al.

(10) Patent No.: US 6,693,087 B1
(45) Date of Patent: Feb. 17, 2004

(54) NUCLEIC ACID MOLECULES ENCODING POMP91A PROTEIN OF *CHLAMYDIA*

(75) Inventors: Andrew D. Murdin, Newmarket (CA); Pamela L. Dunn, Mississauga (CA); Raymond P. Oomen, Schomberg (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/377,850

(22) Filed: Aug. 20, 1999

Related U.S. Application Data

(60) Provisional application No. 60/097,198, filed on Aug. 20, 1998.

(51) Int. Cl.[7] .................... A61K 39/395; A61K 31/70; C07H 21/04

(52) U.S. Cl. .................... 514/44; 536/23.4; 424/130.1

(58) Field of Search .................... 424/184.1, 185.1, 424/263.1, 130.1; 435/320.1; 536/23.1, 23.7, 24.3; 514/44, 2

(56) References Cited

U.S. PATENT DOCUMENTS

| | | | |
|---|---|---|---|
| 4,168,062 A | 9/1979 | McCarthy et al. | |
| 4,722,848 A | 2/1988 | Paoletti et al. | 424/89 |
| 4,882,278 A | 11/1989 | Mekalanos | 435/172.3 |
| 4,920,209 A | 4/1990 | Davis et al. | 435/235 |
| 4,945,050 A | 7/1990 | Sanford et al. | 435/172.1 |
| 4,952,496 A | 8/1990 | Studier et al. | 435/91 |
| 5,015,580 A | 5/1991 | Christou et al. | 435/172.3 |
| 5,028,530 A | 7/1991 | Lai et al. | 435/69.1 |
| 5,057,546 A | 10/1991 | Sudan | 521/107 |
| 5,283,185 A | 2/1994 | Epand et al. | 435/172.3 |
| 5,364,773 A | 11/1994 | Paoletti et al. | 435/69.1 |
| 5,527,928 A | 6/1996 | Nantz et al. | 554/105 |

FOREIGN PATENT DOCUMENTS

| | | |
|---|---|---|
| EP | 187702 | 7/1986 |
| WO | WO 88/06626 | 9/1988 |
| WO | WO 88/09336 | 12/1988 |
| WO | WO 90/00594 | 1/1990 |
| WO | WO 90/11092 | 10/1990 |
| WO | WO 91/00359 | 1/1991 |
| WO | WO 91/13157 | 9/1991 |
| WO | WO 91/15501 | 10/1991 |
| WO | WO 92/01796 | 2/1992 |
| WO | WO 92/11354 | 7/1992 |
| WO | WO 92/11361 | 7/1992 |
| WO | WO 92/21376 | 12/1992 |
| WO | WO 93/17706 | 9/1993 |
| WO | WO 93/18759 | 9/1993 |
| WO | WO 93/19768 | 10/1993 |
| WO | WO 94/01533 | 1/1994 |
| WO | WO 94/16737 | 8/1994 |
| WO | WO 94/19482 | 9/1994 |
| WO | WO 94/21797 | 9/1994 |
| WO | WO 94/24263 | 10/1994 |
| WO | WO 94/25608 | 11/1994 |
| WO | WO 95/02397 | 1/1995 |
| WO | WO 95/17211 | 6/1995 |
| WO | WO 95/26356 | 10/1995 |
| WO | WO 96/06627 | 3/1996 |
| WO | WO 96/14831 | 5/1996 |
| WO | WO 98 02546 | 1/1998 |
| WO | WO 99 27105 | 6/1999 |

OTHER PUBLICATIONS

Grayston et al. (1995), Journal of Infectious Diseases 168:1231–1235.

Campos et al. (1995), Investigation of Ophthalmology and Visual Science 36:1477–1491.

Grayston et al (1990), Journal of Infectious Diseases 161:618–625.

Marrie (1993), Clinical Infectious Diseases. 18:501–515.

Wang et al (1986), Chlamydial infections, Cambridge Univesity Press, Cambridge. p. 329–332.

Normann et al., Acta Paediatrica, 1998, Vol 87, Iss 1, pp 23–27.

Saikku et al. (1988), Lancet:983–985.

Thom et al. (1992), JAMA 268:68–72.

Linnanmaki et al. (1993), Circulation 87:1030–1034.

Saikku et al. (1992), Annals Internal Medicine 116:273–278.

Melnick et al(1993), American Journal of Medicine 95:499–504.

Shor et al. (1992), South African. Medical Journal 82:158–161.

Kuo et al. (1993), Journal of Infectious Diseases 167:841–849.

Kuo et al. (1993), Arteriosclerosis and Thrombosis 13:1500–1504.

Campbell et al (1995), Journal of Infectious Diseases 172:585–588.

Chiu et al. Circulation, 1997 96(7);2144–2148.

Ramirez et al (1996) Annals of Internal Medicine 125:979–982.

Jackson et al. Abst. K121, p272, 36th ICAAC, Sep. 15–18, 1996, New Orleans.

Fong et al (1997) Journal of Clinical Microbiology 35:48–52.

Hahn DL, et al. Evidence for Chlamydia pneumoniae infection in steroid–dependent asthma. Ann Allergy Asthma Immunol. 1998 Jan.; 80(1): 45–49.

Hahn DL, et al. Association of Chlamydia pneumoniae IgA antibodies with recently symptomatic asthma. Epidemiol Infect. 1996 Dec.; 117(3): 513–517.

Bjornsson E, et al. Serology of chlamydia in relation to asthma and bronchial hyperresponsiveness. Scand J Infect Dis. 1996; 28(1): 63–69.

Hahn DL. Treatment of *Chlamydia pneumoniae* infection in adult asthma: a before–after trial. J Fam Pract. 1995 Oct.; 41(4): 345–351.

(List continued on next page.)

*Primary Examiner*—Deborah Crouch
*Assistant Examiner*—Joseph Woitach

(57) ABSTRACT

An isolated and purified nucleic acid molecule encoding a POMP91A protein of a strain of Chlamydia, is useful for nucleic acid immunization of a host, including a human host, against disease caused by infection by a strain of Chlamydia, particularly *C. pneumoniae*.

16 Claims, 37 Drawing Sheets

OTHER PUBLICATIONS

Allegra L, et al. Acute exacerbations of asthma in adults: role of Chlamydia pneumoniae infection. Eur Respir J. 1994 Dec.; 7(12): 2165–2168.
Hahn DL, et al. Association of Chlamydia pneumoniae (strain TWAR) infection with wheezing, asthmatic bronchitis, and adult–onset asthma. JAMA. Jul. 10;1999 266(2): 225–230.
Pal et al.(1996) Infection and Immunity.64:5341–5348.
Jones et al. (1995) Vaccine 13:715.
Igietseme et al. (1993) Immunology 5:317 (See #29 below).
Igietseme et al (1993) Regional Immunology 5:317.
Magee et al (1993) Regional Immunology 5: 305–311.
Landers et al (1991) Infection & Immunity 59:3774–3777.
Magee et al (1995) Infection & Immunity 63:516–521.
Cotter et al. (1995) Infection and Immunity63:4704–4714.
Campbell et al (1990) Infection and Immunity 58:93–97.
McCafferty et al (1995) Infection and Immunity 63:2387–2389.
Knudsen et al (1996) Third Meeting of the European Society for Chlamydia Research, Vienna.
Wiedmann–Al–Ahmad M, et al. Reactions of polyclonal and neutralizing anti–p54 monoclonal antibodies with an isolated, species–specific 54–kilodalton protein of Chlamydia pneumoniae. Clin Diagn Lab Immunol. 1997 Nov.; 4(6): 700–704.
Hughes et al., 1992. Infect. Immun. 60(9):3497–3503.
Dion et al., 1990. Virology 179:474–477.
Snijders et al., 1991. J. Gen. Virol. 72:557–565.
Langeveld et al., Vaccine 12(15): 1473–1480, 1994.
Ausubel et al., Current Protocols in Molecular Biology, John Wiley & Sons Inc., 1994.
Kunkel et al. Proc. Natl. Acad. Sci. USA (1985) 82:448–492.
Silhavy et al. Experiments with Gene Fusions, Cold Spring Harbor Laboratory Press, 1984.
Davis et al. A Manual for Genetic Engineering: Advanced Bacterial Genetics, Cold Spring Harbor Laboratory Press, 1980).
Casey & Davidson, Nucl. Acid Res. (1977) 4:1539–1553.
Cagnon et al., Protein Engineering (1991) 4(7):843–847.
Takase et al., J. Bact. (1987) 169:5692–5699.
Perez Melgosa et al., Infect Immun (1994) 62:880–886.
Watson et al., Nucleic Acids Res (1990) 18:5299.
Watson et al., Microbiology (1995) 141:2489–2497.
Melgosa et al., FEMS Microbiol Lett (1993) 112:199–204.
Campbell et al., J Clin Microbiol (1990) 28 :1261.1264.
Iijima et al., J. Clin Microbiol (1994) 32:583.–588.
Tartaglia et al, Virology (1992) 188:217–232.
Taylor et al, Vaccine (1995) 15:359.
Kieny et al., Nature (1994) 312:163.
Mekalanos et al., Nature (1983) 306:551–557.
Nakayama et al., Bio/Tech. (1988) 6:693–697.
High et al., EMBO (1992) 11:1991–1999.
Sizemore et al., Science (1995) 270:299–302.
Medaglini et al., Pro. Natl. Acad. Sci. USA (1995) 92:6868–6872.
Flynn J.L., Cell. Mol. Biol. (1994) 40 (suppl. I):31–36.
Norton & Coffin, Molec. Cell Biol. (1985) 5:281–290.
Li et al., Gene (1989) 78:243–254.
Li & Paulin, J. Biol. Chem. (1991) 266:6562–6570.
Li & Paulin, J. Biol. Chem. (1993) 268:10403–10415.
Hartikka et al., Human Gene Therapy (1996) 7:1205–1217.
Tang et al., Nature (1992) 356:152–154.
Davis et al., Vaccine 1994, 12:1503–1509.
Nielsen et al., Science (1991) 254:1497–1500.
Southern, J. Mol. Biol. (1975) 98:503–517.
Dunn et al., Cell (1977) 12:23–36.
Towbin et al., Proc. Natl. Acad. Sci. USA (1779) 76:4350–4354.
Laemmli, Nature (1970) 227:680–685.
Bachmaier et al., Science (1999) 283:1335–1338.
Yang et al., 1993, Infection & Immunity, vol. 61, pp 2037–2040.
Chi E.Y., Kuo C.C., Grayston J.T., 1987. Unique ultrastructure in the elementary body of Chlamydia sp strain TWAR. J. Bacteriol 169(8): 3757–63.
Needleman, S.B., and Wunsch, C.D. 1970, J. Mol Biol. 48:443–453.
Sellers, P.H. 1974 On the theory and computation of evolutionary distances. J. Appl. Math(Siam) 26:787–793.
Waterman, M.S., Smith, T.F., and Beyer, W.A. 1976. Advan. Math. 20:367–387.
Smith, T.F., and Waterman, M.S. 1981 Identification of common molecular subsequences. J. Mol. Biol. 147:195–197.
Sobel, E. and Martinez, H.M. 1985 A Multiple Sequence Alignment Program. Nucleic Acid Res. 14:363–374.
Chapman S. B et al Nucleic Acids Research, vol. 19, No. 14 3979–3986.
Bannantine J.P., Rockey D.D., Hackstandt T. Molecular Microbiology (1998) 28(5), 1017–1026.
Gaydos A.C., Quinn T.C., BoBo D.L. Eiden J.J., Infection and Immunityy (1992), p. 5319–5323.
Promega "1997 Promega Catalog" p. 136.
Invitrogen: "1997 Product Catalog" p. 45.
Batein N. et al Vaccine vol. 15 No. 12/13 pp. 1385–1390 1997.
Kalman et al. GenCore Accession No. AE001638, Mar. 1999.*
Kalman et al. GenCore Accession No. D72067, Apr. 1999.*
Adams et. al.; Initial assessment of human gene diversity and expression patterns based upon 83 million nucleotides of cDNA sequence, 1995, Nature377. Accession AA 331166.*
Adams et.al.; Initial assessement of human gene diversity and expression patterns based upon 83 million nucleotides of cDNA sequence, 1995, Nature 377 Accession AA309135.*
Bachmaier et al., Chlamydia infections and heart disease linked through antigenic mimicry, 1999, SCIENCE, vol. 283, pp. 1335–1339.*
Ertl et al., Genetic immunization, 1996, Viral Immunology, vol. 9, pp. 1–9.*
Monteil et al., Genetic immunization of seronegative one-day–old piglets against pseudorabies induces neutralizing antibodies but not protection and is ineffective in piglets from immune dams, 1996, VET. RES., vol. 27, pp. 443–452.*
Yasutomi et al., A vaccine–elicited, single viral epitope–specific cytotoxic T lymphocyte response does not protect against intravenous, cell–free simian immunodeficiency virus challenge, 1995, Journal of Virology, pp. 2279–2284.*
Kalman S. et al: "Comparative genomes of Chlamydia pneumoniae and C. trachomatis." Nature Genetics, (Apr. 1999) 21 (4) 385–9. XP000853883.
Kalman S. et al: "Comparative genomes of Chlamydia pneumoniae and C. trachomatis" Embl Database Entry Q9Z813, May. 1, 1999 XP 002126979.

Kalman S. et al: "Comparative genomes of Chlamydia pneumoniae and C. trachomatis" Trembl Database Entry Q9Z813, May 1, 1999 XP 002126979.
Biendo M. et al: "Limits of the microimmunofluorescence test and advantages of immunoblotting in the diagnosis of chlamydiosis." Clinical and Diagnostic Laboratory Immunology, (Nov. 1996) 3 (6) 706–9 XP0008535580.
Naidu, Brindha R. et al: "MOMO–based PCR reveals presence of Chlamydia pneumoniae DNA in respiratory and serum samples of patients with acute C. pneumoniae–associated infections." Journal of Microbiological Methods, (1997) vol. 28, No. 1, pp 1–9, XP000853724.

* cited by examiner

FIG. 1A

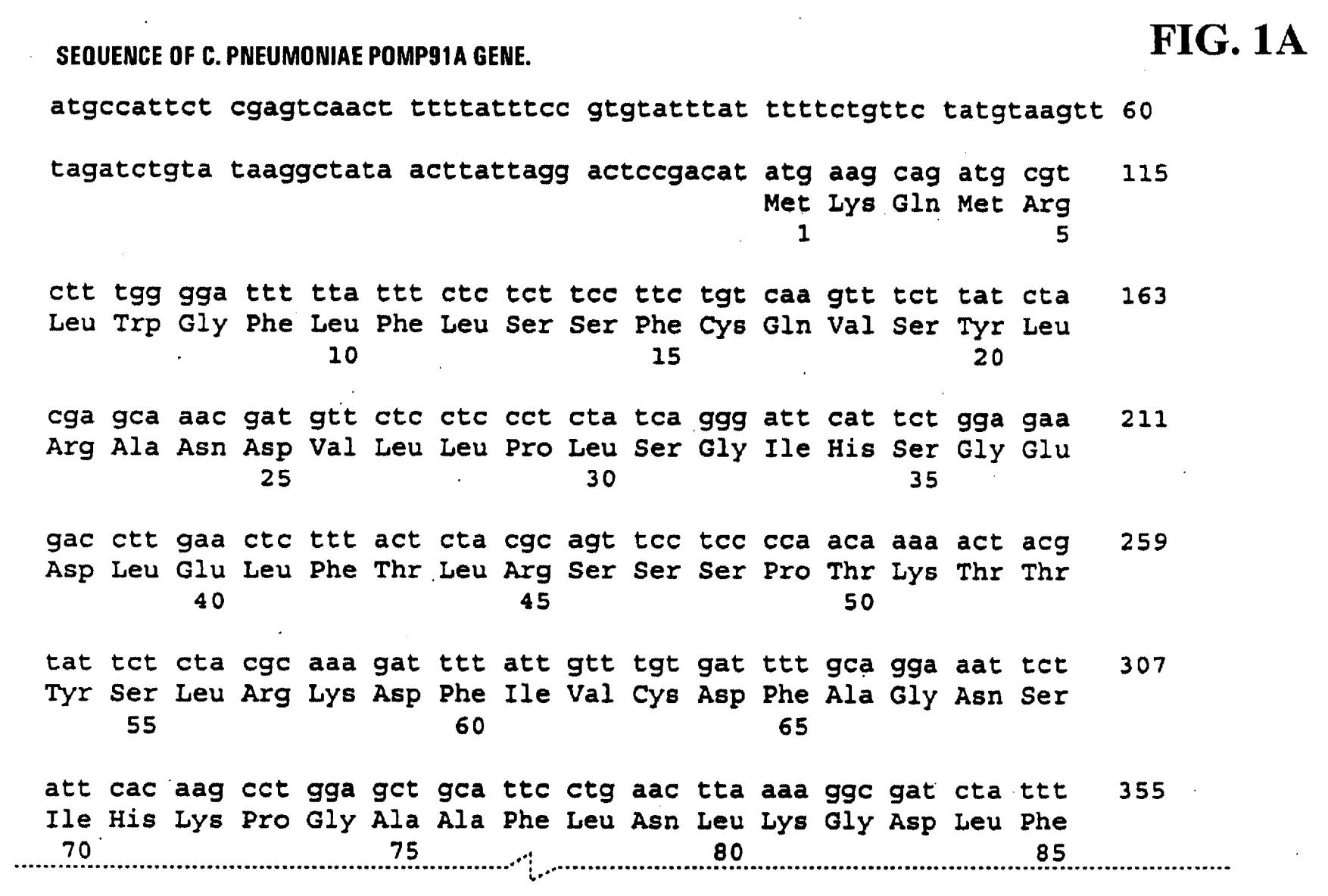

SEQUENCE OF C. PNEUMONIAE POMP91A GENE.

```
atgccattct cgagtcaact ttttatttcc gtgtatttat ttttctgttc tatgtaagtt 60

tagatctgta taaggctata acttattagg actccgacat atg aag cag atg cgt   115
                                            Met Lys Gln Met Arg
                                             1               5

ctt tgg gga ttt tta ttt ctc tct tcc ttc tgt caa gtt tct tat cta   163
Leu Trp Gly Phe Leu Phe Leu Ser Ser Phe Cys Gln Val Ser Tyr Leu
                 10                  15                  20

cga gca aac gat gtt ctc ctc cct cta tca ggg att cat tct gga gaa   211
Arg Ala Asn Asp Val Leu Leu Pro Leu Ser Gly Ile His Ser Gly Glu
             25                  30                  35

gac ctt gaa ctc ttt act cta cgc agt tcc tcc cca aca aaa act acg   259
Asp Leu Glu Leu Phe Thr Leu Arg Ser Ser Ser Pro Thr Lys Thr Thr
         40                  45                  50

tat tct cta cgc aaa gat ttt att gtt tgt gat ttt gca gga aat tct   307
Tyr Ser Leu Arg Lys Asp Phe Ile Val Cys Asp Phe Ala Gly Asn Ser
     55                  60                  65

att cac aag cct gga gct gca ttc ctg aac tta aaa ggc gat cta ttt   355
Ile His Lys Pro Gly Ala Ala Phe Leu Asn Leu Lys Gly Asp Leu Phe
 70                  75                  80                  85
```

FIG. 1B

```
ttt ata aat agc act ccc cta gcg gct ctt acc ttt aaa aac att cac     403
Phe Ile Asn Ser Thr Pro Leu Ala Ala Leu Thr Phe Lys Asn Ile His
                 90                  95                  100

tta gga gct cgc ggt gct ggg ctc ttc tcg gaa tcc aat gtg acc ttc     451
Leu Gly Ala Arg Gly Ala Gly Leu Phe Ser Glu Ser Asn Val Thr Phe
            105                 110                 115

aaa ggc ctg cac tct ctc gtt ctc gaa aac aac gaa agt tgg gga ggc     499
Lys Gly Leu His Ser Leu Val Leu Glu Asn Asn Glu Ser Trp Gly Gly
        120                 125                 130

gtc ctc acc aca tct ggc gac ctt tcc ttc ata aat aat acc agt gtg     547
Val Leu Thr Thr Ser Gly Asp Leu Ser Phe Ile Asn Asn Thr Ser Val
    135                 140                 145

ctt tgt caa aac aac att agc tat gga cct gga gga gcg cta ctc tta     595
Leu Cys Gln Asn Asn Ile Ser Tyr Gly Pro Gly Gly Ala Leu Leu Leu
150                 155                 160                 165

caa gga aga aaa agc aag gct ctc ttt ttc aga gac aat cga gga aca     643
Gln Gly Arg Lys Ser Lys Ala Leu Phe Phe Arg Asp Asn Arg Gly Thr
                170                 175                 180

att cta ttt ctg aaa aac aaa gcc gtg aat caa gat gaa tcc cat cct     691
Ile Leu Phe Leu Lys Asn Lys Ala Val Asn Gln Asp Glu Ser His Pro
            185                 190                 195
```

FIG. 1C

```
ggg tac gga gga gct gta agt agt ata agt cct ggc tcc ccg att acc    739
Gly Tyr Gly Gly Ala Val Ser Ser Ile Ser Pro Gly Ser Pro Ile Thr
        200                 205                 210

ttc gct gac aac caa gaa atc cta ttc caa gag aat gag ggc gaa ctt    787
Phe Ala Asp Asn Gln Glu Ile Leu Phe Gln Glu Asn Glu Gly Glu Leu
    215                 220                 225

ggt gga gcc att tat aac gat cag ggt gcc ata act ttt gag aat aac    835
Gly Gly Ala Ile Tyr Asn Asp Gln Gly Ala Ile Thr Phe Glu Asn Asn
230                 235                 240                 245

ttt caa acc aca agc ttt ttc tct aac aaa gct agt ttc gag gag ctg    883
Phe Gln Thr Thr Ser Phe Phe Ser Asn Lys Ala Ser Phe Glu Glu Leu
                250                 255                 260

tct ata gcc gct act gca atc tct att cac agt ggg gcg ata ccc tat    931
Ser Ile Ala Ala Thr Ala Ile Ser Ile His Ser Gly Ala Ile Pro Tyr
            265                 270                 275

tca cta aaa acg ctg ctg caa aag tta ggc gga gcc atc cat gcg gat    979
Ser Leu Lys Thr Leu Leu Gln Lys Leu Gly Gly Ala Ile His Ala Asp
        280                 285                 290

tat gtt cat ata aga gac tgt aaa gga agc atc gtc ttt gag gag aac    1027
Tyr Val His Ile Arg Asp Cys Lys Gly Ser Ile Val Phe Glu Glu Asn
    295                 300                 305
```

FIG. 1D

```
tca gca aca gct gga ggg gca atc gca gta aat gca gtt tgt gac att   1075
Ser Ala Thr Ala Gly Gly Ala Ile Ala Val Asn Ala Val Cys Asp Ile
310                 315                 320                 325

aat gct caa ggt cct gtt cgc ttt ata aat aac tct gcg tta gga cta   1123
Asn Ala Gln Gly Pro Val Arg Phe Ile Asn Asn Ser Ala Leu Gly Leu
                330                 335                 340

aat ggt ggt gct att tat atg cag gct act gga tct ata ttg cgc tta   1171
Asn Gly Gly Ala Ile Tyr Met Gln Ala Thr Gly Ser Ile Leu Arg Leu
            345                 350                 355

cat gca aat caa gga gat att gaa ttt tgt gga aat aaa gta cga tcg   1219
His Ala Asn Gln Gly Asp Ile Glu Phe Cys Gly Asn Lys Val Arg Ser
        360                 365                 370

cag ttt cat tca cat ata aat tcc act tca aac ttc aca aat aat gcc   1267
Gln Phe His Ser His Ile Asn Ser Thr Ser Asn Phe Thr Asn Asn Ala
    375                 380                 385

att act atc caa gga gcg cct cga gaa ttt tcg ctc agc gcg aat gaa   1315
Ile Thr Ile Gln Gly Ala Pro Arg Glu Phe Ser Leu Ser Ala Asn Glu
390                 395                 400                 405

gga cat cgc atc tgt ttc tat gat cct ata att tct gca aca gaa aac   1363
Gly His Arg Ile Cys Phe Tyr Asp Pro Ile Ile Ser Ala Thr Glu Asn
                410                 415                 420
```

FIG. 1E

```
tat aac tct ctg tac atc aac cat cag aga ctt tta gaa gcc ggg ggt    1411
Tyr Asn Ser Leu Tyr Ile Asn His Gln Arg Leu Leu Glu Ala Gly Gly
            425                 430                 435

gct gtg atc ttt tca gga gca cgc cta tct cca gag cat aaa aaa gaa    1459
Ala Val Ile Phe Ser Gly Ala Arg Leu Ser Pro Glu His Lys Lys Glu
        440                 445                 450

aat aag aac aaa act tcg att ata aac cag ccc gta cgt ctc tgt tct    1507
Asn Lys Asn Lys Thr Ser Ile Ile Asn Gln Pro Val Arg Leu Cys Ser
    455                 460                 465

gga gtc ctt tct ata gaa ggg ggc gcg att ctt gct gtt cgt tct ttt    1555
Gly Val Leu Ser Ile Glu Gly Gly Ala Ile Leu Ala Val Arg Ser Phe
470                 475                 480                 485

tat caa gaa gga ggt ctt ctt gct ctc ggg cca ggt tct aaa ctg acc    1603
Tyr Gln Glu Gly Gly Leu Leu Ala Leu Gly Pro Gly Ser Lys Leu Thr
                490                 495                 500

act caa ggg aaa aat tct gaa aaa gat aaa att gtc atc aca aat tta    1651
Thr Gln Gly Lys Asn Ser Glu Lys Asp Lys Ile Val Ile Thr Asn Leu
            505                 510                 515

gga ttc aac cta gaa aat cta gac tct tcg gat cct gca gaa atc cga    1699
Gly Phe Asn Leu Glu Asn Leu Asp Ser Ser Asp Pro Ala Glu Ile Arg
        520                 525                 530
```

FIG. 1F

```
gct aca gaa aaa gcc tct att gaa att tct gga gtt cct aga gtc tat   1747
Ala Thr Glu Lys Ala Ser Ile Glu Ile Ser Gly Val Pro Arg Val Tyr
    535                 540                 545

ggt cac aca gaa tct ttc tat gaa aat cat gag tat gcc tcc aaa cct   1795
Gly His Thr Glu Ser Phe Tyr Glu Asn His Glu Tyr Ala Ser Lys Pro
550                 555                 560                 565

tat aca act tcg att att cta tct gcc aaa aaa ctt gtt aca gct ccc   1843
Tyr Thr Thr Ser Ile Ile Leu Ser Ala Lys Lys Leu Val Thr Ala Pro
                570                 575                 580

tct agg cca gag aaa gac atc caa aat ctc atc atc gct gaa tct gag   1891
Ser Arg Pro Glu Lys Asp Ile Gln Asn Leu Ile Ile Ala Glu Ser Glu
            585                 590                 595

tat atg ggc tac ggc tat caa ggc tca tgg gaa ttc tcc tgg tct cct   1939
Tyr Met Gly Tyr Gly Tyr Gln Gly Ser Trp Glu Phe Ser Trp Ser Pro
        600                 605                 610

aac gac act aaa gaa aag aaa acc att ata gcc tct tgg act cct aca   1987
Asn Asp Thr Lys Glu Lys Lys Thr Ile Ile Ala Ser Trp Thr Pro Thr
    615                 620                 625

gga gaa ttt tct tta gat ccg aag cgc cgt gga tct ttc att ccc aca   2035
Gly Glu Phe Ser Leu Asp Pro Lys Arg Arg Gly Ser Phe Ile Pro Thr
630                 635                 640                 645
```

FIG. 1G

```
acc tta tgg tcg aca ttc tct ggg ctg aat ata gca tcg aat atc gtg    2083
Thr Leu Trp Ser Thr Phe Ser Gly Leu Asn Ile Ala Ser Asn Ile Val
                650                 655                 660

aat aac aat tac ctc aac aac tcc gag gtc atc ccc ctg caa cat ctc    2131
Asn Asn Asn Tyr Leu Asn Asn Ser Glu Val Ile Pro Leu Gln His Leu
            665                 670                 675

tgt gtt ttt gga ggc cct gtc tat cag att atg gag caa aat cct aaa    2179
Cys Val Phe Gly Gly Pro Val Tyr Gln Ile Met Glu Gln Asn Pro Lys
        680                 685                 690

cag agc tct aac aat ctc tta gtt caa cat gcg ggt cat aat gtt gga    2227
Gln Ser Ser Asn Asn Leu Leu Val Gln His Ala Gly His Asn Val Gly
    695                 700                 705

gct aga att cct ttc tct ttc aat acc ata ttg agt gct gca ctt act    2275
Ala Arg Ile Pro Phe Ser Phe Asn Thr Ile Leu Ser Ala Ala Leu Thr
710                 715                 720                 725

caa ctc ttc tct tct tca tca caa caa aat gtt gct gat aag agc cac    2323
Gln Leu Phe Ser Ser Ser Ser Gln Gln Asn Val Ala Asp Lys Ser His
                730                 735                 740

gcg caa ata ttg ata ggg act gta tct ctt aat aaa agt tgg caa gca    2371
Ala Gln Ile Leu Ile Gly Thr Val Ser Leu Asn Lys Ser Trp Gln Ala
            745                 750                 755
```

FIG. 1H

```
cta tct ctt aga tct tca ttt agc tat acg gaa gac tct cag gta atg   2419
Leu Ser Leu Arg Ser Ser Phe Ser Tyr Thr Glu Asp Ser Gln Val Met
        760                 765                 770

aag cac gta ttc ccc tat aaa ggg acc tct cga gga tct tgg aga aac   2467
Lys His Val Phe Pro Tyr Lys Gly Thr Ser Arg Gly Ser Trp Arg Asn
    775                 780                 785

tac gga tgg tcc gga tct gtc ggc atg tct tac gcc tat cct aaa gga   2515
Tyr Gly Trp Ser Gly Ser Val Gly Met Ser Tyr Ala Tyr Pro Lys Gly
790                 795                 800                 805

atc cgc tat cta aag atg act ccc ttt gtt gac ctt cag tat aca aag   2563
Ile Arg Tyr Leu Lys Met Thr Pro Phe Val Asp Leu Gln Tyr Thr Lys
                810                 815                 820

tta gta caa aat ccc ttt gtg gaa acg ggt tat gac cct aga tat ttt   2611
Leu Val Gln Asn Pro Phe Val Glu Thr Gly Tyr Asp Pro Arg Tyr Phe
            825                 830                 835

tct tcc tcg gag atg acg aac cta tct cta ccg ata ggt atc gct tta   2659
Ser Ser Ser Glu Met Thr Asn Leu Ser Leu Pro Ile Gly Ile Ala Leu
        840                 845                 850

gaa atg cgc ttt ata ggc tcg cgt tct tcc cta ttt ctc caa gtc agc   2707
Glu Met Arg Phe Ile Gly Ser Arg Ser Ser Leu Phe Leu Gln Val Ser
    855                 860                 865
```

FIG. 1I

```
acc tcg tac att aaa gac tta cgt cgg gtc aac cca caa tct tca gct    2755
Thr Ser Tyr Ile Lys Asp Leu Arg Arg Val Asn Pro Gln Ser Ser Ala
870                 875                 880                 885

tcc ttg gtg tta aat cac tac acg tgg gat atc caa gga gtc cct cta    2803
Ser Leu Val Leu Asn His Tyr Thr Trp Asp Ile Gln Gly Val Pro Leu
                890                 895                 900

ggg aaa gaa gct cta aac att acc tta aat agc acg att aag tac aag    2851
Gly Lys Glu Ala Leu Asn Ile Thr Leu Asn Ser Thr Ile Lys Tyr Lys
            905                 910                 915

att gtg act gcc tat atg ggg att tct agc acc caa cga gaa ggc agt    2899
Ile Val Thr Ala Tyr Met Gly Ile Ser Ser Thr Gln Arg Glu Gly Ser
        920                 925                 930

aac ctt tcg gca aat gct cat gca ggc ctc tcc ctt agt ttc            2941
Asn Leu Ser Ala Asn Ala His Ala Gly Leu Ser Leu Ser Phe
    935                 940                 945

tagaagttag cactatagaa ataaaagaag acttaaaaag cgcgtggtta tcattcaaac 3001

acgcgctttt ttatcccttg cctaatttat ccatctgatt tatctatca              3050
```

RESTRICTION ENZYME ANALYSIS OF THE C. PNEUMONIAE POMP91A GENE

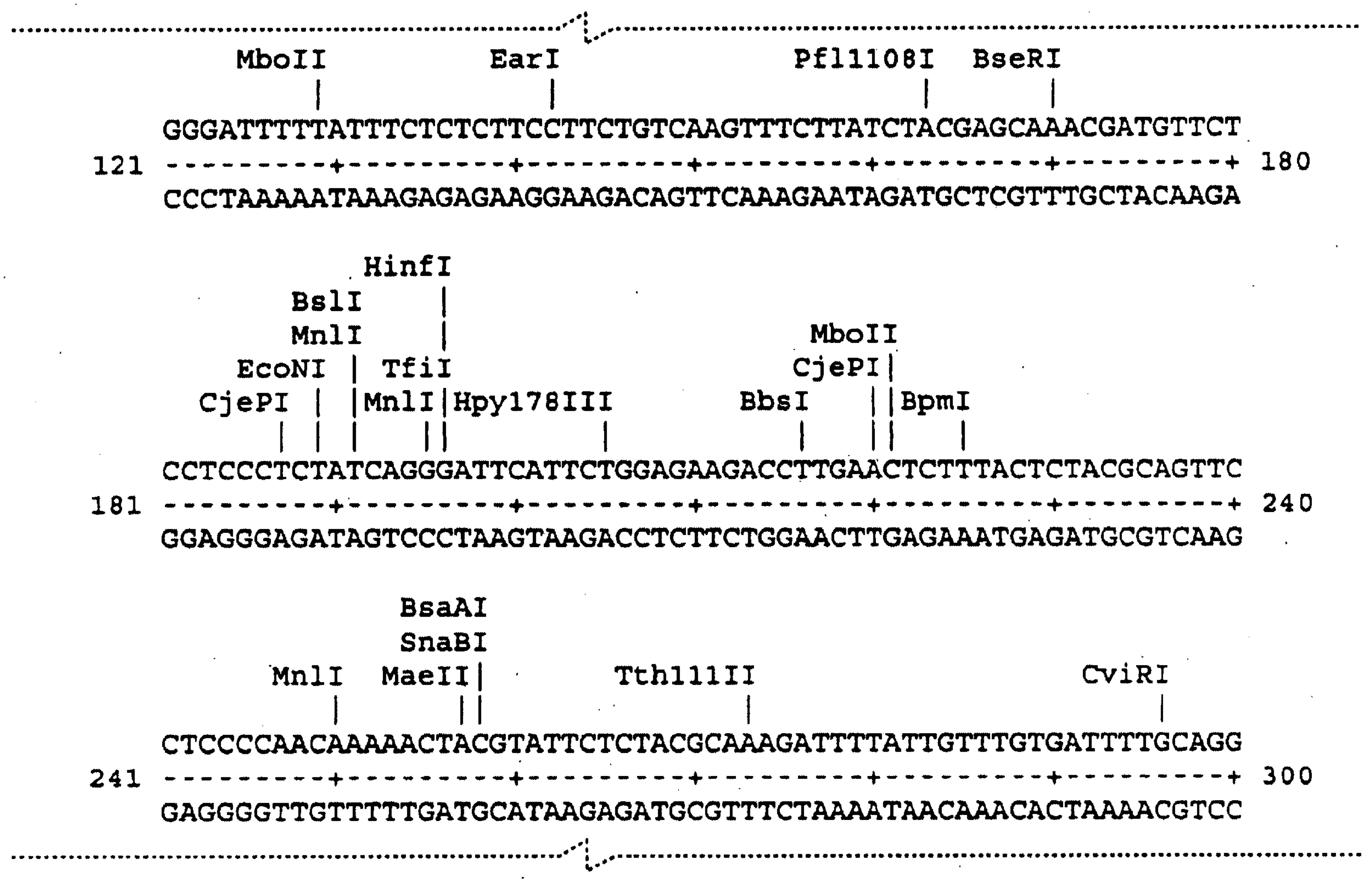

FIG. 2B

```
              MboII        EarI            Pfl1108I   BseRI
               —            —                 —        —
      GGGATTTTTATTCTCTCTTCCTTCTGTCAAGTTTCTTATCGAGCAAACGATGTTCT
121   ------+---------+---------+---------+---------+---------+  180
      CCCTAAAAATAAGAGAGAAGGAAGACAGTTCAAAGAATAGCTCGTTTGCTACAAGA

              HinfI
               —                                     MboII
         BslI                                        CjePI
         MnlI                                 BbsI  ||BpmI
      EcoNI —                                  —     ——
      CjePI||MnlI|Hpy178III
       —   —— ——
      CCTCCCTCTATCAGGGATTCATTCTGGAGAAGACCTTGAACTCTTTACTCTACGCAGTTC
181   ------+---------+---------+---------+---------+---------+  240
      GGAGGGAGATAGTCCCTAAGTAAGACCTCTTCTGGAACTTGAGAAATGAGATGCGTCAAG

           BsaAI
           SnaBI
      MnlI MaeII          Tth111II                 CviRI
       —    ——              —                       —
      CTCCCCCAACAAAAACTACGTATTCTCTACGCAAAGATTTTATTGTTGTGATTTTGCAGG
241   ------+---------+---------+---------+---------+---------+  300
      GAGGGGGTTGTTTTTGATGCATAAGAGATGCGTTTCTAAAATAACAACACTAAAACGTCC
```

FIG. 2C

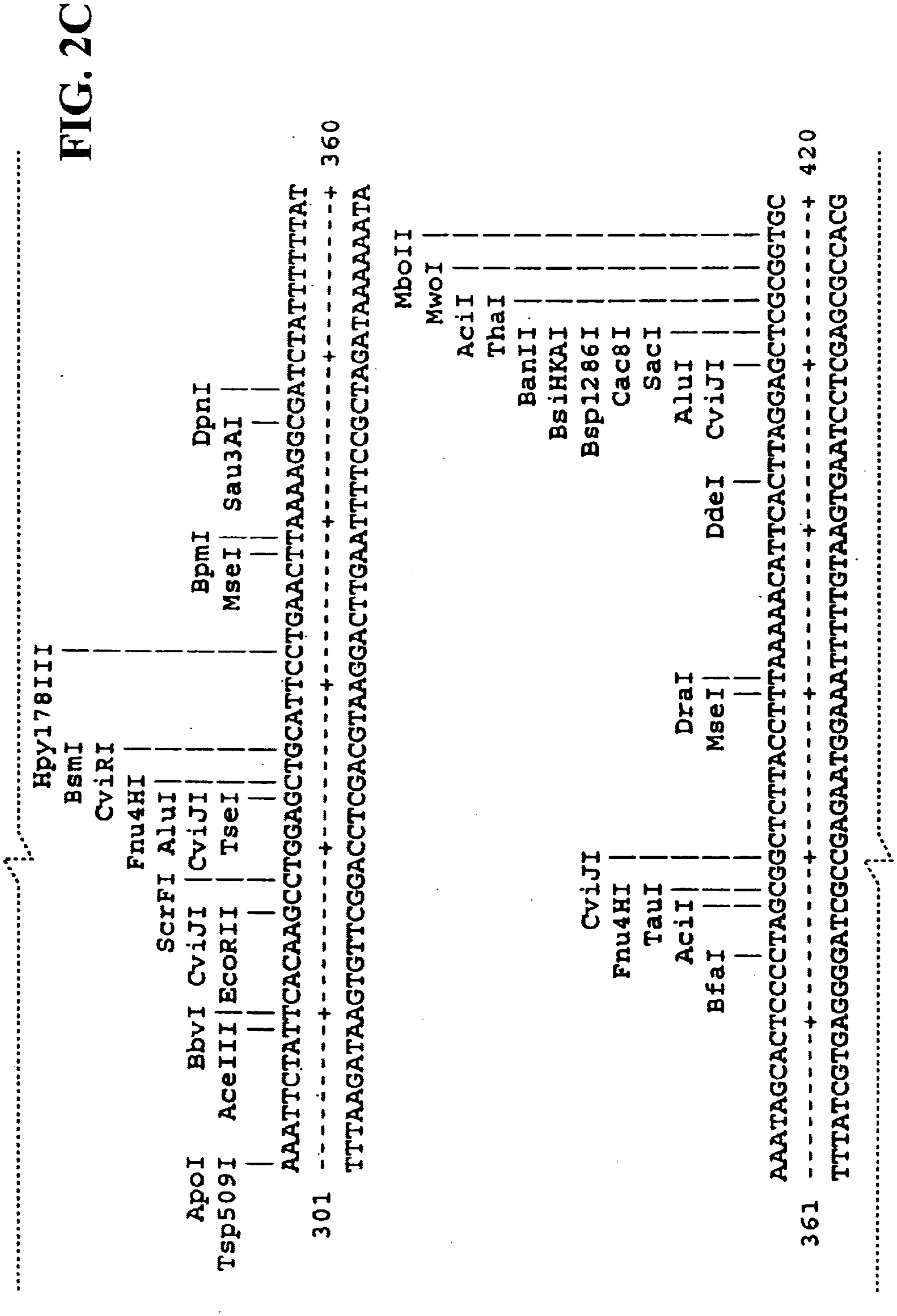

```
                       Hpy178III
                       BsmI
                       CviRI
                  Fnu4HI
                  ScrFI AluI                       BpmI    DpnI
        BbvI CviJI |CviJI                          MseI|  Sau3AI
  ApoI  AceIII|EcoRII| TseI
  Tsp509I   |    |  |   |                            |    |
       AAATTCTATTCACAAGCCTGGAGCTGCATTCCTGAACTTAAAAGGCGATCTATTTTTAT
  301  ----+----+----+----+----+----+----+----+----+----+----+----+ 360
       TTTAAGATAAGTGTTCGGACCTCGACGTAAGGACTTGAATTTTCCGCTAGATAAAAATA

                                                          MboII
                                                          MwoI
                                                          AciI
                                                          ThaI
                                                          BanII
                                                          BsiHKAI
                                                          Bsp1286I
                                                          Cac8I
                                                          SacI
                                     DraI                 AluI
        CviJI                        MseI              DdeI CviJI
        Fnu4HI                         |                  |   |
        TauI
        AciI
        BfaI
       AAATAGCACTCCCCCTAGCGGCTCTTACCTTTAAAAACATTCACTTAGGAGCTCGCGGTGC
  361  ----+----+----+----+----+----+----+----+----+----+----+----+ 420
       TTTATCGTGAGGGGATCGCCGAGAATGGAAATTTTGTAAGTGAATCCTCGAGCGCCACG
```

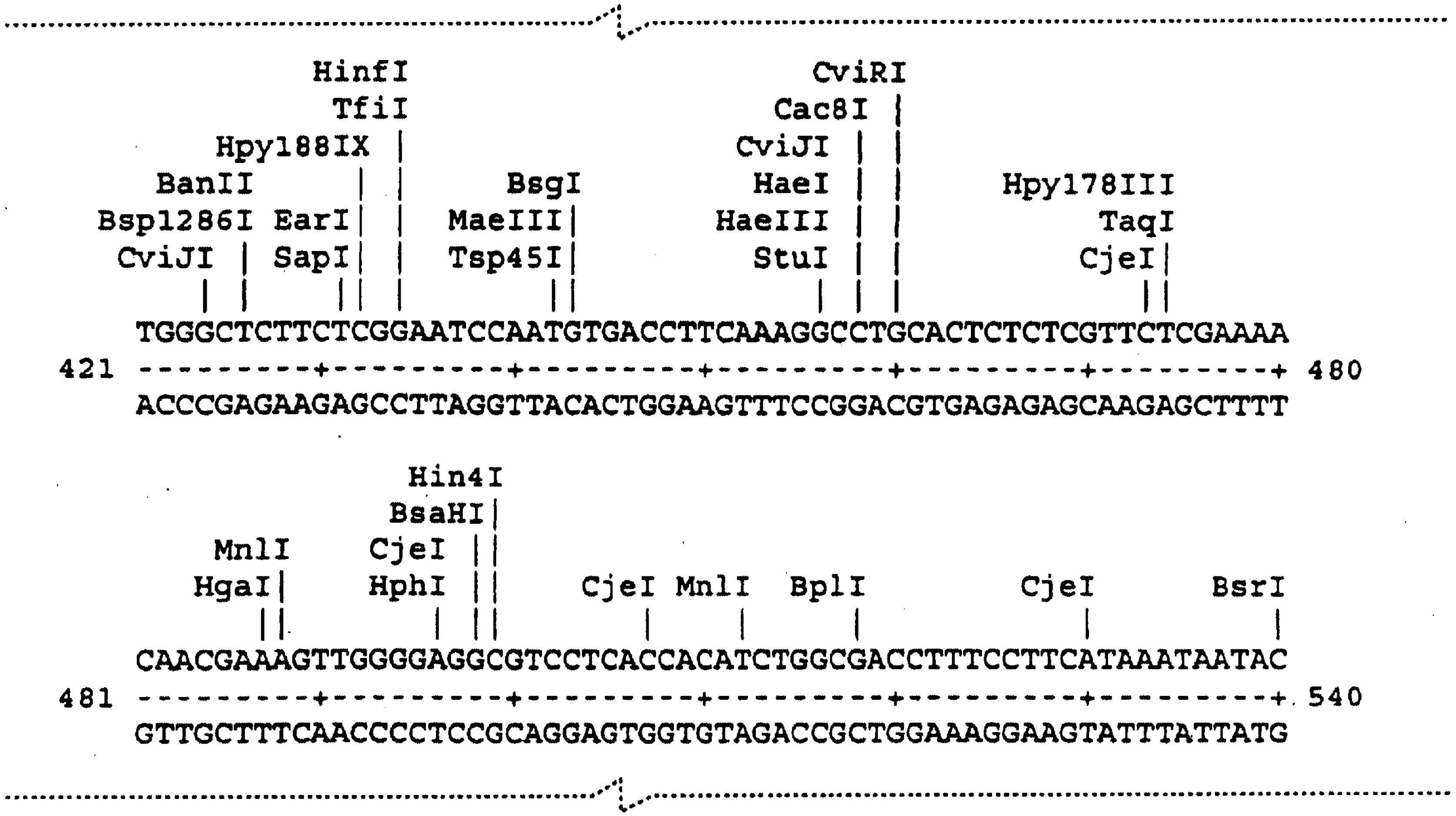

FIG. 2D

```
                                                        HinfI
                                                         TfiI                          Hpy178III
                        Hpy188IX                                              CviRI     TaqI
              BanII             BsgI                                           Cac8I     CjeI
  Bsp1286I EarI                  MaeIII                                         CviJI
     CviJI | SapI                  Tsp45I              HaeI       HaeIII    StuI

        TGGGCTCTTCTCGGAATCCAATGTGACCTTCAAAGGCCTGCACTCTCTCGTTCTCGAAAA
  421   ---------+---------+---------+---------+---------+---------+ 480
        ACCCGAGAAGAGCCTTAGGTTACACTGGAAGTTTCCGGACGTGAGAGAGCAAGAGCTTTT

                 Hin4I
                  BsaHI
           MnlI    CjeI                      CjeI MnlI BplI          CjeI      BsrI
            HgaI    HphI

        CAACGAAAAGTTGGGGAGGCGTCCTCACCACATCTGGCGACCTTTCCTTCATAAATAATAC
  481   ---------+---------+---------+---------+---------+---------+ 540
        GTTGCTTTTCAACCCCTCCGCAGGAGTGGTGTAGACCGCTGGAAAGGAAGTATTTATTATG
```

FIG. 2F

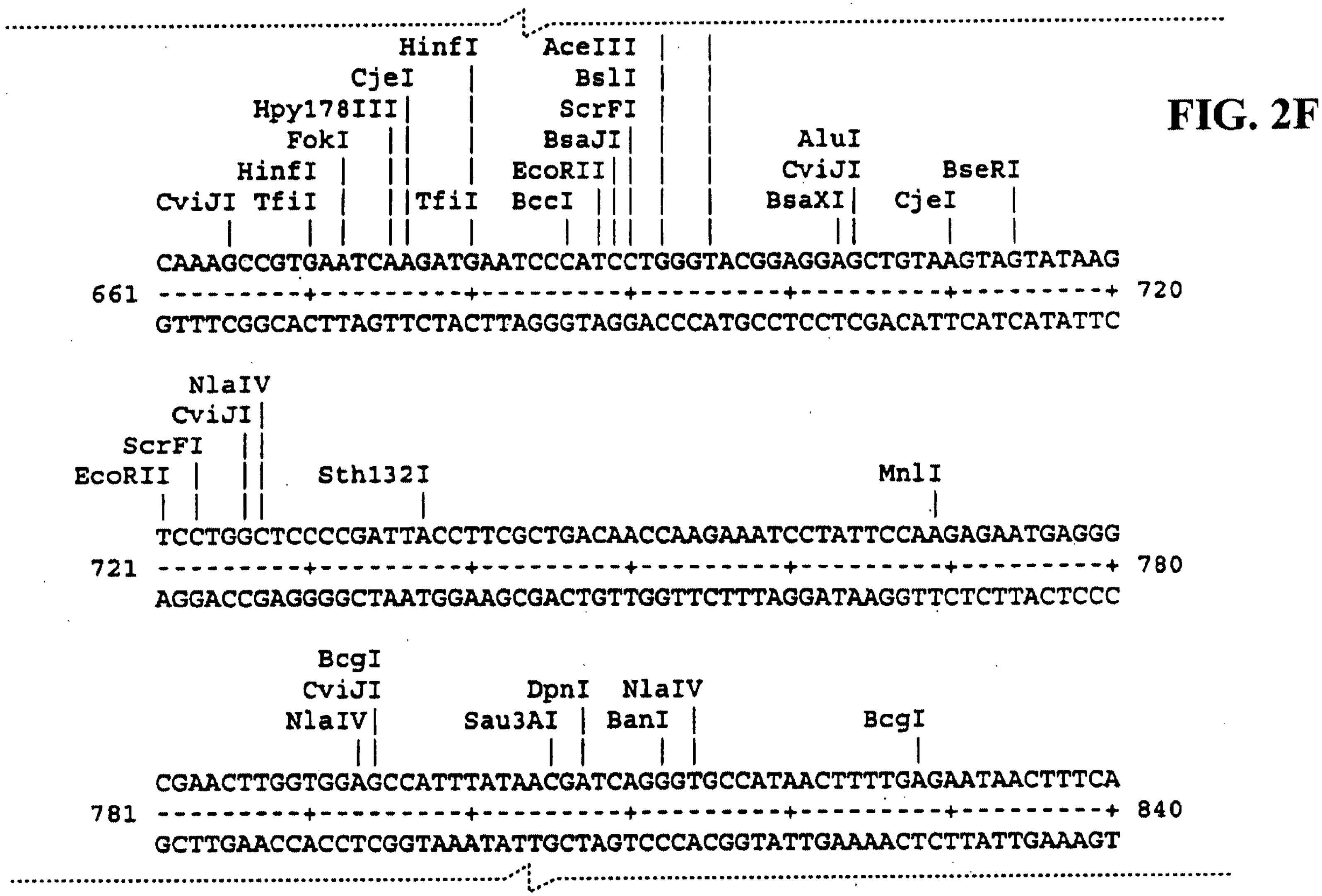

```
              HinfI    AceIII
              CjeI     BslI
         Hpy178III     ScrFI                   AluI
              FokI     BsaJI                   CviJI    BseRI
              HinfI  | EcoRII                  BsaXI|   CjeI
     CviJI Tfil| |TfiI  BccI|                      |     |
     CAAAGCCGTGAATCAAGATGAATCCATCCTGGGTACGGAGGAGCTGTAAGTAGTATAAG
661 ----+----+----+----+----+----+----+----+----+----+----+----+ 720
     GTTTCGGCACTTAGTTCTACTTAGGTAGGACCCATGCCTCCTCGACATTCATCATATTC

     NlaIV
     CviJI
     ScrFI
     EcoRII     Sth132I                                    MnlI
         |         |                                         |
     TCCTGGCTCCCCCGATTACCTTCGCTGACAACCAAGAAATCCTATTCCAAGAGAATGAGG
721 ----+----+----+----+----+----+----+----+----+----+----+----+ 780
     AGGACCGAGGGGCTAATGGAAGCGACTGTTGGTTCTTTAGGATAAGGTTCTCTTACTCCC

     BcgI
     CviJI     DpnI  NlaIV
     NlaIV     Sau3AI| BanI                            BcgI
         |         |  |                                  |
     CGAACTTGGTGGAGCCATTTATAACGATCAGGGTGCCATAACTTTGAGAATAACTTTCA
781 ----+----+----+----+----+----+----+----+----+----+----+----+ 840
     GCTTGAACCACCTCGGTAAATATTGCTAGTCCCACGGTATTGAAAACTCTTATTGAAAGT
```

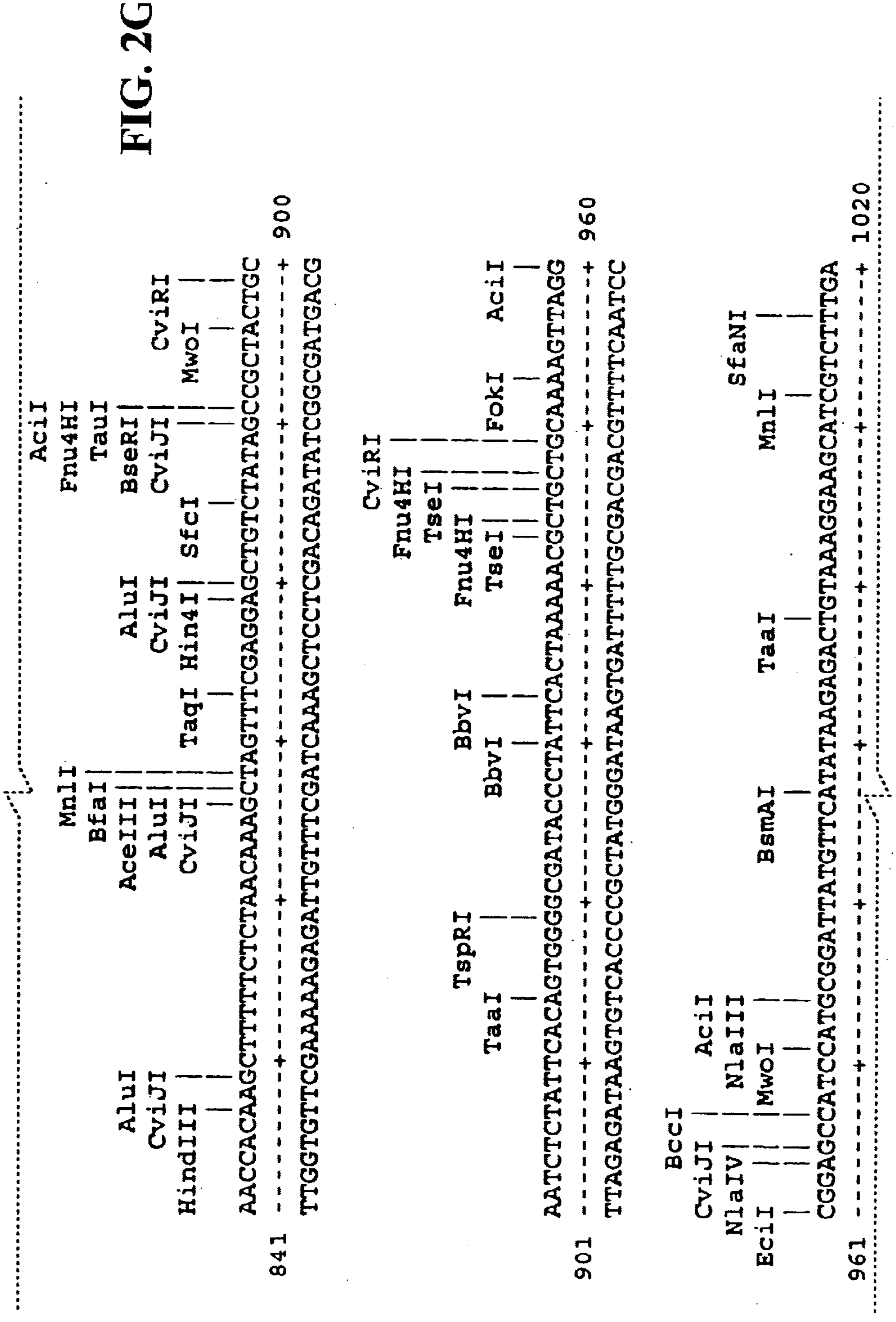

FIG. 2G

```
        AluI                    MnlI
        CviJI                   BfaI            AciI
        HindIII                 AceIII          Fnu4HI
                                AluI            TauI
                   AluI         CviJI           BseRI
                   CviJI        TaqI Hin4I|SfcI CviJI  MwoI  CviRI

     AACCACAAGCTTTTCTCTAACAAAGCTAGTTTCGAGGAGCTGTCTATAGCCGCTACTGC
841  -----+---------+---------+---------+---------+---------+   900
     TTGGTGTTCGAAAAGAGATTGTTTCGATCAAAGCTCCTCGACAGATATCGGCGATGACG

                                          CviRI
                                          Fnu4HI
                           BbvI           TseI
                TspRI      BbvI           Fnu4HI   TseI    FokI   AciI

     AATCTCTATTCACAGTGGGGCGATACCCTATTCACTAAAACGCTGCTGCAAAAGTTAGG
901  -----+---------+---------+---------+---------+---------+   960
     TTAGAGATAAGTGTCACCCCGCTATGGGATAAGTGATTTTGCGACGACGTTTTCAATCC

        TaaI                      BsmAI        TaaI            SfaNI
     BccI                                                       MnlI
     CviJI   AciI
     NlaIV|  NlaIII
     EciI | MwoI
     CGGAGCCATCCATGCGGATTATGTTCATATAAGAGACTGTAAAGGAAGCATCGTCTTTGA
961  -----+---------+---------+---------+---------+---------+   1020
```

FIG. 2H

```
GCCTCGGTAGGTACGCCTAATACAAGTATATTCTCTGACATTTCCTTCGTAGCAGAAACT

                     Hin4I
                    MwoI |
                   BplI| |
                BseMII|| |                             MaeIII
              AluI   ||| |                             Tsp45I
             CviJI   ||| |                          Bce83I |
            MspA1I   ||| |                      CviRI     | |
             PvuII   ||| |                    BpmI |      | |
      DdeI  BseRI  | ||| |                 BstAPI| |      | |      MseI
 Hin4I  |   MnlI   | ||| |                  MwoI|| |      | |      VspI  SmlI
     |  |      |   | ||| |                     || |      | |         |     |
   GGAGAACTCAGCAACAGCTGGAGGGGCAATCGCAGTAAATGCAGTTTGTGACATTAATGC
1021 ---------+---------+---------+---------+---------+---------+ 1080
   CCTCTTGAGTCGTTGTCGACCTCCCCGTTAGCGTCATTTACGTCAAACACTGTAATTACG

   AvaII
 EcoO109I
   Psp5II
   Sau96I
 Sse8647I
       |
   TCAAGGTCCTGTTCGCTTTATAAATAACTCTGCGTTAGGACTAAATGGTGGTGCTATTTA
1081 ---------+---------+---------+---------+---------+---------+ 1140
   AGTTCCAGGACAAGCGAAATATTTATTGAGACGCAATCCTGATTTACCACCACGATAAAT
```

FIG. 2I

```
                      BsrI
           CviJI      DpnI                        CviRI
         Cac8I | BstYI |                         NlaIII                ApoI
       CviRI | |Sau3AI |   AlwI HhaI               NspI              Tsp509I
           | | |     | |      |    |                 |                   |
        TATGCAGGCTACTGGATCTATATTGCGCTTACATGCAAATCAAGGAGATATTGAATTTTG
   1141 ---------+---------+---------+---------+---------+---------+ 1200
        ATACGTCCGATGACCTAGATATAACGCGAATGTACGTTTAGTTCCTCTATAACTTAAAAC

                      BsiEI
                       PvuI
                      DpnI|
                  Sau3AI ||                     ApoI
                  RsaI | ||                  Tsp509I
                     | | ||                        |
        TGGAAATAAAGTACGATCGCAGTTTCATTCACATATAAATTCCACTTCAAACTTCACAAA
   1201 ---------+---------+---------+---------+---------+---------+ 1260
        ACCTTTATTTCATGCTAGCGTCAAAGTAAGTGTATATTTAAGGTGAAGTTTGAAGTGTTT

                                ApoI
                             Tsp509I
                         Hpy178III |
                              TaqI | |
                             AvaI| | |
                             SmlI| | |
                             XhoI| | |
                BsaJI       HaeII|| | | Bpu1102I  HhaI
                 StyI       HhaI||| | |MnlI DdeI  ThaI    BseMII
                    |          |||| | |  |    |     |        |
        TAATGCCATTACTATCCAAGGAGCGCCTCGAGAATTTTCGCTCAGCGCGAATGAAGGACA
   1261 ---------+---------+---------+---------+---------+---------+ 1320
        ATTACGGTAATGATAGGTTCCTCGCGGAGCTCTTAAAAGCGAGTCGCGCTTACTTCCTGT

                  Tsp509I
```

FIG. 2K

```
Hpy178III  TaqI  CviJI  BscGI  SunI  RsaI  MaeII  Sth132I
     TCCAGAGCATAAAAAAGAAAATAAGAACAAAACTTCGATTATAAACCAGCCCGTACGTCT
1441 ---------+---------+---------+---------+---------+---------+ 1500
     AGGTCTCGTATTTTTTCTTTTATTCTTGTTTTGAAGCTAATATTTGGTCGGGCATGCAGA

BsmBI  BsmAI  Hpy178III  HinfI  PleI  SfcI  BpmI  ThaI  HhaI  TfiI  HinfI  MwoI  MnlI  Hpy178III
     CTGTTCTGGAGTCCTTTCTATAGAAGGGGGCGCGATTCTTGCTGTTCGTTCTTTTTATCA
1501 ---------+---------+---------+---------+---------+---------+ 1560
     GACAAGACCTCAGGAAAGATATCTTCCCCCGCGCTAAGAACGACAAGCAAGAAAAATAGT

MboII  BbsI  Sth132I  AvaI  Sau96I  HaeIII  EcoRII  CviJI  ScrFI  Bce83I  SmlI  BslI  Tsp509I  ApoI  Hpy188IX
     AGAAGGAGGTCTTCTTGCTCTCGGGCCAGGTTCTAAACTGACCACTCAAGGGAAAAATTC
1561 ---------+---------+---------+---------+---------+---------+ 1620
     TCTTCCTCCAGAAGAACGAGAGCCCGGTCCAAGATTTGACTGGTGAGTTCCCTTTTTAAG
```

FIG. 2M

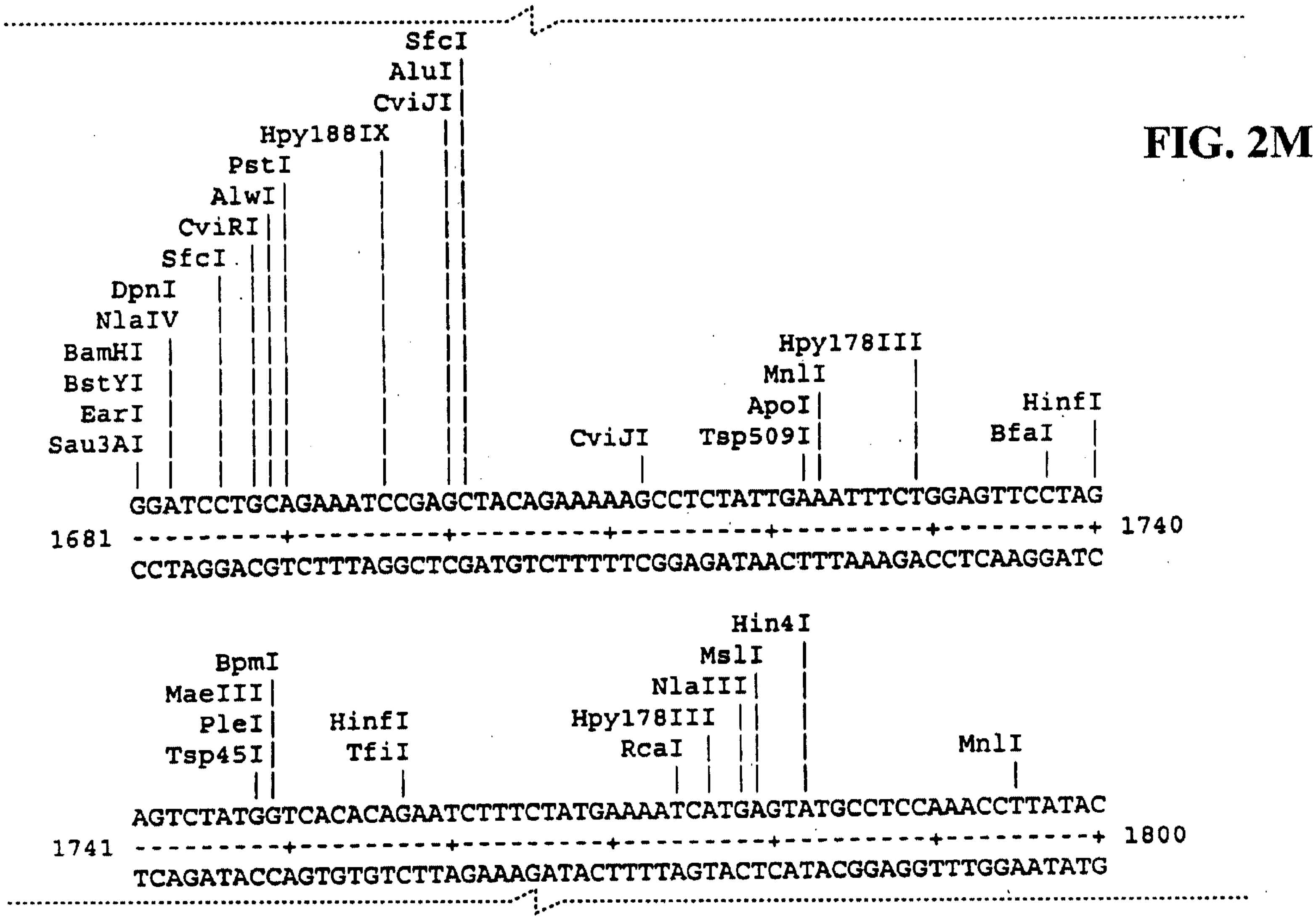

```
             SfcI|
             AluI|
             CviJI|
         Hpy188IX|                              Hpy178III|
             PstI|                                   MnlI|
             AlwI|                          CviJI  ApoI|  Tsp509I|         HinfI|
            CviRI|                             |       |       |              BfaI|
             SfcI|                             |       |       |                 |
             DpnI|                             |       |       |                 |
            NlaIV|                             |       |       |                 |
            BamHI|                                                                                    1740
            BstYI|                                                                                      |
             EarI|                                                                                      |
           Sau3AI|                                                                                      |
     GGATCCTGCAGAAAATCCGAGCTACAGAAAAAGCCTCTATTGAAATTTCTGGAGTTCCTAG
1681 -----+---------+---------+---------+---------+---------+---- 1740
     CCTAGGACGTCTTTTAGGCTCGATGTCTTTTTCGGAGATAACTTTAAAGACCTCAAGGATC

                                          Hin4I|
                                          MslI|
            BpmI|                    NlaIII|
           MaeIII|                 Hpy178III|
            PleI|    HinfI|            RcaI|                            MnlI|
           Tsp45I|   TfiI|               |                                 |
     AGTCTATGGTCACACAGATCTTTCTATGAAAATCATGAGTATGCCTCCAAACCTTATAC
1741 -----+---------+---------+---------+---------+---------+---- 1800
     TCAGATACCAGTGTCTCTTAGAAAGATACTTTTAGTACTCATACGGAGGTTTGGAATATG
```

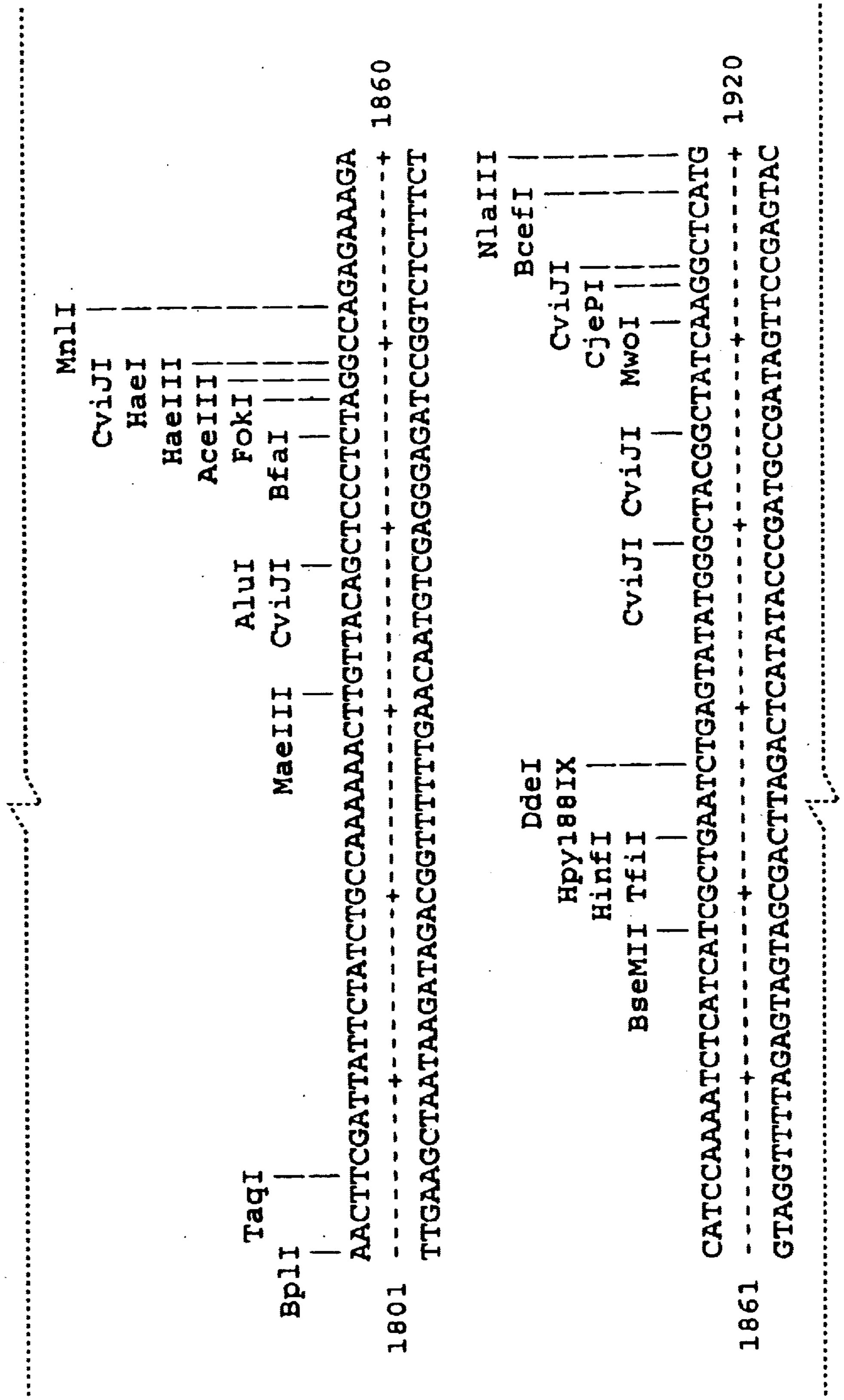

FIG. 2N

```
                                     MnlI
                               CviJI  |
                               |  HaeI
                               |  |  HaeIII
                               |  |  |  AceIII
                               |  |  |  |  FokI
                Alul  CviJI    |  |  |  |  |  BfaI
        MaeIII  |     |        |  |  |  |  |  |
Bpll    |       |     |        |  |  |  |  |  |
TaqI  | |       |     |        |  |  |  |  |  |
|     | |       |     |        |  |  |  |  |  |
AACTTCGATTATTCTATCTGCCAAAAAACTTGTTACAGCTCCCTCTAGGCCAGAGAAAGA
1801 ----+----+----+----+----+----+ 1860
TTGAAGCTAATAAGATAGACGGTTTTTTGAACAATGTCGAGGGAGATCCGGTCTCTTTCT
                                                         NlaIII
                                                         |  BcefI
                                                         |  |
                                                         |  |  CviJI
                                                         |  |  |  CjePI
                                                         |  |  |  |  MwoI
                         DdeI              CviJI CviJI   |  |  |  |  |
                         |  Hpy188IX       |     |       |  |  |  |  |
                         |  |  HinfI       |     |       |  |  |  |  |
                         |  |  |  TfiI     |     |       |  |  |  |  |
                         |  |  |  |        |     |       |  |  |  |  |
                    BseMII |  |  |  |      |     |       |  |  |  |  |
                    |    | |  |  |  |      |     |       |  |  |  |  |
CATCCAAAATCTCATCATCGCTGAATCTGAGTATATGGGCTACGGCTATCAAGGCTCATG
1861 ----+----+----+----+----+----+ 1920
GTAGGTTTTAGAGTAGTAGCGACTTAGACTCATATACCCGATGCCGATAGTTCCGAGTAC
```

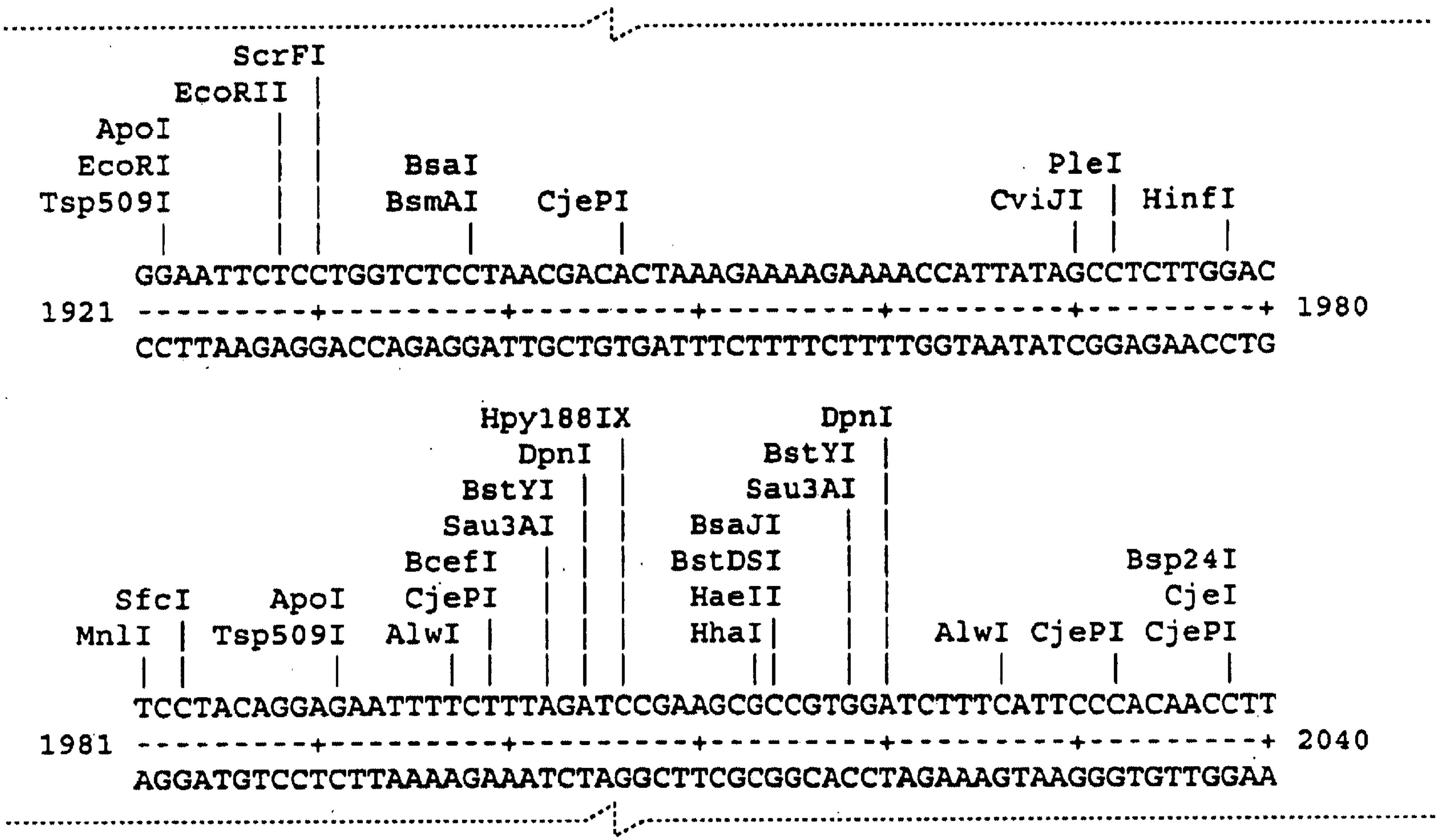

FIG. 2O

```
          ScrFI
         EcoRII                                                              PleI
     ApoI  |    BsaI                                                    CviJI | HinfI
    EcoRI  |   BsmAI    CjePI                                              |  |
   Tsp509I |    |  |     |                                                 |  |
    |   |  |    |  |     |
   GGAATTCTCCTGGTCTCCTAACGACACTAAAGAAAAGAAAACCATTATAGCCTCTTGGAC
1921 ---+---------+---------+---------+---------+---------+ 1980
   CCTTAAGAGGACCAGAGGATTGCTGTGATTTCTTTTCTTTTGGTAATATCGGAGAACCTG

                   Hpy188IX          DpnI
                      |             BstYI
                     DpnI           Sau3AI
                    BstYI            BsaJI
                    Sau3AI           BstDSI
                     BcefI           HaeII                         Bsp24I
           SfcI      CjePI           HhaI                           CjeI
         ApoI|       AlwI             |                 AlwI CjePI CjePI
     MnlI|Tsp509I|    |                |                   |   |    |
       |  |  |        |                |                   |   |    |
   TCCTACAGGAGAATTTCTTTAGATCCTTCGGATCTTCATTCCCACAACCTT
1981 ---+---------+---------+---------+---------+---------+ 2040
   AGGATGTCCTCTTAAAAGAAATCTAGGCTTCGGGCACCTAGAAAGTAAGGGTGTTGGAA
```

```
       RleAI
     HincII|
      AccI||                     CjeI
      TaqI||                     TaqI
      TaqI||                   CjePI|Hpy178III
     SalI|||       CviJI     Bsp24I|| SfaNI  | Tsp509I      FokI
        ||||           |          |||     |  |       |         |
     ATGGTCGACATTCTCTGGGCTGAATATAGCATCGAATATCGTGAATAACAATTACCTCAA
2041 ---------+---------+---------+---------+---------+---------+ 2100
     TACCAGCTGTAAGAGACCCGACTTATATCGTAGCTTATAGCACTTATTGTTAATGGAGTT

                                              BsaXI
                                              Hin4I
      BsaJI                                  CviJI|
   Hpy188IX                                 HaeIII|
      MnlI|                              EcoO109I||
  MnlI   ||           CviRI    MslI MnlI  Sau96I|||  Hpy188IX
     |   ||               |       |    |        |||         |
     CAACTCCGAGGTCATCCCCCTGCAACATCTCTGTGTTTTTGGAGGCCCTGTCTATCAGAT
2101 ---------+---------+---------+---------+---------+---------+ 2160
     GTTGAGGCTCCAGTAGGGGGACGTTGTAGAGACACAAAAACCTCCGGGACAGATAGTCTA
```

FIG. 2P

```
                        BanII
                       BsiHKAI
                      Bsp1286I
                         SacI                Faul       SimI
                        AluI |               MmeI   AciI  |
                       CviJI |         Sth132I| NlaIII    |
                             |     DdeI      ||   NspI    |
                           | |        |      ||      |    |
     TATGGAGCAAAATCCTAAACAGAGCTCTAACAATCTCTTAGTTCAACATGCGGGTCATAA
2161 ---------+---------+---------+---------+---------+---------+ 2220
     ATACCTCGTTTTAGGATTTGTCTCGAGATTGTTAGAGAATCAAGTTGTACGCCCAGTATT

             ApoI
            EcoRI
          Tsp509I                                              MboII
           BfaI |                              CviRI        CjeI |
          AluI| |                  BbvI     Fnu4HI |      MboII| |
         CviJI| |         CjeI   BsgI|       TseI| |MboII     || |
```

FIG. 2Q

```
                ||  |           |      ||          || |    |    || |
     TGTTGGAGCTAGAATTCCTTTCTCTTTCAATACCATATTGAGTGCTGCACTTACTCAACT
2221 ---------+---------+---------+---------+---------+---------+ 2280
     ACAACCTCGATCTTAAGGAAAGAGAAAGTTATGGTATAACTCACGACGTGAATGAGTTGA

                                                 HhaI
      EarI EarI                      CviJI ThaI  |  SspI
         |    |                          |    |  |    |
     CTTCTCTTCTTCATCACAACAAAATGTTGCTGATAAGAGCCACGCGCAAATATTGATAGG
2281 ---------+---------+---------+---------+---------+---------+ 2340
     GAAGAGAAGAAGTAGTGTTGTTTTACAACGACTATTCTCGGTGCGCGTTTATAACTATCC

                                             DpnI
                                      Tth111II|
                                         BglII||
                                         BstYI||
                                        Sau3AI||
     Hin4I   BsmFI                     DdeI  |||
     TaaI|   MseI|         Cac8I    MboII |  |||         AluI
                                                         CviJI PleI
        ||      ||             |        |  | |||             |    |
     GACTGTATCTCTTAATAAAAGTTGGCAAGCACTATCTCTTAGATCTTCATTTAGCTATAC
2341 ---------+---------+---------+---------+---------+---------+ 2400
     CTGACATAGAGAATTATTTTCAACCGTTCGTGATAGAGAATCTAGAAGTAAATCGATATG
```

FIG. 2R

```
                                                         CjeI
                                                         BsmFI|
                                                         DpnI|
                                                         MnlI|
                                                     BstYI|
                                                     Sau3AI|
                                            Hpy178III
                                            MnlI
                                         NlaIV
                                         AvaII
                                       EcoO109I
                                       Psp5II   TaqI
                                       Sau96I|  |AvaI
                                        BslI|   |SmlI
                                        BslI|   ||XhoI
                    BsaAI
                    MaeII|
                    BseMII|
    BbsI
    DdeI
    |MboII
Hinfl
2401 GGAAGACTCTCAGGTAATGAAGCACGTATTCCCCTATAAAGGGACCTCTCGAGGATCTTG
     ------+---------+---------+---------+---------+---------+ 2460
     CCTTCTGAGAGTCCATTACTTCGTGCATAAGGGGATATTTCCCTGGAGAGCTCCTAGAAC
```

FIG. 2T

```
                                  FokI
                                DpnI |
                             BstYI | |
                            Sau3AI | |
                        Hpy178III| | |
                            MspI|| | |
                          BsaWI||| | |
                          BspEI||| | |
                        AvaII |||| | |     NlaIII                        AciI
                       Sau96I |||| | |  CjeI   |                   HinfI   |
    AlwI               BccI|  |||| | |AlwI |NspI                    TfiI   |
     |                    ||  |||| | |   |  |  |                       |   |
     GAGAAACTACGGATGGTCCGGATCTGTCGGCATGTCTTACGCCTATCCTAAAGGAATCCG
2461 ---------+---------+---------+---------+---------+---------+ 2520
     CTCTTTGATGCCTACCAGGCCTAGACAGCCGTACAGAATGCGGATAGGATTTCCTTAGGC

                Eco57I             BstZ17I         RsaI
             PleI HinfI|     HincII    AccI|    TatI |     Sth132I
                |    ||          |        ||       | |           |
     CTATCTAAAGATGACTCCCTTTGTTGACCTTCAGTATACAAAGTTAGTACAAAATCCCTT
2521 ---------+---------+---------+---------+---------+---------+ 2580
     GATAGATTTCTACTGAGGGAAACAACTGGAAGTCATATGTTTCAATCATGTTTTAGGGAA

                           MboII       Hpy188IX
              BscGI  SimI BfaI |       BsaJI |   MnlI
                  |     |    | |           | |      |
     TGTGGAAACGGGTTATGACCCTAGATATTTTTCTTCCTCGGAGATGACGAACCTATCTCT
2581 ---------+---------+---------+---------+---------+---------+ 2640
     ACACCTTTGCCCAATACTGGGATCTATAAAAAGAAGGAGCCTCTACTGCTTGGATAGAGA
```

```
                      MboII          Hpy188IX
        BscGI   SimI BfaI |          BsaJI  |     MnlI
            |      |     |  |              |  |        |
     TGTGGAAACGGGTTATGACCCTAGATATTTTTCTTCCTCGGAGATGACGAACCTATCTCT
2581 ---------+---------+---------+---------+---------+---------+ 2640
     ACACCTTTGCCCAATACTGGGATCTATAAAAAGAAGGAGCCTCTACTGCTTGGATAGAGA

                                       ThaI
                                    Cac8I |
                                  CviJI | |
                                  MboII | |
       BsaBI           HhaI  MwoI     | | |
           |              |     |     | | |
     ACCGATAGGTATCGCTTTAGAAATGCGCTTTATAGGCTCGCGTTCTTCCCTATTTCTCCA
2641 ---------+---------+---------+---------+---------+---------+ 2700
     TGGCTATCCATAGCGAAATCTTTACGCGAAATATCCGAGCGCAAGAAGGGATAAAGAGGT
```

FIG. 2U

```
                        BsmFI
                     BsaAI |
                      PmlI |       BsaJI
     MseI          MaeII|  |        StyI     CjeI BfaI         AluI
 CjeI  |       AflIII  ||  |EcoRV  |HinfI    |  PleI   MnlI   CviJI
   |   |            |  ||  |    |  |    |    |    |      |       |
     GGTGTTAAATCACTACACGTGGGATATCCAAGGAGTCCCTCTAGGGAAAGAAGCTCTAAA
2761 ---------+---------+---------+---------+---------+---------+ 2820
     CCACAATTTAGTGATGTGCACCCTATAGGTTCCTCAGGGAGATCCCTTTCTTCGAGATTT

                             RsaI
                         TatI |  MaeIII
          MseI       MseI  |  |  Tsp45I            BslI     BfaI
           |           |   |  |      |               |        |
     CATTACCTTAAATAGCACGATTAAGTACAAGATTGTGACTGCCTATATGGGATTTCTAG
2821 ---------+---------+---------+---------+---------+---------+ 2880
     GTAATGGAATTTATCGTGCTAATTCATGTTCTAACACTGACGGATATACCCCTAAAGATC
```

```
                                                  CviJI
                                                   HaeI
                                                 HaeIII
                                                   StuI
                                             Cac8I |
            MaeIII                       CviRI   | |       MnlI
             TaqII                      NlaIII   | |    DdeI  |XbaI
                 |                           |   | |       |  |   |
      CACCCAACGAGAAGGCAGTAACCTTTCGGCAAATGCTCATGCAGGCCTCTCCCTTAGTTT
 2881 ---------+---------+---------+---------+---------+---------+ 2940
      GTGGGTTGCTCTTCCGTCATTGGAAAGCCGTTTACGAGTACGTCCGGAGAGGGAATCAAA

                                                  HhaI
Hpy178III                                   BbsI  ThaI
    BfaI|      SfcI                   MseI|MboII  |
       ||         |                      ||    |  |
      CTAGAAGTTAGCACTATAGAAATAAAAGAAGACTTAAAAAGCGCGTGGTTATCATTCAAA
 2941 ---------+---------+---------+---------+---------+---------+ 3000
      GATCTTCAATCGTGATATCTTTATTTTCTTCTGAATTTTTCGCGCACCAATAGTAAGTTT

          Tth111II
       HhaI      |                 Hpy188IX
      ThaI |     |       Tsp509I   BccI  |
         | |     |             |      |  |
      CACGCGCTTTTTTATCCCTTGCCTAATTTATCCATCTGATTTATCTATCA
 3001 ---------+---------+---------+---------+---------+ 3050
      GTGCGCGAAAAAATAGGGAACGGATTAAATAGGTAGACTAAATAGATAGT
```

FROM

NUCLEIC ACID MOLECULES ENCODING POMP91A PROTEIN OF *CHLAMYDIA*

This application claims the benefit of United States Provisional Patent Application Serial No. 60/097,198, filed Aug. 20, 1998.

FIELD OF INVENTION

The present invention relates to Chlamydia antigens and corresponding DNA molecules, which can be used in methods to prevent and treat Chlamydia infection in mammals, such as humans.

BACKGROUND OF THE INVENTION

Chlamydiae are prokaryotes. They exhibit morphologic and structural similarities to gram-negative bacteria including a trilaminar outer membrane, which contains lipopolysaccharide and several membrane proteins that are structurally and functionally analogous to proteins found in E coli. Chlamydiae are differentiated from other bacteria by their morphology and by a unique development cycle. They are obligate intra-cellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

Because chlamydiae are small and multiply only within susceptible cells, they were long thought to be viruses. However, they have many characteristics in common with other bacteria: (1) they contain both DNA and RNA, (2) they divide by binary fission, (3) their cell envelopes resemble those of other gram-negative bacteria, (4) they contain ribosomes similar to those of other bacteria, and (5) they are susceptible to various antibiotics. Chlamydiae can be seen in the light microscope, and the genome is about one-third the size of the *Escherichia coli* genome.

Many different strains of chlamydiae have been isolated from birds, man and other mammals, and these strains can be distinguished on the basis of host range, virulence, pathogenesis, and antigenic composition. There is strong homology of DNA within each species, but surprisingly little between species, suggesting long-standing evolutionary separation.

*C. trachomatis* has a high degree of host specificity, being almost completely limited to man, and causes ocular and genitourinary infections of widely varying severity. In contrast, *C. psittaci* strains are rare in man but are found in a wide range of birds and also in wild, domestic, and laboratory mammals, where they multiply in cells of many organs.

*C. pneumoniae* is a common human pathogen, originally described as the TWAR strain of *Chlamydia psittaci*, but subsequently recognised to be a new species. *C. pneumoniae* is antigenically, genetically and morphologically distinct from other Chlamydia species (*C. trachomatis, C. pecorum* and *C. psittaci*). It shows 10% or less DNA sequence homolgy with either of *C.trachomatis* or *C.psittaci* and so far appears to consist of only a single strain, TWAR.

*C. pneumoniae* is a common cause of community acquired neumonia, only less frequent than *Streptococcus pneumoniae* and *Mycoplasma pneumoniae* (refs. 1, 2—Throughout this application, various references are cited in parentheses to describe more fully the state of the art to which this invention pertains. Full bibliographic information for each citation is found at the end of the specification, immediately preceding the claims. The disclosures of these references are hereby incorporated by reference into the present disclosure). *C. Pneumoniae* can also cause upper respiratory tract symptoms and disease, including bronchitis and sinusitis (refs. 1 to 4). The great majority of the adult population (over 60%) has antibodies to *C. pneumoniae* (ref. 5), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections there is no known bird or animal reservoir. Transmission has not been clearly defined. It may result from direct contact with secretions, from formites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organisms. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/d, for at least 10 to 14 d). A recently developed drug, azithromycin, is highly effective as a single-dose therapy against chlamydial infections.

In most instances, *C. pneumoniae* infection is often mild and without complications, and up to 90% of infections are subacute or unrecognized. Among children in industrialized countries, infections have been thought to be rare up to the age of 5 y, although a recent study (ref. 6) has reported that many children in this age group show PCR evidence of infection despite being seronegative, and estimates a prevalence of 17 to 19% in 2 to 4 y olds. In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 y. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population sero-prevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease (refs. 7 to 11). Moreover, the organisms has been detected in atheromas and fatty streaks of the coronary, carotid, peripheral arteries and aorta (refs. 12 to 16). Viable *C. pneumoniae* has been recovered from the coronary and carotid artery (refs. 17, 18). Furthermore, it has been shown that *C. pneumoniae* can induce changes of atherosclerosis in a rabbit model (ref. 19). Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbations of asthma in adults, and small-scale studies have shown that prolonged antibiotic treatment was effective at greatly reducing the severity of the disease in some individuals (refs. 20 to 25).

In light of these results, a protective vaccine against *C. pneumoniae* infection would be of considerable importance. There is not yet an effective vaccine for any human chlamydial infection. Nevertheless, studies with *C. trachomatis* and *C. psittaci* indicate that this is an attainable goal. For example, mice which have recovered from a lung infection with *C. trachomatis* are protected from infertility induced by a subsequent vaginal challenge (ref. 26). Similarly, sheep immunized with inactivated *C. psittaci* were protected from subsequent chlamydial-induced abortions and stillbirths (ref. 27). Protection from chlamydial infections has been associated with Th1 immune responses, particularly the induction of INFγ-producing CD4+T-cells (ref. 28). The adoptive transfer of CD4+ cell lines or clones to nude or SCID mice conferred protection from challenge or cleared chronic disease (refs. 29, 30), and in vivo depletion of CD4+ T cells exacerbated disease post-challenge (refs. 31, 32). However, the presence of sufficiently high titres of neutralising antibody at mucosal surfaces can also exert a protective effect (ref. 33).

The extent of antigenic variation within the species *C. pneumoniae* is not well characterised. Serovars of *C. trachomatis* are defined on the basis of antigenic variation in MOMP, but published *C. pneumoniae* MOMP gene sequences show no variation between several diverse isolates of the organism (refs. 34 to 36). The gene encoding a 76kDa antigen has been cloned from a single strain of *C. pneumoniae* and the sequence published (ref. 48). An operon encoding the 9kDa and 60kDa cysteine-rich outer membrane protein genes has been described (refs. 49, 50). Many antigens recognised by immune sera to *C. pneumoniae* are conserved across all chlamydiae, but 98kDa, 76 kDa and several other proteins may be *C. pneumoniae*-specific (refs 48, 51, 52, 53). An assessment of the number and relative frequency of any *C.pneumoniae* serotypes, and the defining antigens, is not yet possible. The entire genome sequence of *C. pneumoniae* strain CWL-029 is now known (ref. 54) and as further sequences become available a better understanding of antigenic variation may be gained.

SUMMARY OF THE INVENTION

The present invention provides purified and isolated DNA molecules that encode Chlamydia polypeptides against POMP91A (SEQ ID Nos: 1, 2), which can be used in methods to prevent, treat, and diagnose Chlamydia infection. The encoded polypeptides includes polypeptides having the amino acid sequence shown in SEQ ID No: 3. Those skilled in the art will appreciate that the invention also includes DNA molecules that encode mutants and derivatives of such polypeptides, which result from the addition, deletion, or substitution of non-essential amino acids as described herein. The invention also includes RNA molecules corresponding to the DNA molecules of the invention.

In addition to the DNA and RNA molecules, the invention includes the corresponding polypeptides and monospecific antibodies that specifically bind to such polypeptides.

The present invention has wide application and includes expression cassettes, vectors, and cells transformed or transfected with the polynucleotides of the invention. Accordingly, the present invention provides (i) a method for producing a polypeptide of the invention in a recombinant host system and related expression cassettes, vectors, and transformed or transfected cells; (ii) a live vaccine vector, such as a pox virus, *Salmonella typhimurium*, or Vibrio chloerae vector, containing a polyuncleotide of the invention, such vaccine vectors being useful for, e.g., preventing the treating Chlamydia infection, in combination with a diluent or carrier, and related pharmaceutical compositions and associated therapeutic and/or prophylactic methods; (iii) a therapeutic and/or prophylactic method involving administration of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of Chlamydia in a biological sample, which can involve the use of a DNA or RNA molecule, a monospecific antibody, or a polypeptide of the invention; and (v) a method for purifying a polypeptide of the invention by antibody-based affinity chromatography.

Accordingly, in one aspect of the present invention, there is provided an isolated and purified nucleic acid molecule encoding a POMP91A protein of a strain of Chlamydia or a polypeptide fragment thereof.

The isolated and purified nucleic acid molecule may have a polynucleotide sequence selected from the group consisting of:

(a) a polynucleotide sequence as set forth in FIGS. 1A–1I (SEQ ID Nos: 1, 2) or the complementary polynucleotide sequence thereto, (b) a polynucleotide sequence encoding an amino acid sequence as set forth in FIGS. 1A–1I (SEQ ID No: 3) or the complementary polynucleotide sequence thereto, (c) a polynucleotide sequence encoding a functional POMP91A of a strain of Chlamydia, and (d) a polynucleotide sequence capable hydribidizing under stringent conditions to a polynucleotide sequence (a) or (b).

BRIEF DESCRIPTION OF THE DRAWINGS

The present invention will be further understood from the following description with reference to the drawings, in which:

FIGS. 1A–1I show the nucleotide sequence of the POMP91A gene (SEQ ID No: 1—entire sequence and SEQ ID No: 2—coding sequence) and the deduced amino acid sequence of the POMP91A from *Chlamydia pneumoniae* (SEQ ID No: 3—encoded protein);

GENERAL DESCRIPTION OF INVENTION

Figure 2A:
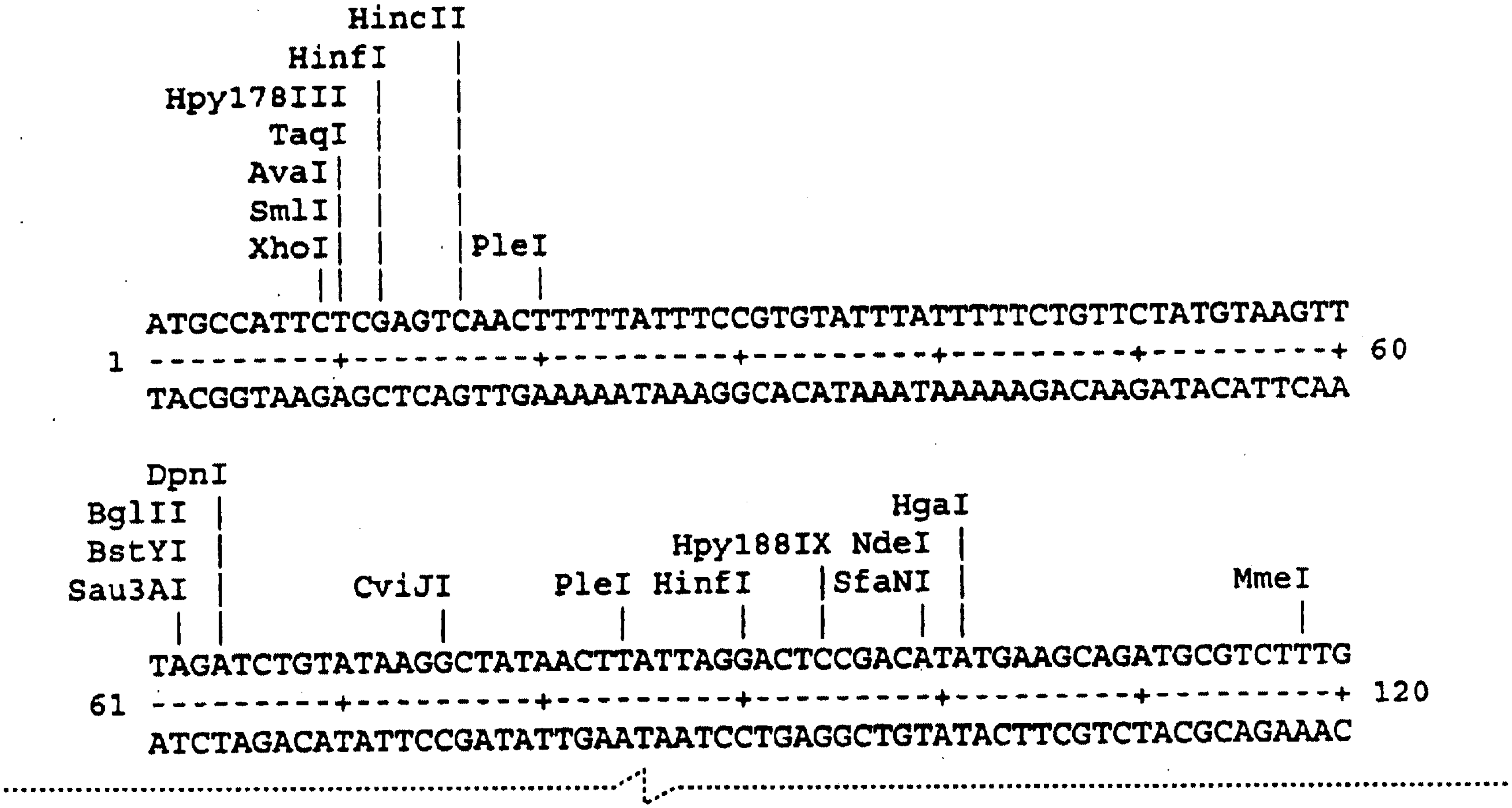
FIGS. 2A–2X show the restriction enzyme analysis of the *C. pneumoniae* POMP91A gene.
Figure 2E:
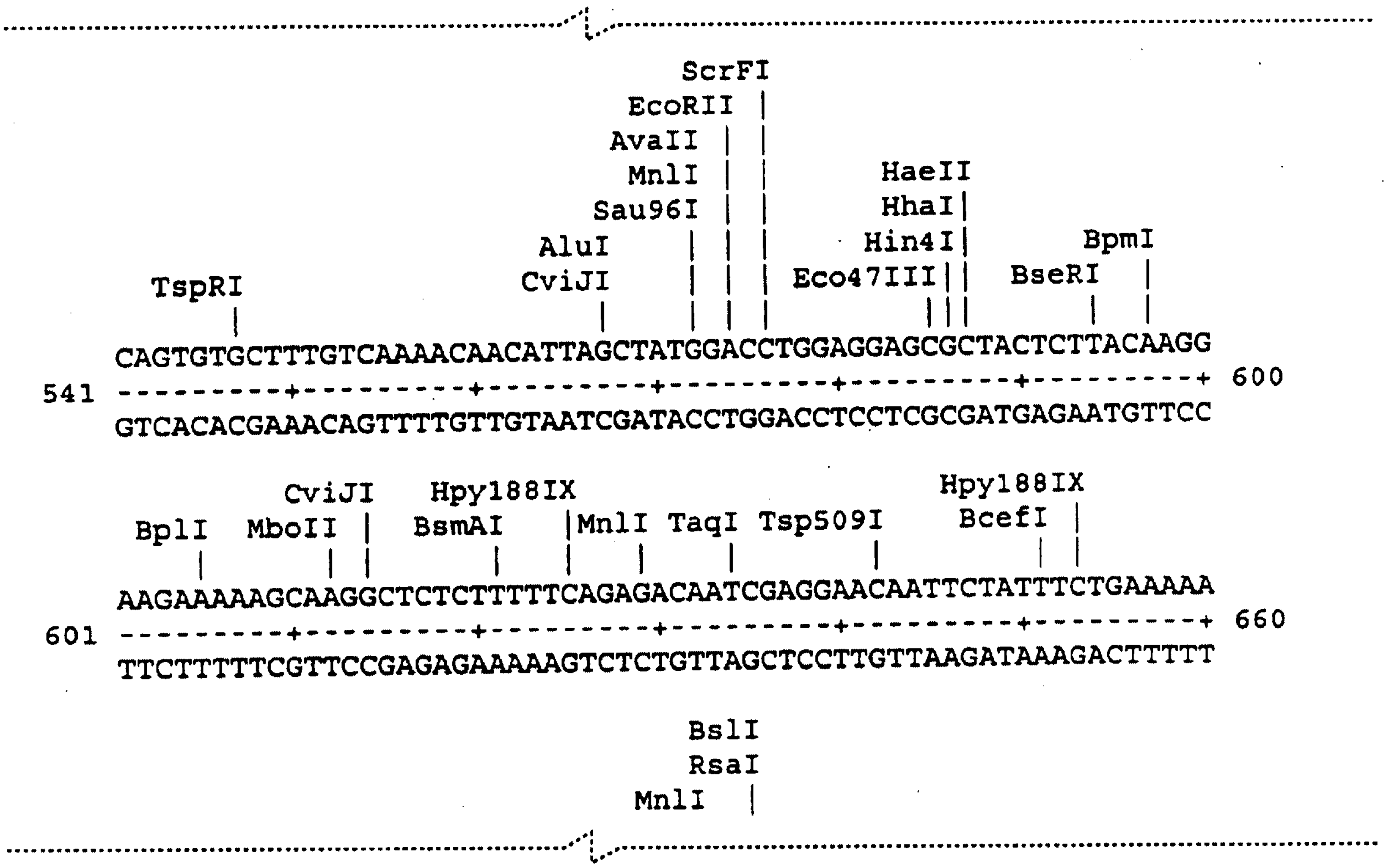
Figure 2J:
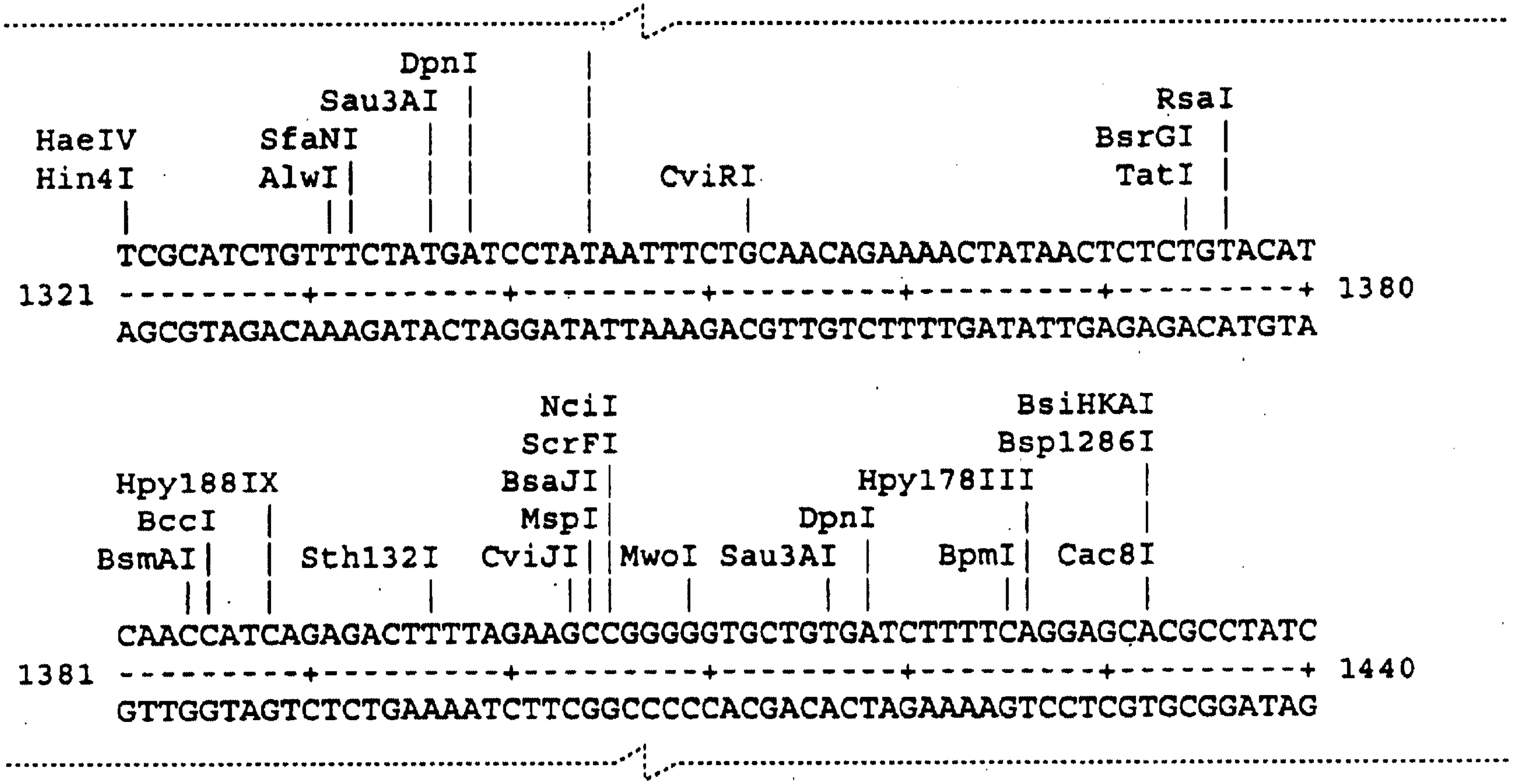
Figure 2L:
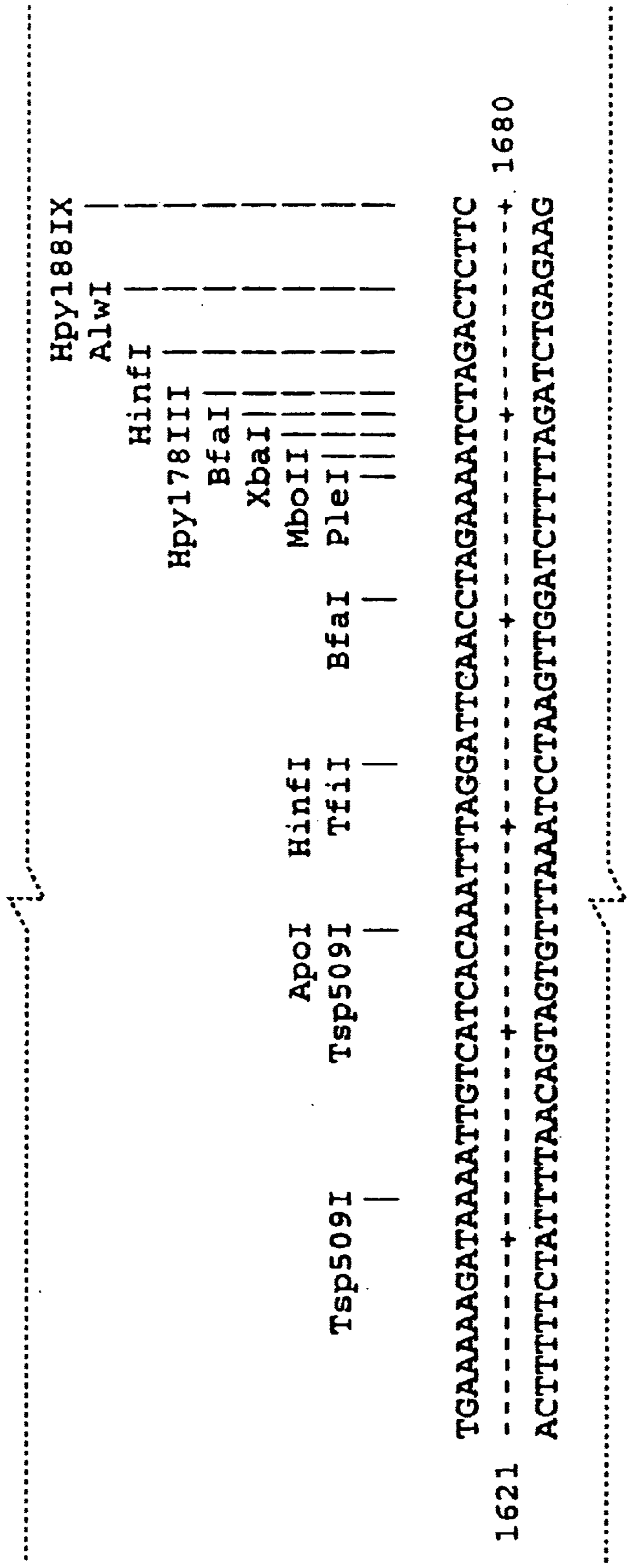
Figure 2S:
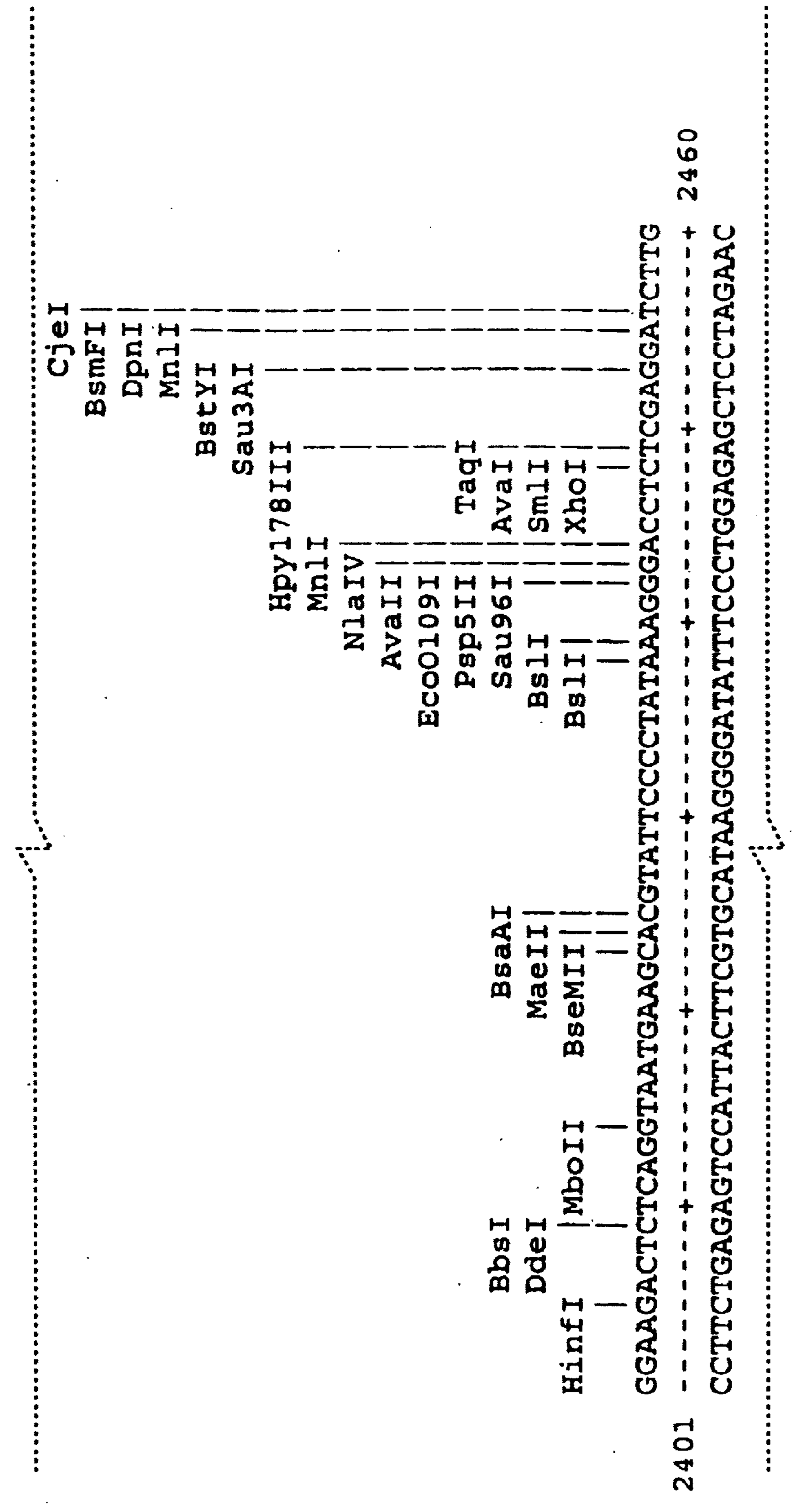
Figure 2V:
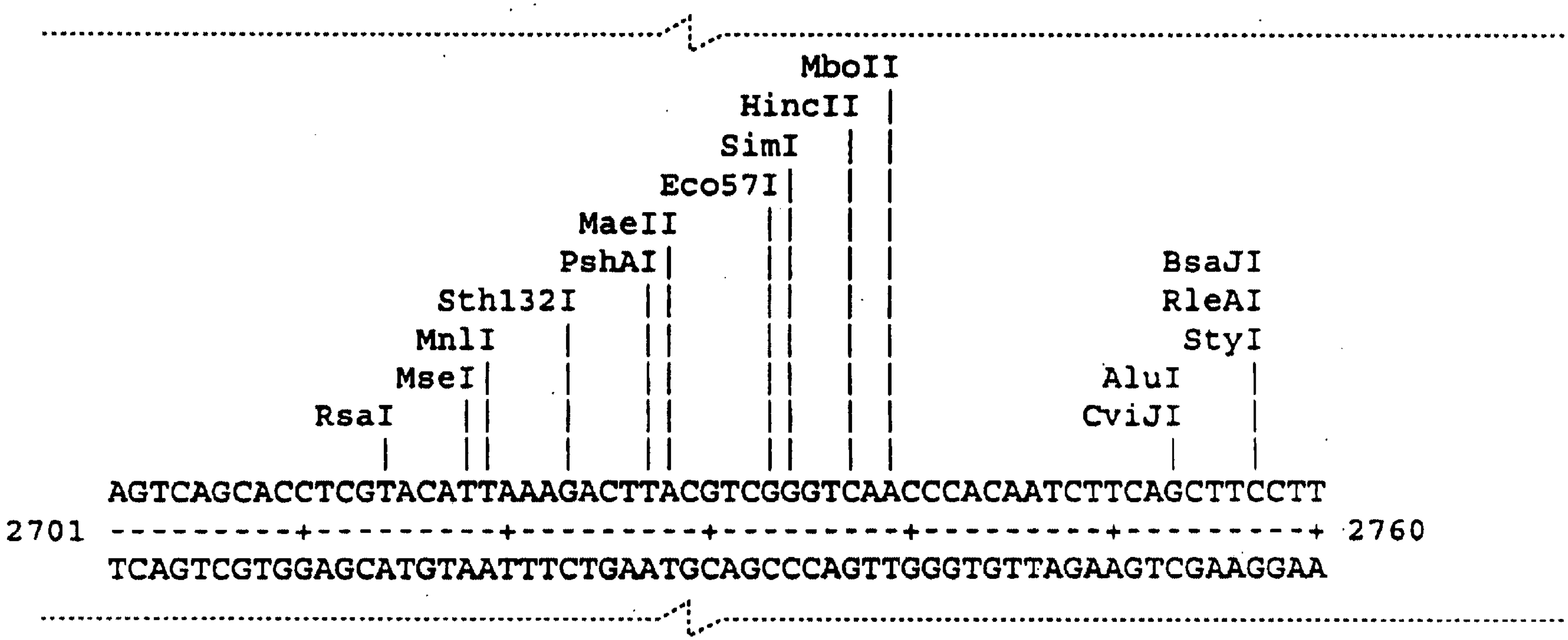

In the *C. pneumoniae* genome, open reading frames (ORFs) encoding chlamydial polypeptides have been identified. These polypeptides include polypeptides permanently found in the bacterial membrane structure, polypeptides that are present in the external vicinity of the bacterial membrane, include polypeptides permanently found in the inclusion membrane structure, polypeptides that are present in the external vicinity of the inclusion membrane, and polypeptides that are released into the cytoplasm of the infected cell. These polypeptides can be used in vaccination methods for preventing and treating Chlamydia infection.

According to an aspect of the invention, there are provided isolated nucleic acid molecules or polynucleotides encoding the precursor and mature forms of Chlamydia polypeptides.

An isolated polynucleotide of the invention encodes (i) a polypeptide having an amino acid sequence that is homologous to a Chlamydia amino acid sequence, the Chlamydia amino acid sequence being:

the amino acid sequence as shown in FIGS. 1A–1I: (SEQ ID No: 3).

the term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' and 3' end, in the naturally occurring genome. Such isolated polynucleotides could be part of a vector or a composition and still be isolated in that such a vector or composition is not part of its natural environment.

A polynucleotide of the invention can be in the form of RNA or DNA (e.g., cDNA, genomic DNA, or synthetic DNA), or modifications or combinations thereof. The DNA can be double-stranded or single-stranded, and, if single-stranded, can be the coding strand or the non-coding (antisense) strand. The sequence that encodes a polypeptide of the invention as shown in SEQ ID Nos: 1 and 2, can be (a) the coding sequence as shown in SEQ ID No: 2 (b) a ribonucleotide sequence derived by transcription of (a); or (c) a different coding sequence; this latter, as a result of the redundancy or degeneracy of the genetic code, encodes the same polypeptides as the DNA molecules of which the nucleotide sequences are illustrated in SEQ ID No: 1 or 2.

By "polypeptides" or "protein" is meant any chain of amino acids, regardless of length or post-translational modification (e.g., glycosylation or phosphorylation). Both terms are used interchangeably in the present application.

By "homologous amino acid sequence" is meant an amino acid sequence that differs from an amino acid sequence shown in SEQ ID No: 3, only by one or more conservative amino acid substitutions, or by one or more non-conservative amino acid substitutions, deletions, or additions located at positions at which they do not destroy the specific antigenicity of the polypeptide.

Preferably, such a sequence is at least 75%, more preferably 80%, and most preferably 90% identical to an amino acid sequence shown in SEQ ID No: 3.

Homologous amino acid sequences include sequences that are identical or substantially identical to an amino acid sequence as shown in SEQ ID No: 3. By "amino acid sequence substantially identical" is meant a sequence that is at least 90%, preferably 95%, more preferably 97%,and most preferably 99% identical to an amino acid sequence of reference and that preferably differs from the sequence of reference, if at all, by a majority of conservative amino acid substitutions.

Conservative amino acid substitutions typically include substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Homology is typically measured using sequence analysis software (e.g., Sequence Analysis Software Package of the Genetics Computer Group, University of Wisconsin Biotechnology Center, 1710 University Avenue, Madison, Wis. 53705). Similar amino acid sequences are aligned to obtain the maximum degree of homology (i.e., identity). To this end, it may be necessary to artificially introduce gaps into the sequence. Once the optimal alignment has been set up, the degree of homology (i.e., identity) is established by recording all of the positions in which the amino acids of both sequences are identical, relative to the total number of positions.

Specifically, sequence alignments were performed using the ALIGN (Trademark) or GENALIGN (Trademark) computer programs (Inteligenetics Suite 5.4, Oxford Molecular). ALIGN® uses the Needleman-Wunsch algorithm (ref. 78) and its later modifications to locate regions of similarity between two sequences. Finding regions of maximum similarity between two sequences can be solved in a rigorous manner using the iterative matrix calculation of the Needleman and Wunsch 1997 algorithm. The analysis is restricted to regions with no internal deletions or insertions, joined by a minimum number of loop-outs or deletions. Sellers (ref. 79) developed a true metric measure of the "distance"

between sequences and Waterman (ref. 80) extended this algorithm to include insertions and deletions of arbitrary length. Smith (ref. 81) improved the early algorithms to find the subsequences of maximum similarity. The algorithm has been used to analyze sequences as long as 5000 bases by dividing these sequences into segments of 200 to 400 bases, and then reassembling them into a final best match. This method of dividing the sequence and then reassembling it has proven quite robust. The algorithm permits the size of the segment to be specified which the program searches for similarities. The program then assembles the segments after checking overlaps of adjacent subsequences.

The weighting of deletions and the relative size of overlaps may be controlled. The program displays the results to show the differences in closely related sequences.

GENALIGN® is a multiple alignment program. Up to 99 sequences using the Martinez/Regions (ref. 82) or Needleman-Wunsch (ref. 78) method may be analyzed for alignment. GENALIGN places the sequences in an order that puts the most closely aligned sequence pairs adjacent to each other. A consensus sequence is displayed under the multiple sequence alignments. The sequences used in developing the consensus sequence file for use in other programs. GENALIGN allows the parameters of the search to be changed so that alternate alignments of the sequences can be formed.

The programs are used employing their default settings. The default settings are as follows:

| | | |
|---|---|---|
| FastDB | | |
| AMINO-Res-length | = | 2 |
| DELetion-weight | = | 5.00 |
| LEngth-factor | = | 0 |
| Matching-weight | = | 1.00 |
| NUCLEIC-Res-length | = | 4 |
| SPread-factor | = | 50 |
| Findseq | | |
| Search Parameters: | | |
| Similarity matrix | | Unitary |
| K-tuple | | 4 |
| Mismatch penalty | | 1 |
| Joining Penalty | | 30 |
| Randomization group length | | 0 |
| Cutoff score | | 5 |
| Alignment Parameters: | | |
| Window size | | 32 |
| Gap penalty | | 1.00 |
| Gap size penalty | | 0.33 |

Homologous polynucleotide sequences are defined in a similar way. Preferably, a homologous sequence is one that is at least 45%, more preferably 60%, and most preferably 85% identical to a coding sequence of SEQ ID Nos: 1 and 2.

Polypeptides having a sequence homologous to one of the sequences shown in SEQ ID No: 3, include naturally-occurring allelic variants, as well as mutants or any other non-naturally occurring variants that are analogous in term of antigenicity, to a polypeptide having a sequence as shown in SEQ ID No: 3.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. The biological function is distinct from the antigenic function. A polypeptide can have more than one biological function.

Allelic variants are very common in nature. For example, a bacterial species, e.g., *C. pneumoniae*, is usually represented by a variety of strains that differ from each other by minor allelic variations. Indeed, a polypeptide that fulfills the same biological function in different strains can have an amino acid sequence that is not identical in each of the strains. Such an allelic variation may be equally reflected at the polynucleotide level.

Support for the use of allelic variants of polypeptide antigens comes from, e.g., studies of the Chlamydial MOMP antigen. The amino acid sequence of the MOMP varies from strain to strain, yet cross-strain antibody binding plus neutralization of infectivity occurs, indicating that the MOMP, when used as an immunogen, is tolerant of amino acid variations.

Polynucleotides, e.g., DNA molecules, encoding allelic variants can easily be retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers can be designed according to the nucleotide sequence information provided in SEQ IN Nos: 1 and 2. Typically, a primer can consist of 10 to 40, preferably 15 to 25 nucleotides. It may be also advantageous to select primers containing C and G nucleotides in a proportion sufficient to ensure efficient hybridization; e.g., an amount of C and G nucleotides of at least 40%, preferably 50% of the total nucleotide amount.

Useful homologs that do not naturally occur can be designed using known methods for identifying regions of an antigen that are likely to be tolerant of amino acid sequence changes and/or deletions. For example, sequences of the antigen from different species can be compared to identify conserved sequences.

Polypeptide derivatives that are encoded by polynucleotides of the invention include, e.g., fragments, polypeptides having large internal deletions derived from full-length polypeptides, and fusion proteins.

Polypeptide fragments of the invention can be derived from a polypeptide having a sequence homologous to SEQ ID No: 3, to the extent that the fragments retain the substantial antigenicity of the parent polypeptide (specific antigenicity). Polypeptide derivatives can also be constructed by large internal deletions that remove a substantial part of the parent polypeptide, while retaining specific antigenicity. Generally, polypeptide derivatives should be about at least 12 amino acids in length to maintain antigenicity. Advantageously, they can be at least 20 amino acids, preferably at least 50 amino acids, more preferably at least 75 amino acids, and most preferably at least 100 amino acids in length.

Useful polypeptide derivatives, e.g., polypeptide fragments, can be designed using computer-assisted analysis of amino acids sequences in order to identify sites in protein antigens having potential as surface-exposed, antigenic regions (ref. 37).

Polypeptide fragments and polypeptides having large internal deletions can be used for revealing epitopes that are otherwise masked in the parent polypeptide and that may be of importance for inducing a protective T cell-dependent immune response. Deletions can also remove immunodominant regions of high variability among strains.

It is an accepted practice in the field of immunology to use fragments and variants of protein immunogens as vaccines as all that is required to induce an immune response to a protein is a small (e.g., 8 to 10 amino acid) immunogenic region of the protein. This has been done for a number of vaccines against pathogens other than Chlamydia. For example, short synthetic peptides corresponding to surface-exposed antigens of pathogens such as murine mammary tumor virus, peptide containing 11 amino acids; (ref. 38), Semliki Forest virus, peptide containing 16 amino acids (ref. 39), and canine parvovirus, 2 overlapping peptides, each containing 15 amino acids (ref. 40), have been shown to be effective vaccine antigens against their respective pathogens.

Polynucleotides encoding polypeptide fragments and polypeptides having large internal deletions can be constructed using standard methods (ref. 41), for example, by PCR, including inverse PCR, by restriction enzyme treatment of the cloned DNA molecules, or by the method of Kunkel et al. (ref. 42) biological material available at Stratagene.

A polypeptide derivative can also be produced as a fusion polypeptide that contains a polypeptide or a polypeptide derivative of the invention fused, e.g., at the N- or C-terminal end, to any other polypeptide (hereinafter referred to as a peptide tail). Such a product can be easily obtained by translation of a genetic fusion, i.e., a hybrid gene. Vectors for expressing fusion polypeptides are commercially available, such as the pMal-c2 or pMal-p2 systems of New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

Another particular example of fusion polypeptides included in invention includes a polypeptide or polypeptide derivative of the invention fused to a polypeptide having adjuvant activity, such as, e.g., subunit B of either cholera toxin or E. coli hat-labile toxin. Several possibilities are can be used for achieving fusion. First, the polypeptide of the invention can be fused in the N-, or preferably, to the C-terminal end of the polypeptide having adjuvant activity. Second, a polypeptide fragment of the invention can be fused within the amino acid sequence of the polypeptide having adjuvant activity.

As stated above, the polynucleotides of the invention encode Chlamydia polypeptides in precursor or mature form. They can also encode hybrid precursors containing heterologous signal peptides, which can mature into polypeptides of the invention. By "heterologous signal peptide" is meant a signal peptide that is not found in the naturally-occurring precursor of a polypeptide of the invention.

A polynucleotide of the invention, having a homologous coding sequence, hybridizes, preferably under stringent conditions, to a polynucleotide having a sequence as shown in SEQ ID Nos:1 to 2. Hybridization procedures are, e.g., described in Ausubel et al., (ref. 41), Silhavy et al. (ref. 43); Davis et al. (ref. 44). Important parameters that can be considered for optimizing hybridization conditions are reflected in a formula that allows calculation of a critical value, the melting temperature above which two complementary DNA strands separate from each other ref. 45). This formula is as follows: TM=81.5+0.41×(% G+C)+16.6 log (cation ion concentration)−0.63×(% formamide)−600/base number. Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined empirically in preliminary experiments using conventional procedures.

For example, stringent conditions can be achieved, both for pre-hybridizing and hybridizing incubations, (i) within 4 to 16 hours at 42° C., in 6× SSC containing 50 % formamide or (ii) within 4–16 hours at 65° C. in an aqueous 6× SSC solution (1 M NaCl, 0.1 M sodium citrate (pH 7.0)). Typically, hybridization experiments are performed at a temperature from 60 to 68° C., e.g. 65° C. At such a temperature, stringent hybridization conditions can be achieved in 6×SSC, preferably in 2×SSC or 1×SSC, more preferably in 0.5×SSc, 0.3×SSC or 0.1×SSC (in the absence of formamide). 1×SSC contains 0.15 M NaCl and 0.015 M sodium citrate.

For polynucleotides containing 30 to 600 nucleotides, the above formula is used and then is corrected by subtracting (600/polynucleotide size in base pairs). Stringency conditions are defined by a Th that is 5 to 10° C. below Tm.

Hybridization conditions with oligonucleotides shorter than 20 to 30 bases do not exactly follow the rules set forth above. In such cases, the formula for calculating the Tm is as follows: Tm=4×(G+C)+2(A+T). For example, an 18 nucleotide fragment of 50% G+C would have an approximate Tm of 54° C.

A polynucleotide molecule of the invention, containing RNA, DNA, or modifications or combinations thereof, can have various applications. For example, a DNA molecule can be used (i) in a process for producing the encoded polypeptide in a recombinant host system, (ii) in the construction of vaccine vectors such as poxviruses, which are further used in methods and compositions for preventing and/or treating Chlamydia infection, (iii) as a vaccine agent (as well as an RNA molecule), in a naked form or formulated with a delivery vehicle and, (iv) in the construction of attenuated Chlamydia strains that can over-express a polynucleotide of the invention or express it in a non-toxic, mutated form.

According to further aspects of the invention, there are provided (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system can be selected from procaryotic and eucaryotic hosts. Eucaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. Preferably, a procaryotic host such as E. coli is used. Bacterial and eucaryotic cells are available from a number of different sources to those skilled in the art, e.g., the American Type Culture Collection (ATCC; 10801 University Blvd. Manassas, Va. 20110-2209, USA).

The choice of the expression system depends on the features desired for the expressed polypeptide. For example, it may be useful to produce a polypeptide of the invention in a particular lipidated form or any other form.

The choice of the expression cassette will depend on the host system selected as well as the features desired for the expressed polypeptide. Typically, an expression cassette includes a promoter that is functional in the selected host system and can be constitutive or inducible; a ribosome binding site; a start codon (ATG) if necessary, a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region can be homologous or heterologous to the DNA molecule encoding the mature polypeptide and can be specific to the secretion apparatus of the host used for expression. The open reading frame constituted by the DNA molecule of the invention, solely or together with the signal peptide, is placed under the control of the promoter so that transcription and translation occur in the host system. Promoters, signal peptide encoding regions are widely known and available to those skilled in the art and includes, for example, the promoter of *Salmonella typhimurium* (and derivatives) that is inducible by arabinose (promoter araB) and is functional in Gram-negative bacteria such as E. coli (as described in U.S. Pat. No. 5,028,530 and in Cagnon et al., (ref. 46); the promoter of the gene of bacteriophage T7 encoding RNA polymerase, that is functional in a number of E. coli strains expressing T7 polymerase (described in U.S. Pat. No. 4,952,496); OspA lipidation signal peptide; and RlpB lipidation signal peptide (ref. 47).

The expression cassette is typically part of an expression vector, which is selected for its ability to replicate in the chosen expression system. Expression vectors (e.g., plasmids or viral vectors) can be chosen from those described in Pouwels et al. (Cloning Vectors: A Laboratory Manual 1985, Supp. 1987). They can be purchased from various commercial sources.

Methods for transforming/transfecting host cells with expression vectors will depend on the host system selected as described in Ausubel et al., (ref. 41).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide can then be recovered in a substantially purified form from the cell extract or from the supernatant after centrifugation of the recombinant cell culture. Typically, the recombinant polypeptide can be purified by antibody-based affinity purification or by any other method that can be readily adapted by a person skilled in the art, such as by genetic fusion to a small affinity binding domain. Antibody-based affinity purification methods are also available for purifying a polypeptide of the invention extracted from a Chlamydia strain. Antibodies useful for purifying by immunoaffinity the polypeptides of the invention can be obtained as described below.

A polynucleotide of the invention can also be useful in the vaccine field, e.g., for achieving DNA vaccination. There are two major possibilities, either using a viral or bacterial host as gene delivery vehicle (live vaccine vector) or administering the gene in a free form, e.g., inserted into a plasmid. Therapeutic or prophylactic efficacy of a polynucleotide of the invention can be evaluated as described below.

Accordingly, in additional aspects of the invention, there are provided (i) a vaccine vector such as a poxvirus, containing a DNA molecule of the invention, placed under the control of elements required for expression; (ii) a composition of matter containing a vaccine vector of the invention, together with a diluent or carrier; particularly (iii) a pharmaceutical composition containing a therapeutically or prophylactically effective amount of a vaccine vector of the invention; (iv) a method for inducing an immune response against Chlamydia in a mammal (e.g., a human; alternatively, the method can be used in veterinary applications for treating or preventing Chlamydia infection of animals, e.g., cats or birds), which involves administering to the mammal an immunogenically effective amount of a vaccine vector of the invention to elicit an immune response, e.g., a protective or therapeutic immune response to Chlamydia; and particularly, (v) a method for preventing and/or treating a Chlamydia (e.g., *C. trachomatis, C. psittaci, C. pneumonia, C. pecorum*) infection, which involves administering a prophylactic or therapeutic amount of a vaccine vector of the invention to an individual in need. Additionally, the invention encompasses the use of a vaccine vector of the invention in the preparation of a medicament for preventing and/or treating Chlamydia infection.

Figure 3A:
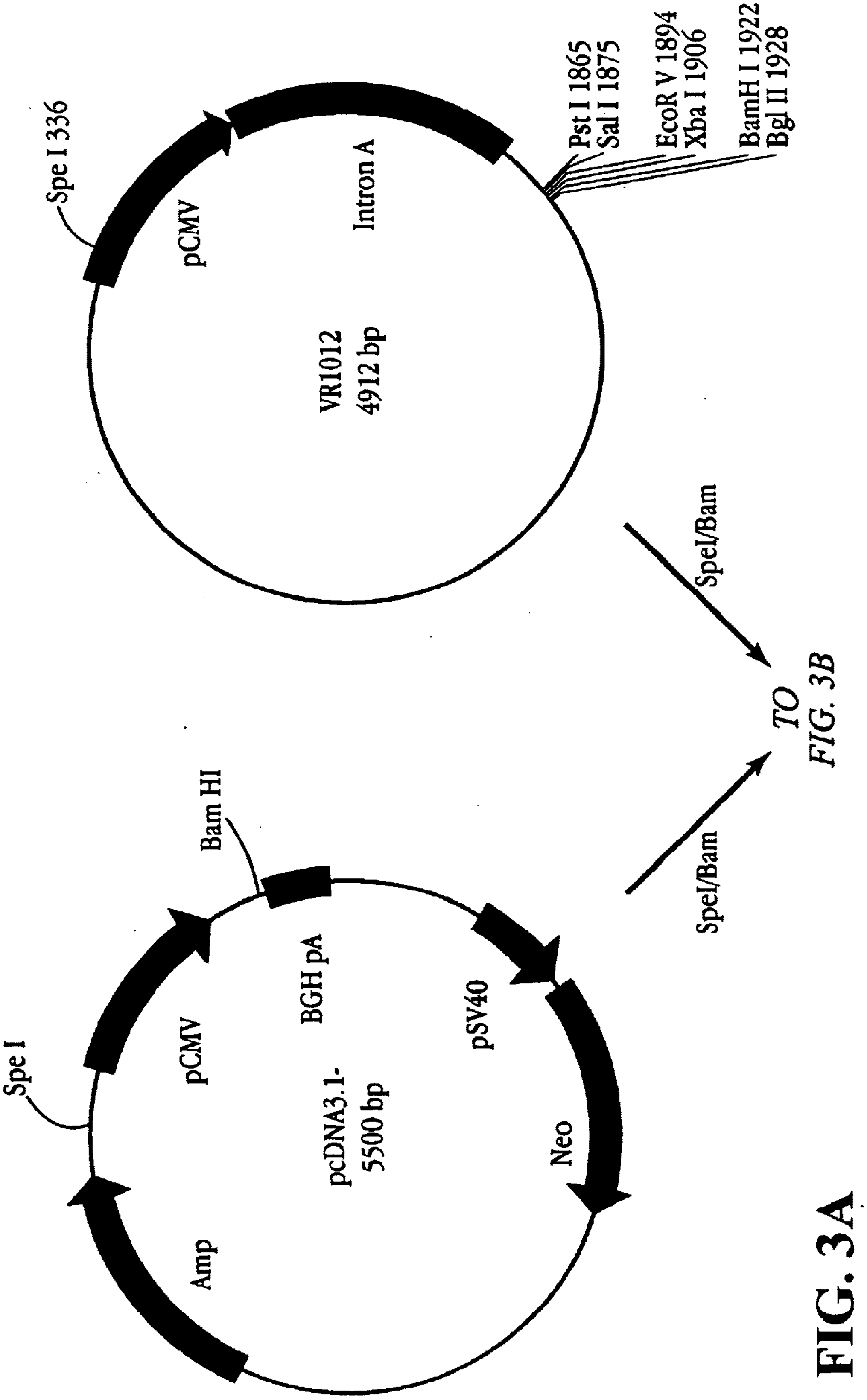
FIGS. 3A–3C show the construction and elements of plasmid pCAl327.
Figure 3B:
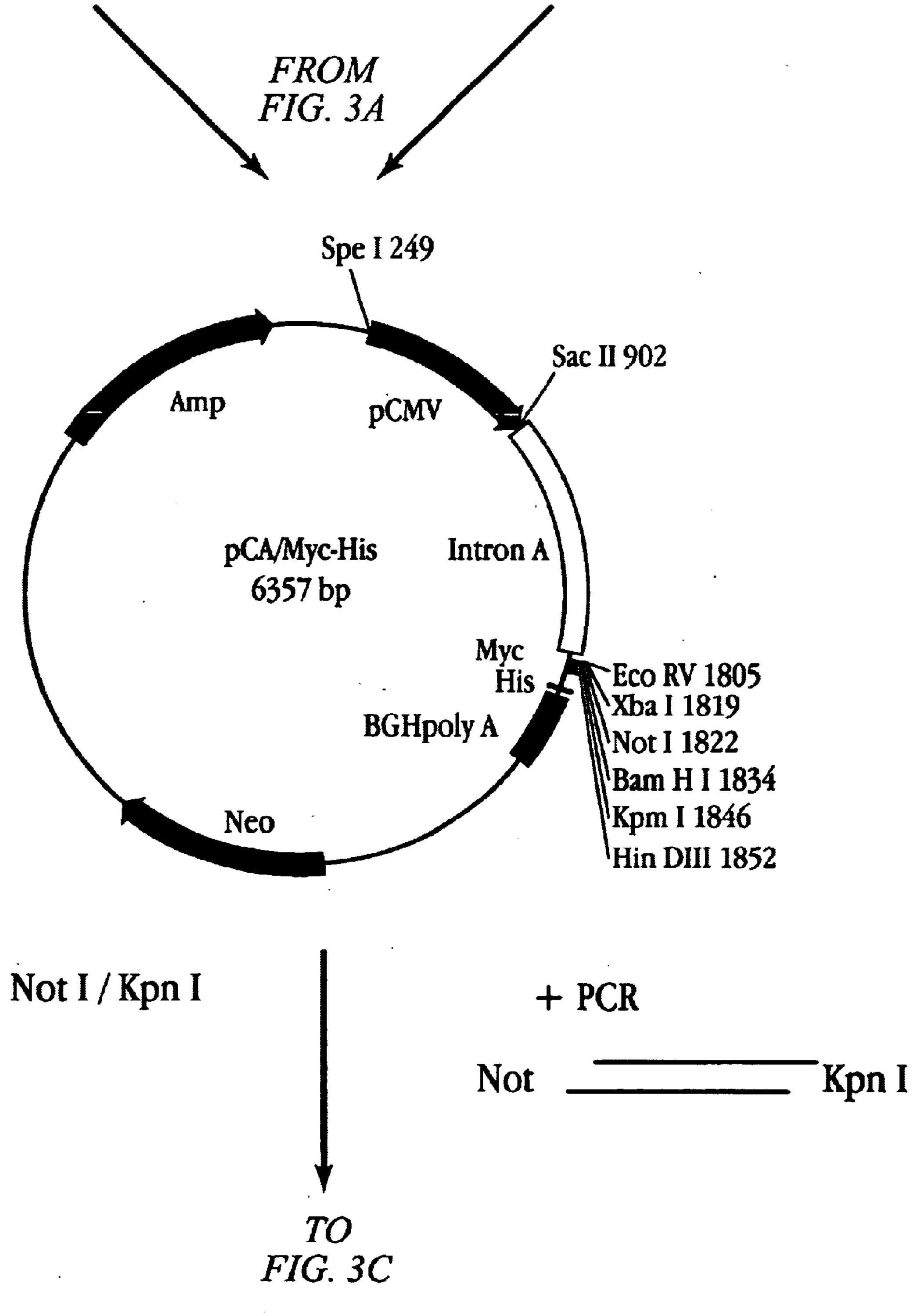
Figures 3B, 3C:
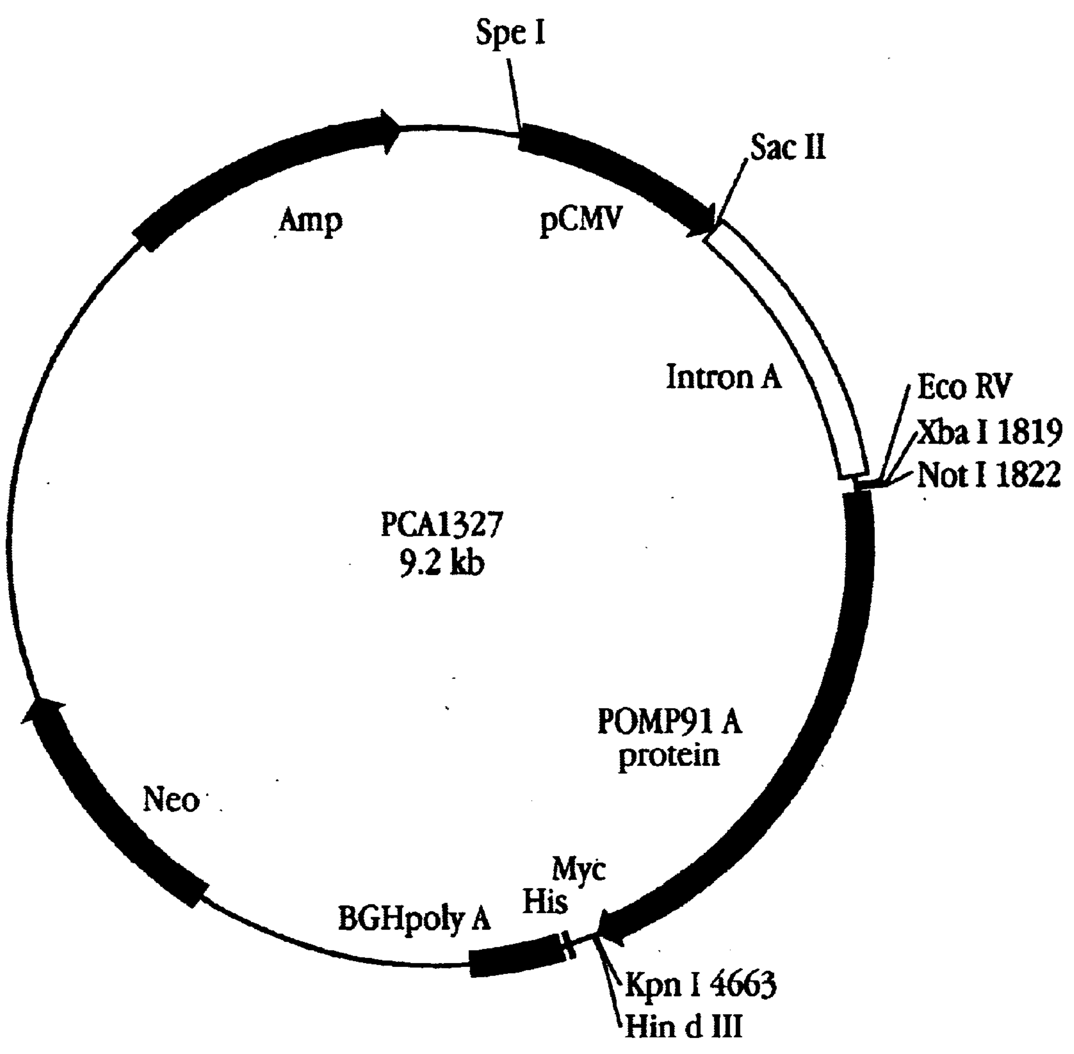

The vaccine vector may be a plasmid vector incapable of separation in mammalian cells. The elements for expression may include a promoter suitable for expression in mammalian cells, particularly a cytomegalovrius vector. The plasmid vector particularly has the identifying characteristics of plasmid pCA1327 as shown in FIGS. 3A–3C.

A vaccine vector of the invention can express one or several polypeptides or derivatives of the invention, as well as at least one additional Chlamydia antigen, fragment, homolog, mutant, or derivative thereof. In addition, it can express a cytokine, such as interleukin-2 (IL-2) or interleukin-12 (IL-12), that enhances the immune response (adjuvant effect). Thus, a vaccine vector can include an additional DNA sequence encoding, e.g., a chlamydial antigen, or a cytokine, placed under the control of elements required for expression in a mammalian cell.

Alternatively, a composition of the invention can include several vaccine vectors, each of them being capable of expressing a polypeptide or derivative of the invention. A composition can also contain a vaccine vector capable of expressing an additional Chlamydia antigen, or a subunit, fragment, homolog, mutant, or derivative thereof; or a cytokine such as IL-2 or IL-12.

In vaccination methods for treating or preventing infection in a mammal, including a human host, a vaccine vector of the invention can be administered by any conventional route in use in the vaccine field, particularly, to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. The administration can be achieved in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., Shigella, Salmonella, *Vibrio cholerae,* Lactobacillus, *Bacille bilié de Calmette-Guérin* (BCG), and Streptococcus.

An example of an adenovirus vector, as well as a method for constructing an adenovirus vector capable of expressing a DNA molecule of the invention, are described in U.S. Pat. No. 4,920,209. Poxvirus vectors that can be used include, e.g., vaccinia and canary pox virus, described in U.S. Pat. No. 4,722,848 and U.S. Pat. No. 5,364,773, respectively (also see, e.g., ref. 54) for a description of a vaccinia virus vector; and ref. 55 for a reference of a canary pox). Poxvirus vectors capable of expressing a polynucleotide of the invention can be obtained by homologous recombination as described in ref. 56 so that the polynucleotide of the invention is inserted in the viral genome under appropriate conditions for expression in mammalian cells. Generally, the dose of vaccine viral vector, for therapeutic or prophylactic use, can be of from about $1\times10^4$ to about $1\times10^{11}$, advantageously from about $1\times10^7$ to about $1\times10^{10}$, preferably of from about $1\times10^7$ to about $1\times10^9$ plaque-forming units per kilogram. Preferably, viral vectors are administered parenterally; for example, in 3 doses, 4 weeks apart. Those skilled in the art recognize that it is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are described in ref. 57 and U.S. Pat. No. 4,882,278 (strain in which a substantial amount of the coding sequence of each of the two ctxA alleles has been deleted so that no functional *cholerae* toxin is produced); WO 92/11354 (strain in which a irgA locus is inactivated by mutation; this mutation can be combined in a single strain with ctxA mutations); and WO 94/1533 (deletion mutant lacking functional ctxA and attRS1 DNA sequences). These strains can be genetically engineered to express heterologous antigens, as described in WO 94/19482. An effective vaccine dose of a *Vibrio cholerae* strain capable of expressing a polypeptide or polypeptide derivative encoded by a DNA molecule of the invention can contain, e.g., about $1\times10^5$ to about $1\times10^9$, preferably about $1\times10^6$ to about $1\times10^8$ viable bacteria in an appropriate volume for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in ref. 58 and WO 92/11361. Preferred routes of administration include all mucosal routes; most preferably, these vectors are administered intranasally or orally.

Others bacterial strains useful as vaccine vectors are described in refs. 59, 60 (*Shigella flexnen*); ref. 61 (*Streptococcus gordonii*); and ref. 62, WO 88/6626, WO 90/0594, WO 91/13157, WO 92/1796, and WO 92/21376 (Bacille Calmette Guerin).

In bacterial vectors, polynucleotide of the invention can be inserted into the bacterial genome or can remain in a free state, carried on a plasmid.

An adjuvant can also be added to a composition containing a vaccine bacterial vector. A number of adjuvants are known to those skilled in the art. Preferred adjuvants can be selected from the list provided below.

According to additional aspects of the invention, there are also provided (i) a composition of matter containing a polynucleotide of the invention, together with a diluent or carrier; (ii) a pharmaceutical composition containing a therapeutically or prophylactically effective amount of a polynucleotide of the invention; (iii) a method for inducing an immune response against Chlamydia, in a mammal, by administering to the mammal, an immunogenically effective amount of a polynucleotide of the invention to elicit an immune response, e.g., a protective immune response to Chlamydia; and particularly, (iv) a method for preventing and/or treating a Chlamydia (e.g., *C. trachomatis, C. psittaci, C. pneumoniae*, or *C. pecorum*) infection, by administering a prophylactic or therapeutic amount of a polynucleotide of the invention to an individual in need. Additionally, the invention encompasses the use of a polynucleotide of the invention in the preparation of a medicament for preventing and/or treating Chlamydia infection. The invention preferably includes the use of a DNA molecule placed under conditions for expression in a mammalian cell, e.g., in a plasmid that is unable to replicate in mammalian cells and to substantially integrate in a mammalian genome.

Polyuncleotides (DNA or RNA) of the invention can also be administered as such to a mammal for vaccine, e.g., therapeutic or prophylactic, purpose. When a DNA molecule of the invention is used, it can be in the form of a plasmid that is unable to replicate in a mammalian cell and unable to integrate in the mammalian genome. Typically, a DNA molecule is placed under the control of a promoter suitable for expression in a mammalian cell. The promoter can function ubiquitously or tissue-specifically. Examples of non-tissue specific promoters include the early Cytomegalovirus (CMV) promoter (described in U.S. Pat. No. 4,168,062) and the Rous Sarcoma Virus promoter (described in ref. 63). The desmin promoter (refs. 64, 65, 66) is tissue-specific and drives expression in muscle cells. More generally, useful vectors are described, i.a., WO 94/21797 and ref. 67.

For DNA/RNA vaccination, the polynucleotide of the invention can encode a precursor or a mature form. When it encodes a precursor form, the precursor form can be homologous or heterologous. In the latter case, a eucaryotic leader sequence can be used, such as the leader sequence of the tissue-type plasminogen factor (tPA).

A composition of the invention can contain one or several polynucleotides of the invention. It can also contain at least one additional polynucleotide encoding another Chlamydia antigen, such as urease subunit A, B, or both; or a fragment, derivative, mutant, or analog thereof. A polynucleotide encoding a cytokine, such as interleukin-2 (IL-2) or interleukin-12 (IL-2), can also be added to the composition so that the immune response is enhanced. These additional polynucleotides are placed under appropriate control for expression. Advantageously, DNA molecules of the invention and/or additional DNA molecules to be included in the same composition, can be carried in the same plasmid.

Standard techniques of molecular biology for preparing and purifying polynucleotides can be used in the preparation of polynucleotide therapeutics of the invention. For use as a vaccine, a polynucleotide of the invention can be formulated according to various methods.

First, a polynucleotide can be used in a naked form, free of any delivery vehicles, such as anionic liposomes, cationic lipids, micrparticles, e.g., gold microparticles, precipitating agents, e.g., calcium phosphate, or any other transfection-facilitating agent. In this case, the polynucleotide can be simply diluted in a physiologically acceptable solution, such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

Alternatively, a polynucleotide can be associated with agents that assist in cellular uptake. It can be, i.a., (i) complemented with a chemical agent that modifies the cellular permeability, such as bupivacaine (see, e.g., WO 94/16737), (ii) encapsulated into liposomes, or (iii) associated with cationic lipids or silica, gold, or tungsten microparticles.

Anionic and neutral liopsomes are well-known in the art (see, e.g., Liposomes: A Practical Approach, RPC New Ed, IRL press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy) propyl]-N-N,N-trimethylammonium chloride), DOTAP (1,2-bis(oleyloxy)-3-(trimethylammonio)propane), DDAB dimethyldioctadecylammonium bromide), DOGS (dioctadecylamidologycyl spermine) and cholesterol derivatives such as DC-Chol (3 beta-(N-(N', N'-dimethyl aminomethane)-carbamoyl) chlesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as, for example, described in WO 90/11092.

Other transfection-facilitating compounds can be added to a formulation containing cationic liposomes. A number of them are described in, e.g., WO 93/18759, WO 93/19768, WO 94/25608, and WO 95/2397. They include, i.a., spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for gene delivery, as described in WO 91/359, WO 93/17706, and ref. 68. In this case, the microparticle-coated polynucleotides can be injected via intradermal or intraepidermal routes using a needleless injection device ("gene gun"), such as those described in ref. 69 and in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 $\mu$g to about 1 mg, preferably, from about 10 $\mu$g to about 800 $\mu$g and, more preferably, from about 25 $\mu$g to about 250 $\mu$g, can be administered to human adults. The administration can be achieved in a single dose or repeated at intervals.

The route of administration can be any conventional route used in the vaccine field. As general guidance, a polynucleotide of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of the administration route will depend on, e.g., the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or subcutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that can be useful in diagnosis. Accordingly, in a further aspect of the invention, there is provided a nucleotide probe or primer having a sequence found in or derived by degeneracy of the genetic code from a sequence shown in SEQ ID Nos:1 to 2.

The term "probe" as used in the present application refers to DNA (preferably single stranded) or RNA molecules (or modifications or combinations thereof) that hybridize under the stringent conditions, as defined above, to nucleic acid molecules having sequences homologous to those shown in SEQ ID Nos:1 and 2, or to a complementary or anti-sense sequence. Generally, probes are significantly shorter than full-length sequences shown in SEQ ID Nos:1 and 2; for example, they can contain from about 5 to about 100, preferably from about 10 to about 80 nucleotides. In particular, probes have sequences that are at least 75%, preferably at least 85%, more preferably 95% homologous to a portion of a sequence as shown in SEQ ID Nos:1 and 2 or that are complementary to such sequences. Probes can contain modified bases such as inosine, methyl-5-deoxycytidine, deoxyuridine, dimethylamino-5-deoxyuridine, or diamino-2,6-purine. Sugar or phosphate residues can also be modified or substituted. For example, a deoxyribose residue can be replaced by a polyamide (ref. 70) and phosphate residues can be replaced by ester groups such as diphosphate, alkyl, arylphosphonate and phosphorothioate esters. In addition, the 2'-hydroxyl group on ribonucleotides can be modified by including, e.g., alkyl groups.

Probes of the invention can be used in diagnostic tests, as capture or detection probes. Such capture probes can be conventionally immobilized on a solid support, directly or indirectly, by covalent means or by passive adsorption. A detection probe can be labelled by a detection marker selected from radioactive isotypes; enzymes such as peroxidase, alkaline phosphatase, and enzymes able to hydrolyze a chromogenic, fluorogenic, or luminescent substrate; compounds that are chromogenic, fluorogenic, or luminescent; nucleotide base analogs; and biotin.

Probes of the invention can be used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (ref. 71), northern blot (identical to Southern blot to the exception that RNA is used as a target), or the sandwich technique (ref. 72). The latter technique involves the use of a specific capture probe and/or a specific detection probe with nucleotide sequences that at least partially differ from each other.

A primer is usually a probe of about 10 to about 40 nucleotides that is used to initiate enzymatic polymerization of DNA in an amplification process (e.g., PCR), in an elongation process, or in a reverse transcription method. In a diagnostic method involving PCR, primers can be labelled.

Thus, the invention also encompasses (i) a reagent containing a probe of the invention for detecting and/or identifying the presence of Chlamydia in a biological material; (ii) a method for detecting and/or identifying the presence of Chlamydia in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of Chlamydia in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

As previously mentioned, polypeptides that can be produced upon expression of the newly identified open reading frames are useful vaccine agents.

Therefore, an additional aspect of the invention features a substantially purified polypeptide or polypeptide derivative having an amino acid sequence encoded by a polynucleotide of the invention.

A "substantially purified polypeptide" is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art will understand that the polypeptides of the invention can be purified from a natural source, i.e., a Chlamydia strain, or can be produced by recombinant means.

Homologous polypeptides or polypeptide derivatives encoded by polynucleotides of the invention can be screened for specific antigenicity by testing cross-reactivity with an antiserum raised against the polypeptide of reference having an amino acid sequence as shown in SEQ ID No:3. Briefly, a monospecific hyperimmune antiserum can be raised against a purified reference polypeptide as such or as a fusion polypeptide, for example, an expression produce of MBP, GST, or His-tag systems or a synthetic peptide predicted to be antigenic. The homologous polypeptide or derivative screened for specific antigenicity can be produced as such or as a fusion polypeptide. In this latter case and if the antiserum is also raised against a fusion polypeptide, two different fusion systems are employed. Specific antigenicity can be determined according to a number of methods, including Western blot (ref. 73), dot blot, and ELISA, as described below.

In a Western blot assay, the product to be screened, either as a purified preparation or a total *E. coli* extract, is submitted to SDS-Page electrophoresis as described by Laemmli (ref. 74). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 $\mu$l of a preparation at about 10 $\mu$g protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 $\mu$l PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 $\mu$l of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 $\mu$g/ml is serially two-fold diluted in 50 mM Tris-HCL (pH 7.5). 100 $\mu$l of each dilution are applied to a nitrocellulose membrane 0.45 $\mu$m set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below.

According to additional aspects of the invention, there are provided (i) a composition of matter containing a polypeptide of the invention together with a diluent or carrier; in particular, (ii) a pharmaceutical composition containing a therapeutically or prophylactically effective amount of a polypeptide of the invention; (iii) a method for inducing an immune response against Chlamydia in a mammal, by administering to the mammal an immunogenically effective amount of a polypeptide of the invention to elicit an immune response, e.g., a protective immune response to Chlamydia; and particularly, (iv) a method for preventing and/or treating a Chlamydia (e.g., *C. trachomatis. C. psittaci, C. pneumoniae.* or *C. pecorum*) infection, by administering a prophylactic or therapeutic amount of a polypeptide of the invention to an individual in need. Additionally, the seventh aspect of the invention encompasses the use of a polypeptide of the invention in the preparation of a medicament for preventing and/or treating Chlamydia infection.

The immunogenic compositions of the invention can be administered by any conventional route in use in the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of the administration route depends upon a number of parameters, such as the adjuvant associated with the polypeptide. For example, if a mucosal adjuvant is used, the intranasal or oral route will be preferred and if a lipid formulation or an aluminum compound is used, the parenteral route will be preferred. In the latter case, the sub-cutaneous or intramuscular route is most preferred. The choice can also depend upon the nature of the vaccine agent. For example, a polypeptide of the invention fused to CTB or LTB will be best administered to a mucosal surface.

A composition of the invention can contain one or several polypeptides or derivatives of the invention. It can also contain at least one additional Chlamydia antigen, or a subunit, fragment, homolog, mutant, or derivative thereof.

For use in a composition of the invention, a polypeptide or derivative thereof can be formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see Liposomes: A Practical Approach (supra).

Adjuvants other than lipsomes and the like can also be used and are known in the art. A appropriate selection can conventionally be made by those skilled in the art, for example, from the list provided below.

Administration can be achieved in a single dose or repeated as necessary at intervals as can be determined by one skilled in the art. For example, a priming dose can be followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention can be administered by a mucosal route in an amount from about 10 $\mu$g to about 500 mg, preferably from about 1 mg to about 200 mg. For the parenteral route of administration, the dose usually should not exceed about 1 mg, preferably about 100 $\mu$g.

When used as vaccine agents, polynucleotides and polypeptides of the invention can be used sequentially as part of a multistep immunization process. For example, a mammal can be initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention can also be used for priming, with boosting being carried out mucosally using a soluble polypeptide or derivative of the invention in combination with a mucosal adjuvant (e.g., LT).

A polypeptide derivative of the invention is also useful as a diagnostic reagent for detecting the presence of anti-Chlamydia antibodies, e.g., in a blood sample. Such polypeptides are about 5 to about 80, preferably about 10 to about 50 amino acids in length and can be labeled or unlabeled, depending upon the diagnostic method. Diagnostic methods involving such a reagent are described below.

Upon expression of a DNA molecule of the invention, a polypeptide or polypeptide derivative is produced and can be purified using known laboratory techniques. For example, the polypeptide or polypeptide derivative can be produced as a fusion protein containing a fused tail that facilitates purification. The fusion product can be used to immunize a small mammal, e.g., a mouse or a rabbit, in order to raise antibodies against the polypeptide or polypeptide derivative (monospecific antibodies). The eighth aspect of the invention thus provides a monospecific antibody that binds to a polypeptide or polypeptide derivative of the invention.

By "monospecific antibody" is meant an antibody that is capable of reacting with a unique naturally-occurring Chlamydia polypeptide. An antibody of the invention can be polyclonal or monoclonal. Monospecific antibodies can be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies can also be in the form of immunoglobulin fragments, e.g., F(ab)'2 or Fab fragments. The antibodies of the invention can be of any isotype, e.g., IgG or IgA, and polyclonal antibodies can be of a single isotype or can contain a mixture of isotypes.

The antibodies of the invention, which are raised to a polypeptide or polypeptide derivative of the invention, can be produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies can be used in diagnostic methods to detect the presence of a Chlamydia antigen in a sample, such as a biological sample. The antibodies can also be used in affinity chromatography methods for purifying a polypeptide or polypeptide derivative of the invention. As is discussed further below, such antibodies can be used in prophylactic and therapeutic passive immunization methods.

Accordingly, further aspects of the invention provides (i) a reagent for detecting the presence of Chlamydia in a biological sample that contains an antibody, polypeptide, or polypeptide derivative of the invention; and (ii) a diagnostic method for detecting the presence of Chlamydia in a biological sample, by contacting the biological sample with an antibody, a polypeptide, or a polypeptide derivative of the invention, such that an immune complex is formed, and by detecting such complex to indicate the presence of Chlamydia in the sample or the organism from which the sample is derived.

Those skilled in the art will understand that the immune complex is formed between a component of the sample and the antibody, polypeptide, or polypeptide derivative, whichever is used, and that any unbound material can be removed prior to detecting the complex. As can be easily understood, a polypeptide reagent is useful for detecting the presence of anti-Chlamydia antibodies in a sample, e.g., a blood sample, while an antibody of the invention can be used for screening a sample, such as a gastric extract or biopsy, for the presence of Chlamydia polypeptides.

For use in diagnostic applications, the reagent (i.e., the antibody, polypeptide, or polypeptide derivative of the invention) can be in a free state or immobilized on a solid support, such as a tube, a bead, or any other conventional support used in the field. Immobilization can be achieved using direct or indirect means. Direct means include passive adsorption (non-covalent binding) or covalent binding between the support and the regent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means can also employ a ligand-receptor system, for example, a molecule such as a vitamin can be grafted onto the polypeptide reagent and the corresponding receptor can be immobilized on the solid phase. This is illustrated by the biotin-streptavidin system. Alternatively, indirect means can be used, e.g., by adding to the reagent a peptide tail, chemically or by genetic engineering, and immobilizing the grafted or fused product by passive adsorption or covalent linkage of the peptide tail.

According to a further aspect of the invention, there is provided a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody can be polyclonal or monospecific, and preferably is of the IgG type. Purified IgGs can be prepared from an antiserum using standard methods (see, e.g., Coligan et al., supra). Conventional chromatography supports, as well as standard methods for grafting antibodies, are disclosed in, e.g., Antibodies: A Laboratory Manual, D. Lane, E. Harlow, Eds. (1988).

Briefly, a biological sample, such as an *C. pneumoniae* extract, preferably in a buffer solution is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, can be in batch form or in a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An antibody of the invention can be screened for therapeutic efficacy as described as follows. According to additional aspects of the invention, there are provided (i) a composition of matter containing a monospecific antibody of the invention, together with a diluent or carrier; (ii) a pharmaceutical composition containing a therapeutically or prophylactically effective amount of a monospecific antibody of the invention, and (iii) a method for treating or preventing a Chlamydia (e.g., *C. trachomatis, C. psittaci, C. pneumoniae* or *C. pecorum*) infection, by administering a therapeutic or prophylactic amount of a monospecific antibody of the invention to an individual in need. Additionally, an additional aspect of the invention encompasses the use of a monospecific antibody of the invention in the preparation of a medicament for treating or preventing Chlamydia infection.

To this end, the monospecific antibody can be polyclonal or monoclonal, preferably of the IgA isotype (predominantly). In passive immunization, the antibody can be administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, can be carried out. A monospecific antibody of the invention can be administered as a single active component or as a mixture with at least one monospecific antibody specific for a different Chlamydia polypeptide. The amount of antibody and the particular regimen used can be readily determined by one skilled in the art. For example, daily administration of about 100 to 1,000 mg of antibodies over one week, or three doses per day of about 100 to 1,000 mg of antibodies over two or three days, can be an effective regimens for most purposes.

Therapeutic or prophylactic efficacy can be evaluated using standard methods in the art, e.g., by measuring induction of a mucosal immune response or induction of protective and/or therapeutic immunity, using, e.g., the *C. pneumoniae* mouse model. Those skilled in the art will recognize that the *C. pneumoniae* strain of the model can be replaced with another Chlamydia strain. For example, the efficacy of DNA molecules and polypeptides from *C. pneumoniae* is preferably evaluated in a mouse model using an *C. pneumoniae* strain. Protection can be determined by comparing the degree of Chlamydia infection to that of a control group. Protection is shown when infection is reduced by comparison to the control group. Such an evaluation can be made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen can be precipitated with, or adsorbed onto, the aluminum compound according to standard protocols. Other adjuvants, such as RIBI (ImmunoChem, Hamilton, Mont.), can be used in parenteral administration.

Adjuvants for mucosal administration include bacterial toxins, e.g., the cholera toxin (CT), the *E. coli* heat-labile toxin (LT), the *Clostridium difficile* toxin A and the *pertussis* toxin (PT), or combinations, subunits, toxoids, or mutants thereof. For example, a purified preparation of native cholera toxin subunit B (CTB) can be of use. Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium*, or *Shigella flexneri*; saponins, or polylactide glycolide (PLGA) microspheres, can also be used in mucosal administration.

Adjuvants useful for both mucosal and parenteral administrations include polyphosphazene (WO 95/2415), DC-chol (3 b-(N-(N',N'- dimethyl aminomethane)-carbamoyl) cholesterol; U.S. Pat. No. 5,283,185 and WO 96/14831) and QS-21 (WO 88/9336).

Any pharmaceutical composition of the invention, containing a polynucleotide, a polypeptide, a polypeptide derivative, or an antibody of the invention, can be manufactured in a conventional manner. In particular, it can be formulated with a pharmaceutically acceptable diluent or carrier, e.g., water or a saline solution such as phosphate buffer saline. In general, a diluent or carrier can be selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which Chlamydia infection, are treated by oral administration of a Chlamydia polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or imunomodulators such as cytokines or steroids. In addition, compounds containing more than one of the above-listed components coupled together, can be used. The invention also includes compositions for carrying out these methods, i.e., compositions containing a Chlamydia antigen (or antigens) of the invention, an adjuvant, and one or more of the above-listed compounds, in a pharmaceutically acceptable carrier or diluent.

It has recently been shown that the 60 kDa cysteine rich membrane protein contains a sequence cross-reactive with the murine alpha-myosin heavy chain epitope M7A-alpha, an epitope conserved in humans (ref. 75). This cross-reactivity is proposed to contribute to the development of cardiovascular disease, so it may be beneficial to remove this epitope, and any other epitopes cross-reactive with human antigens, from the protein if it is to be used as a vaccine. This could be achieved by modification of the coding sequence, for example, deletion or substitution of the nucleotides encoding the epitope from polynucleotides encoding the protein. A similar approach may be appropriate for any protective antigen found to have unwanted homologies or cross-reactivities with human antigen.

Amounts of the above-listed compounds used in the methods and compositions of the invention, can readily be determined by one skilled in the art. In addition, one skilled in the art can readily design treatment/immunization schedules. For example, the non-vaccine components can be administered on days 1–14, and the vaccine antigen+adjuvant can be administered on days 7, 14, 21, and 28.

EXAMPLES

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This Example illustrates the preparation of a plasmid vector pCAI327 containing the POMP91A gene.

The POMP91A was amplified from *Chlamydia pneumoniae* strain CMI genomic DNA by polymerase chain reaction (PCR) using a 5' primer (5' ATAAGAAT GCGGCCGCCACCATGAAGCAGATGCGTCTTTGGGG 3') (SEQ ID No:4) and a 3' primer (5' GCGCC GGTACCGGAAAC TAAGGGAGAGGCCTGCATG 3') (SEQ ID No:5). The 5' primer contains a Not I restriction site, a ribosome binding site, an initiation codon and a sequence at the 5' end of the POMP91A coding sequence (SEQ ID No:2). The 3' primer includes the sequence encoding the C-terminal sequence of the POMP91A and a Kpn I restriction site. The stop codon was excluded and an additional nucleotide was inserted to obtain an in-frame fusion with the Histidine tag.

After amplification of the genomic DNA, the PCR fragment was purified using QIAquick™ PCR purification kit (Qiagen) and then digested with Not I and Kpn I and cloned into the pCA-Myc-His eukaryotic expression vector described in Example 2 (FIGS. 3A–3C) with transcription under control of the human CMV promoter.

Example 2

This Example illustrates the preparation of the eukaryotic expression vector pCAI327.

Plasmid pcDNA3.1(−)Myc-His C (Invitrogen) was restricted with Spe I and Bam HI to remove the CMV promoter and the remaining vector fragment was isolated. The CMV promoter and intron A from plasmid VR-1012 (Vical) was isolated on a Spe I/Bam HI fragment. The fragments were ligated together to produce plasmid pCA/Myc-His. The Not I/Kpn I restricted PCR fragment containing the POMP91A gene from Example 1 was ligated into the Not I and Kpn I restricted plasmid pCA/Myc-His to produce plasmid pCAI327 (FIGS. 3A–3C).

The resulting plasmid, pCAI327, was transfered by electroporation into *E. coli* XL-1 blue (Stratagene) which was grown in LB broth containing 50 μg/ml of carbenicillin. The plasmid was isolated by Endo Free Plasmid Giga Kit™ (Qiagen) large scale DNA purification system. DNA concentration was determined by absorbance at 260 nm and the plasmid was verified after gel electrophoresis and Ethidium bromide staining and comparison to molecular weight standards. The 5' and 3' ends of the gene were verified by sequencing using a LiCor model 4000 L DNA sequencer and IRD-800 labelled primers.

Example 3

This example illustrates the immunization of mice to achieve protection against an intranasal challenge by *C. pneumoniae.*

It has been previously demonstrated (ref. 76) that mice are susceptible to intranasal infection with different isolates of *C. pneuomoniae*. Strain AR-39 (ref. 77) was used in Balb/c mice as a challenge infection model to examine the capacity of chlamydia gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (8 to 10 per group) were immunized intramuscularly (i.m.) plus intranasally (i.n.) with plasmid DNA containing the coding sequence of *C. pneumoniae* POMP91A, prepared as described in Examples 1 and 2. Saline and plasmids pCAI116 and pCAI178, which express non-protective chlamydial antigens, were given to groups of control animals.

For i.m. immunization alternate left and right quadriceps were injected with 100 μg of DNA in 50 μl of PBS on three occasions at 0, 3 and 6 weeks. For i.n. immunization, anaesthetized mice aspirated 50 μl of PBS containing 50 μg DNA on three occasions at 0, 3 and 6 weeks. At week 8, immunized mice were inoculated i.n. with $5\times10^5$ IFU of *C. pneumoniae*, strain AR39 in 100 μl of SPG buffer to test their ability to limit the growth of a sublethal *C. pneumoniae* challenge.

Lungs were taken from mice at days 5 and 9 post-challenge and immediately homogenised in SPG buffer (7.5% sucrose, 5 mM glutamate, 12.5 mM phosphate pH7.5). The homogenate was stored frozen at −70° C. until assay. Dilutions of the homogenate were assayed for the presence of infectious chlamydia by inoculation onto monolayers of susceptible cells. The inoculum was centrifuged onto the cells at 3000 rpm for 1 hour, then the cells were incubated for three days at 35° C. in the presence of 1 μg/ml cycloheximide. After incubation the monolayers were fixed with formalin and methanol then immunoperoxidase stained for the presence of chlamydial inclusions using convalescent sera from rabbits infected with *C. pneumoniae* and metal-enhanced DAB as a peroxidase substrate.

Figure 4:
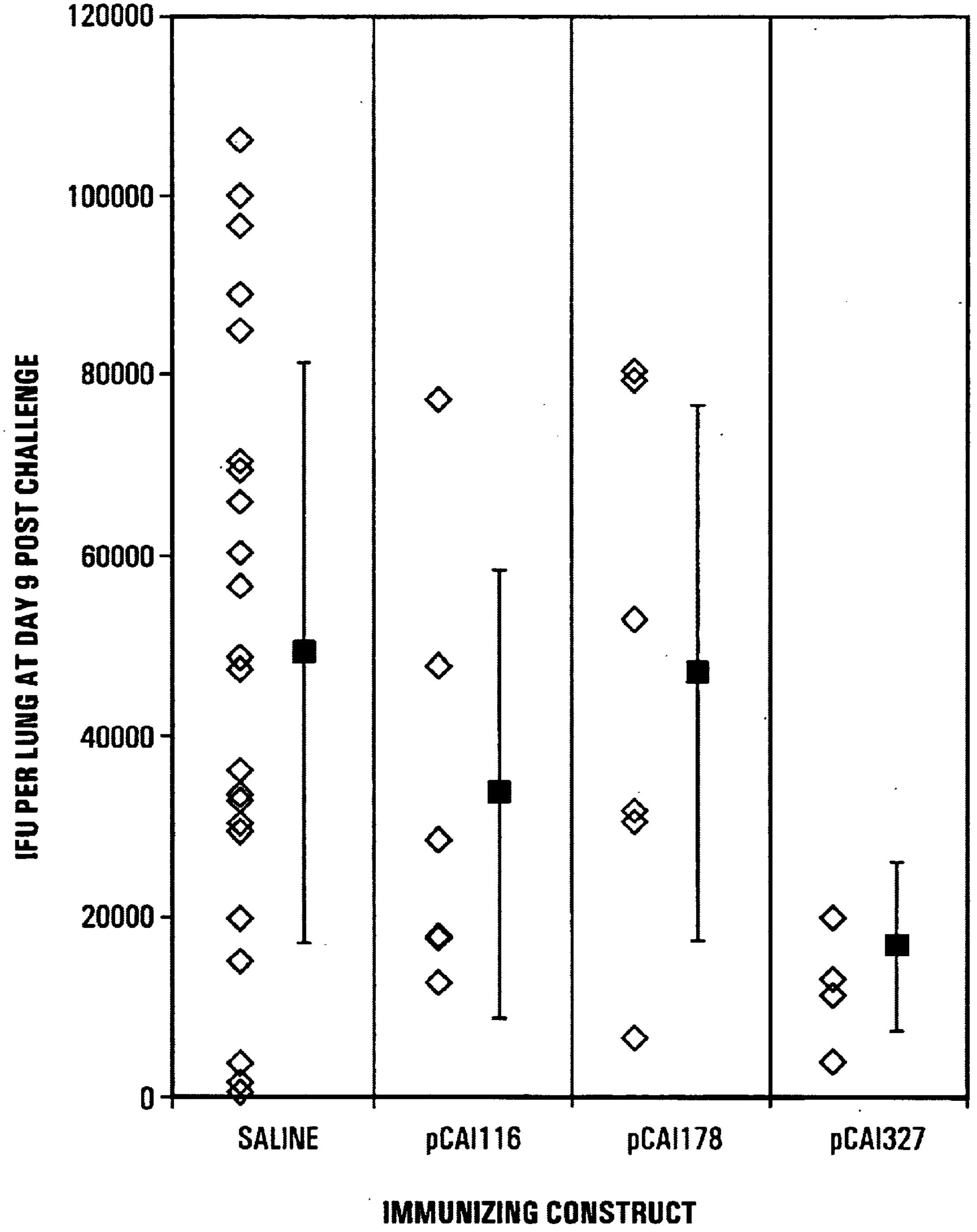
FIG. 4 illustrates protection against *C. pneumoniae* infection by pCAl327 following immunization with p CAl327, in comparison to controls, wherein individual data points (open diamonds) are shown for each animal, as well as the mean (solid squares) and standard deviation for each group.

FIG. 4 and Table 1 show that mice immunized i.n. and i.m. with pCAI327 had chlamydial lung titers less than 21,500 in 5 of 6 cases at day 9 whereas the range of values for control mice sham immunized with saline was 600–106,100 IFU/lung (mean 49,069) at day 9. DNA immunisation per se was not responsible for the observed protective effect since two other plasmid DNA constructs, pCAI116 and pCAI178, failed to protect, with lung titers in immunised mice similar to those obtained for saline-immunized control mice. The constructs pCAI116 and pCAI178 are identical to pCAI327 except that the nucleotide sequence encoding the POMP91A is replaced with a *C. pneumoniae* nucleotide sequence encoding an unprotective sequence and the nucleoside 5'-diphosphate phosphotransferase protein.

TABLE 1

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS IMMUNIZING CONSTRUCT

| MOUSE | Saline Day 9 | pCAI116 Day 9 | pCAI178 Day 9 | pCAI327 Day 9 |
|---|---|---|---|---|
| 1 | 1700 | 47700 | 80600 | 30700 |
| 2 | 36200 | 12600 | 31900 | 13000 |
| 3 | 106100 | 28600 | 30600 | 11300 |
| 4 | 33500 | 17700 | 6500 | 3900 |
| 5 | 70400 | 77300 | 53000 | 19900 |
| 6 | 48700 | 17600 | 79500 | 21400 |
| 7 | 600 | | | |
| 8 | 19800 | | | |
| 9 | 29500 | | | |
| 10 | 100000 | | | |
| 11 | 15000 | | | |
| 12 | 56600 | | | |
| 13 | 60300 | | | |
| 14 | 88800 | | | |
| 15 | 30400 | | | |
| 16 | 69300 | | | |
| 17 | 47500 | | | |
| 18 | 96500 | | | |
| 19 | 30200 | | | |
| 20 | 84800 | | | |
| 21 | 3800 | | | |
| 22 | 65900 | | | |
| 23 | 33000 | | | |
| MEAN | 49069.57 | 33583.33 | 47016.67 | 16700 |
| SD | 32120.48 | 24832.67 | 29524.32 | 9327.59 |

SUMMARY OF DISCLOSURE

In summary of this disclosure, the present invention provides a method of nucleic acid, including DNA, immunization of a host, including humans, against disease caused by infection by a strain of Chlamydia, specifically *C. pneumoniae*, employing a vector, containing a nucleotide sequence encoding a POMP91A of a strain of *Chlamydia pneumoniae* and a promoter to effect expression of the POMP91A gene in the host. Modifications are possible within the scope of this invention.

REFERENCES

1. Grayston et al. (1995) Journal of Infectious Diseases 168:1231.
2. Campos et al. (1995) Investigation of Ophthalmology and Visual Science 36:1477.
3. Grayston et al (1990) Journal of Infectious Diseases 161:618.
4. Marrie (1993) Clinical Infectious Diseases. 18:501.
5. Wang et al (1986) Chlamydial infections. Cambridge University Press, Cambridge.p. 329.
6. Norman et al., Acta Paediatrica, 1998, Vol 87, Iss 1, pp 23–27.
7. Saikku et al.(1988) Lancet;ii:983.
8. Thom et al. (1992) JAMA 268:68.
9. Linnanmaki et al. (1993), Circulation 87:1030.
10. Saikku et al. (1992)Annals Internal Medicine 116:273.
11. Melnick et al(1993) American Journal of Medicine 95:499.
12. Shor et al. (1992) South African. Medical Journal 82:158.
13. Kuo et al. (1993) Journal of Infectious Diseases 167:841.
14. Kuo et al. (1993) Arteriosclerosis and Thrombosis 13:1500.
15. Campbell et al (1995) Journal of Infectious Diseases 172:585.
16. Chiu et al. Circulation, 1997 (In Press).
17. Ramirez et al (1996) Annals of Internal Medicine 125:979.
18. Jackson et al. Abst. K121, p272, 36th ICAAC, Sep. 15–18 , 1996, New Orleans.
19. Fong et al (1997) Journal of Clinical Microbiology 35:48.
20. Hahn D L, et al. Evidence for *Chlamydia pneumoniae* infection in steroid-dependent asthma. Ann Allergy Asthma Immunol. 1998 January: 80(1): 45–49.
21. Hahn D L, et al. Association of *Chlamydia pneumoniae* igA antibodies with recently symptomatic asthma. Epidemiol Infect. 1996 December; 117(3): 513–517.
22. Bjornsson E, et al. Serology of chlamydia in relation to asthma and bronchial hyperresponsiveness. Scand J Infect Dis. 1996; 28(1): 63–69.
23. Hahn D L. Treatment of *Chlamydia pneumoniae* infection in adult asthma: a before-after trial. J Fam Pract. 1995 October; 41(4): 345–351.
24. Allegra L, et al. Acute exacerbations of asthma in adults: role of *Chlamydia pneumoniae* infection. Eur Respir J. 1994 December; 7(12): 2165–2168.
25. Hahn D L, et al. Association of *Chlamydia pneumoniae* (strain TWAR) infection with wheezing, asthmatic bronchitis, and adult-onset asthma. JAMA. July 10, 1991; 266(2): 225–230.
26. Pal et al.(1996) Infection and Immunity.64:5341.
27. Jones et al. (1995) Vaccine 13:715.
28. Igietsemes et al. (1993) Immunology 5:317.
29. Igietseme et al (1993) Regional Immunology 5:317.
30. Magee et al (1993) Regional Immunology 5:305.
31. Landers et al (1991) Infection & Immunity 59:3774.
32. Magee et al (1995) Infection & Immunity 63:516.
33. Cotter et al. (1995) Infection and Immunity 63:4704.

34. Campbell et al (1990) Infection and Immunity 58:93.
35. McCafferty et al (1995) Infection and Immunity 63:2387–9.
36. Knudsen et al (1996) Third Meeting of the European Society for Chlamydia Research, Vienna.
37. Wiedmann-Al-Ahmad M, et al. Reactions of polyclonal neutralizing anti-p54 monoclonal antibodies with an isolated, species-specific 54-kilodalton protein of *Chlamydia pneumoniae*. Clin Diagn Lab Immunol. 1997 November; 4(6): 700–704.
38. Hughes et al., 1992. Infect. Immun. 60(9):3497.
39. Dion et al., 1990. Virology 179:474–477.
40. Snijders et al., 1991. J. Gen. Virol. 72:557–565.
41. Langeveld et al., Vaccine 12(15):1473–1480, 1994.
42. Ausubel et al., Current Protocols in Molecular Biology, John Wiley & Sons Inc., 1994.
43. Kunkel et al. Proc. Natl. Acad. Sci. USA (1985) 82:448.
44. Silhavy et al. Experiments with Gene Fusions, Cold Spring Harbor Laboratory press, 1984.
45. Davis et al. A Manual for Genetic Engineering: Advanced Bacterial Genetics, Cold Spring Harbor Laboratory Press, 1980).
46. Casey & Davidson, Nucl. Acid Res. (1977) 4:1539.
47. Cagnon et al., Protein Engineering (1991) 4(7):843.
48. Takase et al., J. Bact. (1987) 169:5692.
49. Perez Melgosa et al., Infect Immun (1994) 62:880.
50. Watson et al., Nucleic Acids Res (1990) 18:5299.
51. Watson et al., Microbiology (1995) 141:2489.
52. Melgosa et al., FEMS Microbiol Lett (1993) 112:199.
53. Campbell et al., J Clin Microbiol (1990) 28:1261.
54. Iijima et al., J Clin Microbiol (1994) 32:583.
54. Tartaglia et al, Virology (1992) 188:217.
55. Taylor et al, Vaccine (1995) 15:359.
56. Kieny et al., Nature (1994) 312:163.
57. Mekalanos et al., Nature (1983) 306:551.
58. Nakayama et al., Bio/Tech. (1988) 6:693.
59. High et al., EMBO (1992) 11:1991.
60. Sizemore et al., Science (1995) 270:299.
61. Medaglini et al., Pro. Natl. Acad. Sci. USA (1995) 92:6868.
62. Flynn J. L., Cell. Mol. Biol. (1994) 40 (suppl. I):31.
63. Norton & Coffin, Molec. Cell Biol. (1985) 5:281.
64. Li et al., Gene (1989) 78:243.
65. Li & Paulin, J. Biol. Chem. (1991) 266:6562.
66. Li & Paulin, J. Biol. Chem. (1993) 268:10403.
67. Hartikka et al., Huiman Gene Therapy (1996) 7:1205.
68. Tang et al., Nature (1992) 356:152.
69. Furth et al., Vaccine 1994, 12:1503–1509.
70. Nielsen et al., Science (1991) 254:1497.
71. Southern, J. Mol. Biol. (1975) 98:503.
72. Dunn et al., Cell (1977) 12:23.
73. Towbin et al., Proc. Natl. Acad. Sci. USA (1779) 76:4350.
74. Laemmli, Nature (1970) 227:680.
75. Bachmaier et al., Science (1999) 283:1335.
76. Yang et al., 1993, Infection & Immunity, vol. 61, pp 2037–40.
77. Chi E. Y., Kuo C. C., Grayston J. T., 1987. Unique ultrastructure in the elementary body of Chlamydia sp strain TWAR. J. Bacteriol 169(8):3757–63.
78. Needleman, S. B., and Wunsch, C. D. 1970, J. Mol Biol. 48:443–453.
79. Sellers, P. H. 1974 On the theory and computation of evolutionary distances. J. Appl. Math(Siam) 26:787–793.
80. Waterman, M. S., Smith, T. F., and Beyer, W. A. 1976. Advan. Math. 20:367–387.
81. Smith, T. F., and Waterman, M. S. 1981 Identification of common molecular subsequences. J. Mol. Biol. 147:195–197.
82. Sobel, E. and Martinez, H. M. 1985 A Multiple Sequence Alignment Program. Nucleic Acid Res. 14:363–374.

---

What we claim is:

1. An isolated and purified nucleic acid molecule comprising a polynucleotide sequence encoding an amino acid sequence selected from the group consisting of:

(a) an amino acid sequence as set forth in SEQ ID NO:3; and (b) a fragment of the sequence in (a), said fragment comprising at least 50 amino acids and being capable of inducing an immune response against Chlamydia;

or the complementary polynucleotide sequence thereto.

2. The nucleic acid molecule according to claim 1 wherein, in (b), said fragment comprises at least 75 amino acids.

3. The nucleic acid molecule according to claim 1 wherein, in (b), said fragment comprises at least 100 amino acids.

4. The nucleic acid molecule according to claim 1 wherein, in (b), said amino acid sequence retains the specific antigenicity of SEQ ID NO:3.

5. The nucleic acid molecule of claim 1, said nucleic acid molecule comprising a polynucleotide sequence encoding the amino acid sequence as set forth in SEQ ID No:3, or the complementary polynucleotide sequence thereto.

6. The nucleic acid molecule of claim 1, wherein said polynucleotide sequence is the sequence set forth in SEQ ID NO:1 or 2, or the complementary polynucleotide sequence thereto.

7. An expression cassette comprising a polynucleotide sequence of claim 1 placed under the control of elements required for expression of the polynucleotide sequence.

8. An expression vector comprising the expression cassette of claim 7.

9. A vaccine vector comprising the nucleic acid of claim 1 placed under the control of elements required for expression.

10. The vector of claim 9 which is a plasmid vector.

11. The vector of claim 10 wherein said plasmid vector is plasmid pCAI327.

12. An immunogenic composition comprising a vaccine vector according to claim 9.

13. A method for inducing an immune response against Chlamydia, comprising administering to a host an effective amount of an immunogenic composition according to claim 12.

14. An immunogenic composition comprising a nucleic acid molecule according to claim 1.

15. An antibody that specifically binds to a polypeptide selected from the group consisting of:

(a) an amino acid sequence as set forth in SEQ ID No:3; and (b) a fragment of the sequence in (a), said fragment comprising at least 50 amino acids and being capable of inducing an immune response against Chlamydia.

16. A primer pair for PCR amplification of genomic nucleic acid encoding a POMP91A of a strain of *Chlamydia pneumoniae* from the genome of the strain of *Chlamydia pneumoniae* which comprises:

5' primer: 5'-ATAAGAAT<u>GCGGCCGC</u>CACCATGAAGCAGATGGTTCTTTGGG-3' (SEQ ID No:4) and 3' primer: 5'-GCGCC<u>GGTACC</u>GGAAACTAAGGGAGAGGCCTGCATG-3' (SEQ ID No:5).

* * * * *

SEQUENCE LISTING

<160> NUMBER OF SEQ ID NOS: 5

<210> SEQ ID NO 1
<211> LENGTH: 3050
<212> TYPE: DNA
<213> ORGANISM: Chlamydia pneumoniae

<400> SEQUENCE: 1
atgccattct cgagtcaact ttttatttcc gtgtatttat ttttctgttc tatgtaagtt 60
tagatctgta taaggctata acttattagg actccgacat atgaagcaga tgcgtctttg 120 gggatttta tttctctctt ccttctgtca agtttcttat ctacgagcaa acgatgttct 180
cctccctcta tcagggattc attctggaga agaccttgaa ctctttactc tacgcagttc 240
ctccccaaca aaaactacgt attctctacg caaagatttt attgtttgtg attttgcagg 300
aaattctatt cacaagcctg gagctgcatt cctgaactta aaaggcgatc tattttttat 360
aaatagcact cccctagcgg ctcttacctt taaaaacatt cacttaggag ctcgcggtgc 420
tgggctcttc tcggaatcca atgtgacctt caaaggcctg cactctctcg ttctcgaaaa 480
caacgaaagt tggggaggcg tcctcaccac atctggcgac ctttccttca taaataatac 540
cagtgtgctt tgtcaaaaca acattagcta tggacctgga ggagcgctac tcttacaagg 600
aagaaaaagc aaggctctct ttttcagaga caatcgagga acaattctat ttctgaaaaa 660

-continued

```
caaagccgtg aatcaagatg aatcccatcc tgggtacgga ggagctgtaa gtagtataag    720
tcctggctcc ccgattacct tcgctgacaa ccaagaaatc ctattccaag agaatgaggg    780
cgaacttggt ggagccattt ataacgatca gggtgccata acttttgaga ataactttca    840
aaccacaagc tttttctcta acaaagctag tttcgaggag ctgtctatag ccgctactgc    900
aatctctatt cacagtgggg cgataccta ttcactaaaa acgctgctgc aaaagttagg    960
cggagccatc catgcggatt atgttcatat aagagactgt aaaggaagca tcgtctttga   1020
ggagaactca gcaacagctg gaggggcaat cgcagtaaat gcagtttgtg acattaatgc   1080
tcaaggtcct gttcgcttta taaataactc tgcgttagga ctaaatggtg gtgctattta   1140
tatgcaggct actggatcta tattgcgctt acatgcaaat caaggagata ttgaattttg   1200
tggaaataaa gtacgatcgc agtttcattc acatataaat tccacttcaa acttcacaaa   1260
taatgccatt actatccaag gagcgcctcg agaattttcg ctcagcgcga atgaaggaca   1320
tcgcatctgt ttctatgatc ctataatttc tgcaacagaa aactataact ctctgtacat   1380
caaccatcag agactttag aagccggggg tgctgtgatc ttttcaggag cacgcctatc   1440
tccagagcat aaaaaagaaa ataagaacaa aacttcgatt ataaaccagc ccgtacgtct   1500
ctgttctgga gtcctttcta tagaaggggg cgcgattctt gctgttcgtt ctttttatca   1560
agaaggaggt cttcttgctc tcgggccagg ttctaaactg accactcaag ggaaaaattc   1620
tgaaaaagat aaaattgtca tcacaaattt aggattcaac ctagaaaatc tagactcttc   1680
ggatcctgca gaaatccgag ctacagaaaa agcctctatt gaaatttctg gagttcctag   1740
agtctatggt cacacagaat ctttctatga aaatcatgag tatgcctcca aaccttatac   1800
aacttcgatt attctatctg ccaaaaaact tgttacagct ccctctaggc cagagaaaga   1860
catccaaaat ctcatcatcg ctgaatctga gtatatgggc tacggctatc aaggctcatg   1920
ggaattctcc tggtctccta acgacactaa agaaaagaaa accattatag cctcttggac   1980
tcctacagga gaattttctt tagatccgaa gcgccgtgga tctttcattc ccacaacctt   2040
atggtcgaca ttctctgggc tgaatatagc atcgaatatc gtgaataaca attacctcaa   2100
caactccgag gtcatccccc tgcaacatct ctgtgttttt ggaggccctg tctatcagat   2160
tatggagcaa aatcctaaac agagctctaa caatctctta gttcaacatg cgggtcataa   2220
tgttggagct agaattcctt tctctttcaa taccatattg agtgctgcac ttactcaact   2280
cttctcttct tcatcacaac aaaatgttgc tgataagagc cacgcgcaaa tattgatagg   2340
gactgtatct cttaataaaa gttggcaagc actatctctt agatcttcat ttagctatac   2400
ggaagactct caggtaatga agcacgtatt cccctataaa gggacctctc gaggatcttg   2460
gagaaactac ggatggtccg gatctgtcgg catgtcttac gcctatccta aaggaatccg   2520
ctatctaaag atgactccct ttgttgacct tcagtataca aagttagtac aaaatccctt   2580
tgtggaaacg ggttatgacc ctagatattt ttcttcctcg gagatgacga acctatctct   2640
accgataggt atcgctttag aaatgcgctt tataggctcg cgttcttccc tatttctcca   2700
agtcagcacc tcgtacatta aagacttacg tcgggtcaac ccacaatctt cagcttcctt   2760
ggtgttaaat cactacacgt gggatatcca aggagtccct ctagggaaag aagctctaaa   2820
cattacctta aatagcacga ttaagtacaa gattgtgact gcctatatgg ggatttctag   2880
cacccaacga gaaggcagta acctttcggc aaatgctcat gcaggcctct cccttagttt   2940
ctagaagtta gcactataga aataaaagaa gacttaaaaa gcgcgtggtt atcattcaaa   3000
```

-continued cacgcgcttt tttatccctt gcctaattta tccatctgat ttatctatca 3050

<210> SEQ ID NO 2
<211> LENGTH: 2841
<212> TYPE: DNA
<213> ORGANISM: Chlamydia pneumoniae

<400> SEQUENCE: 2
atgaagcaga tgcgtctttg gggattttta tttctctctt ccttctgtca agtttcttat 60
ctacgagcaa acgatgttct cctccctcta tcagggattc attctggaga agaccttgaa 120
ctctttactc tacgcagttc ctccccaaca aaaactacgt attctctacg caaagatttt 180
attgtttgtg attttgcagg aaattctatt cacaagcctg gagctgcatt cctgaactta 240
aaaggcgatc tattttttat aaatagcact cccctagcgg ctcttacctt taaaaacatt 300
cacttaggag ctcgcggtgc tgggctcttc tcggaatcca atgtgacctt caaaggcctg 360
cactctctcg ttctcgaaaa caacgaaagt tggggaggcg tcctcaccac atctggcgac 420
ctttccttca taaataatac cagtgtgctt tgtcaaaaca acattagcta tggacctgga 480
ggagcgctac tcttacaagg aagaaaaagc aaggctctct ttttcagaga caatcgagga 540
acaattctat ttctgaaaaa caaagccgtg aatcaagatg aatcccatcc tgggtacgga 600
ggagctgtaa gtagtataag tcctggctcc ccgattacct tcgctgacaa ccaagaaatc 660
ctattccaag agaatgaggg cgaacttggt ggagccattt ataacgatca gggtgccata 720
acttttgaga ataactttca aaccacaagc tttttctcta acaaagctag tttcgaggag 780
ctgtctatag ccgctactgc aatctctatt cacagtgggg cgatacccta ttcactaaaa 840
acgctgctgc aaaagttagg cggagccatc catgcggatt atgttcatat aagagactgt 900
aaaggaagca tcgtctttga ggagaactca gcaacagctg gaggggcaat cgcagtaaat 960
gcagtttgtg acattaatgc tcaaggtcct gttcgcttta taaataactc tgcgttagga 1020
ctaaatggtg gtgctattta tatgcaggct actggatcta tattgcgctt acatgcaaat 1080
caaggagata ttgaattttg tggaaataaa gtacgatcgc agtttcattc acatataaat 1140
tccacttcaa acttcacaaa taatgccatt actatccaag gagcgcctcg agaattttcg 1200
ctcagcgcga atgaaggaca tcgcatctgt ttctatgatc ctataatttc tgcaacagaa 1260
aactataact ctctgtacat caaccatcag agacttttag aagccggggg tgctgtgatc 1320
ttttcaggag cacgcctatc tccagagcat aaaaaagaaa ataagaacaa aacttcgatt 1380
ataaaccagc ccgtacgtct ctgttctgga gtcctttcta tagaaggggg cgcgattctt 1440
gctgttcgtt ctttttatca agaaggaggt cttcttgctc tcgggccagg ttctaaactg 1500
accactcaag ggaaaaattc tgaaaaagat aaaattgtca tcacaaattt aggattcaac 1560
ctagaaaatc tagactcttc ggatcctgca gaaatccgag ctacagaaaa agcctctatt 1620
gaaatttctg gagttcctag agtctatggt cacacagaat ctttctatga aaatcatgag 1680
tatgcctcca aaccttatac aacttcgatt attctatctg ccaaaaaact tgttacagct 1740
ccctctaggc cagagaaaga catccaaaat ctcatcatcg ctgaatctga gtatatgggc 1800
tacggctatc aaggctcatg ggaattctcc tggtctccta acgacactaa agaaaagaaa 1860
accattatag cctcttggac tcctacagga gaattttctt tagatccgaa gcgccgtgga 1920
tctttcattc ccacaacctt atggtcgaca ttctctgggc tgaatatagc atcgaatatc 1980
gtgaataaca attacctcaa caactccgag gtcatccccc tgcaacatct ctgtgttttt 2040
ggaggccctg tctatcagat tatggagcaa aatcctaaac agagctctaa caatctctta 2100

-continued

```
gttcaacatg cgggtcataa tgttggagct agaattcctt tctctttcaa taccatattg   2160

agtgctgcac ttactcaact cttctcttct tcatcacaac aaaatgttgc tgataagagc   2220

cacgcgcaaa tattgatagg gactgtatct cttaataaaa gttggcaagc actatctctt   2280

agatcttcat ttagctatac ggaagactct caggtaatga agcacgtatt cccctataaa   2340

gggacctctc gaggatcttg gagaaactac ggatggtccg gatctgtcgg catgtcttac   2400

gcctatccta aaggaatccg ctatctaaag atgactccct ttgttgacct tcagtataca   2460

aagttagtac aaaatccctt tgtggaaacg ggttatgacc ctagatattt ttcttcctcg   2520

gagatgacga acctatctct accgataggt atcgctttag aaatgcgctt tataggctcg   2580

cgttcttccc tatttctcca agtcagcacc tcgtacatta aagacttacg tcgggtcaac   2640

ccacaatctt cagcttcctt ggtgttaaat cactacacgt gggatatcca aggagtccct   2700

ctagggaaag aagctctaaa cattacctta aatagcacga ttaagtacaa gattgtgact   2760

gcctatatgg ggatttctag cacccaacga gaaggcagta acctttcggc aaatgctcat   2820

gcaggcctct cccttagttt c                                             2841
```

```
<210> SEQ ID NO 3
<211> LENGTH: 947
<212> TYPE: PRT
<213> ORGANISM: Chlamydia pneumoniae

<400> SEQUENCE: 3

Met Lys Gln Met Arg Leu Trp Gly Phe Leu Phe Leu Ser Ser Phe Cys
  1               5                  10                  15

Gln Val Ser Tyr Leu Arg Ala Asn Asp Val Leu Leu Pro Leu Ser Gly
             20                  25                  30

Ile His Ser Gly Glu Asp Leu Glu Leu Phe Thr Leu Arg Ser Ser Ser
         35                  40                  45

Pro Thr Lys Thr Thr Tyr Ser Leu Arg Lys Asp Phe Ile Val Cys Asp
     50                  55                  60

Phe Ala Gly Asn Ser Ile His Lys Pro Gly Ala Ala Phe Leu Asn Leu
 65                  70                  75                  80

Lys Gly Asp Leu Phe Phe Ile Asn Ser Thr Pro Leu Ala Ala Leu Thr
                 85                  90                  95

Phe Lys Asn Ile His Leu Gly Ala Arg Gly Ala Gly Leu Phe Ser Glu
            100                 105                 110

Ser Asn Val Thr Phe Lys Gly Leu His Ser Leu Val Leu Glu Asn Asn
        115                 120                 125

Glu Ser Trp Gly Gly Val Leu Thr Thr Ser Gly Asp Leu Ser Phe Ile
    130                 135                 140

Asn Asn Thr Ser Val Leu Cys Gln Asn Asn Ile Ser Tyr Gly Pro Gly
145                 150                 155                 160

Gly Ala Leu Leu Leu Gln Gly Arg Lys Ser Lys Ala Leu Phe Phe Arg
                165                 170                 175

Asp Asn Arg Gly Thr Ile Leu Phe Leu Lys Asn Lys Ala Val Asn Gln
            180                 185                 190

Asp Glu Ser His Pro Gly Tyr Gly Gly Ala Val Ser Ser Ile Ser Pro
        195                 200                 205

Gly Ser Pro Ile Thr Phe Ala Asp Asn Gln Glu Ile Leu Phe Gln Glu
    210                 215                 220

Asn Glu Gly Glu Leu Gly Gly Ala Ile Tyr Asn Asp Gln Gly Ala Ile
225                 230                 235                 240
```

-continued

```
Thr Phe Glu Asn Asn Phe Gln Thr Thr Ser Phe Phe Ser Asn Lys Ala
                245                 250                 255

Ser Phe Glu Glu Leu Ser Ile Ala Ala Thr Ala Ile Ser Ile His Ser
            260                 265                 270

Gly Ala Ile Pro Tyr Ser Leu Lys Thr Leu Leu Gln Lys Leu Gly Gly
        275                 280                 285

Ala Ile His Ala Asp Tyr Val His Ile Arg Asp Cys Lys Gly Ser Ile
    290                 295                 300

Val Phe Glu Glu Asn Ser Ala Thr Ala Gly Gly Ala Ile Ala Val Asn
305                 310                 315                 320

Ala Val Cys Asp Ile Asn Ala Gln Gly Pro Val Arg Phe Ile Asn Asn
                325                 330                 335

Ser Ala Leu Gly Leu Asn Gly Gly Ala Ile Tyr Met Gln Ala Thr Gly
            340                 345                 350

Ser Ile Leu Arg Leu His Ala Asn Gln Gly Asp Ile Glu Phe Cys Gly
        355                 360                 365

Asn Lys Val Arg Ser Gln Phe His Ser His Ile Asn Ser Thr Ser Asn
    370                 375                 380

Phe Thr Asn Asn Ala Ile Thr Ile Gln Gly Ala Pro Arg Glu Phe Ser
385                 390                 395                 400

Leu Ser Ala Asn Glu Gly His Arg Ile Cys Phe Tyr Asp Pro Ile Ile
                405                 410                 415

Ser Ala Thr Glu Asn Tyr Asn Ser Leu Tyr Ile Asn His Gln Arg Leu
            420                 425                 430

Leu Glu Ala Gly Gly Ala Val Ile Phe Ser Gly Ala Arg Leu Ser Pro
        435                 440                 445

Glu His Lys Lys Glu Asn Lys Asn Lys Thr Ser Ile Ile Asn Gln Pro
    450                 455                 460

Val Arg Leu Cys Ser Gly Val Leu Ser Ile Glu Gly Gly Ala Ile Leu
465                 470                 475                 480

Ala Val Arg Ser Phe Tyr Gln Glu Gly Gly Leu Leu Ala Leu Gly Pro
                485                 490                 495

Gly Ser Lys Leu Thr Thr Gln Gly Lys Asn Ser Glu Lys Asp Lys Ile
            500                 505                 510

Val Ile Thr Asn Leu Gly Phe Asn Leu Glu Asn Leu Asp Ser Ser Asp
        515                 520                 525

Pro Ala Glu Ile Arg Ala Thr Glu Lys Ala Ser Ile Glu Ile Ser Gly
    530                 535                 540

Val Pro Arg Val Tyr Gly His Thr Glu Ser Phe Tyr Glu Asn His Glu
545                 550                 555                 560

Tyr Ala Ser Lys Pro Tyr Thr Thr Ser Ile Ile Leu Ser Ala Lys Lys
                565                 570                 575

Leu Val Thr Ala Pro Ser Arg Pro Glu Lys Asp Ile Gln Asn Leu Ile
            580                 585                 590

Ile Ala Glu Ser Glu Tyr Met Gly Tyr Gly Tyr Gln Gly Ser Trp Glu
        595                 600                 605

Phe Ser Trp Ser Pro Asn Asp Thr Lys Glu Lys Lys Thr Ile Ile Ala
    610                 615                 620

Ser Trp Thr Pro Thr Gly Glu Phe Ser Leu Asp Pro Lys Arg Arg Gly
625                 630                 635                 640

Ser Phe Ile Pro Thr Thr Leu Trp Ser Thr Phe Ser Gly Leu Asn Ile
                645                 650                 655
```

-continued

```
Ala Ser Asn Ile Val Asn Asn Asn Tyr Leu Asn Asn Ser Glu Val Ile
            660                 665                 670

Pro Leu Gln His Leu Cys Val Phe Gly Gly Pro Val Tyr Gln Ile Met
        675                 680                 685

Glu Gln Asn Pro Lys Gln Ser Ser Asn Asn Leu Leu Val Gln His Ala
    690                 695                 700

Gly His Asn Val Gly Ala Arg Ile Pro Phe Ser Phe Asn Thr Ile Leu
705                 710                 715                 720

Ser Ala Ala Leu Thr Gln Leu Phe Ser Ser Ser Ser Gln Gln Asn Val
                725                 730                 735

Ala Asp Lys Ser His Ala Gln Ile Leu Ile Gly Thr Val Ser Leu Asn
            740                 745                 750

Lys Ser Trp Gln Ala Leu Ser Leu Arg Ser Ser Phe Ser Tyr Thr Glu
        755                 760                 765

Asp Ser Gln Val Met Lys His Val Phe Pro Tyr Lys Gly Thr Ser Arg
    770                 775                 780

Gly Ser Trp Arg Asn Tyr Gly Trp Ser Gly Ser Val Gly Met Ser Tyr
785                 790                 795                 800

Ala Tyr Pro Lys Gly Ile Arg Tyr Leu Lys Met Thr Pro Phe Val Asp
                805                 810                 815

Leu Gln Tyr Thr Lys Leu Val Gln Asn Pro Phe Val Glu Thr Gly Tyr
            820                 825                 830

Asp Pro Arg Tyr Phe Ser Ser Ser Glu Met Thr Asn Leu Ser Leu Pro
        835                 840                 845

Ile Gly Ile Ala Leu Glu Met Arg Phe Ile Gly Ser Arg Ser Ser Leu
    850                 855                 860

Phe Leu Gln Val Ser Thr Ser Tyr Ile Lys Asp Leu Arg Arg Val Asn
865                 870                 875                 880

Pro Gln Ser Ser Ala Ser Leu Val Leu Asn His Tyr Thr Trp Asp Ile
                885                 890                 895

Gln Gly Val Pro Leu Gly Lys Glu Ala Leu Asn Ile Thr Leu Asn Ser
            900                 905                 910

Thr Ile Lys Tyr Lys Ile Val Thr Ala Tyr Met Gly Ile Ser Ser Thr
        915                 920                 925

Gln Arg Glu Gly Ser Asn Leu Ser Ala Asn Ala His Ala Gly Leu Ser
    930                 935                 940

Leu Ser Phe
945


<210> SEQ ID NO 4
<211> LENGTH: 43
<212> TYPE: DNA
<213> ORGANISM: Chlamydia pneumoniae

<400> SEQUENCE: 4

ataagaatgc ggccgccacc atgaagcaga tgcgtctttg ggg                     43


<210> SEQ ID NO 5
<211> LENGTH: 36
<212> TYPE: DNA
<213> ORGANISM: Chlamydia pneumoniae

<400> SEQUENCE: 5

gcgccggtac cggaaactaa gggagaggcc tgcatg                             36
```